US012797494B2

(12) United States Patent
Frangioni et al.

(10) Patent No.: US 12,797,494 B2
(45) **Date of Patent: *Nov. 17, 2026**

(54) ZWITTERIONIC METAL CHELATORS

(71) Applicant: Curadel Surgical Innovations, Inc., Natick, MA (US)

(72) Inventors: John V. Frangioni, Weston, MA (US); Wolfgang Maison, Winsen (DE)

(73) Assignee: Curadel Surgical Innovations, Inc., Bonita Springs, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 19/266,396

(22) Filed: Jul. 11, 2025

(65) Prior Publication Data

US 2025/0332295 A1 Oct. 30, 2025

Related U.S. Application Data

(63) Continuation of application No. 18/640,169, filed on Apr. 19, 2024.

(60) Provisional application No. 63/538,038, filed on Sep. 12, 2023.

(51) Int. Cl.

| | |
|---|---|
| ***A61K 51/04*** | (2006.01) |
| ***A61B 6/03*** | (2006.01) |
| ***A61K 49/00*** | (2006.01) |
| ***A61K 51/08*** | (2006.01) |

(52) U.S. Cl.

CPC .......... *A61K 51/0482* (2013.01); *A61B 6/037* (2013.01); *A61K 49/0032* (2013.01); *A61K 51/0478* (2013.01); *A61K 51/082* (2013.01); *A61K 2121/00* (2013.01); *A61K 2123/00* (2013.01)

(58) Field of Classification Search

CPC ............ A61K 51/0482; A61K 51/0478; A61K 49/0032; A61K 51/082; A61B 6/037

USPC ........................................................ 424/1.65

See application file for complete search history.

(56) References Cited

U.S. PATENT DOCUMENTS

| | | | |
|---|---|---|---|
| 6,083,485 | A | 7/2000 | Licha et al. |
| 6,258,340 | B1 | 7/2001 | Licha et al. |
| 6,440,389 | B1 | 8/2002 | Rabito |
| 6,913,743 | B2 | 7/2005 | Licha et al. |
| 6,926,885 | B2 | 8/2005 | Licha et al. |
| 7,025,949 | B2 | 4/2006 | Licha et al. |
| 7,445,767 | B2 | 11/2008 | Licha et al. |
| 7,582,483 | B2 | 9/2009 | Mizutani et al. |
| 7,655,217 | B2 | 2/2010 | Licha et al. |
| 7,682,603 | B2 | 3/2010 | Hammer et al. |
| 8,173,819 | B2 | 5/2012 | Rajopadhye et al. |
| 8,268,014 | B2 | 9/2012 | Frohling |
| 8,460,639 | B2 | 6/2013 | Nomoto et al. |
| 10,201,621 | B2 | 2/2019 | Frangioni et al. |
| 11,279,698 | B2 | 3/2022 | Babich et al. |
| 2001/0055567 | A1 | 12/2001 | Licha et al. |
| 2003/0026762 | A1 | 2/2003 | Malmros et al. |
| 2003/0026763 | A1 | 2/2003 | Licha et al. |
| 2003/0170179 | A1 | 9/2003 | Licha et al. |
| 2004/0028611 | A1 | 2/2004 | Frangioni |
| 2004/0029837 | A1 | 2/2004 | Fries et al. |
| 2004/0062713 | A1 | 4/2004 | Matsuo et al. |
| 2005/0106106 | A1 | 5/2005 | Licha et al. |
| 2005/0169844 | A1 | 8/2005 | Licha et al. |
| 2006/0040400 | A1 | 2/2006 | Mizutani et al. |
| 2006/0165598 | A1 | 7/2006 | Licha et al. |
| 2006/0165599 | A1 | 7/2006 | Licha et al. |
| 2006/0275209 | A1 | 12/2006 | Schweiger et al. |
| 2007/0292883 | A1 | 12/2007 | Ossovskaya et al. |
| 2008/0308744 | A1 | 12/2008 | Frangioni et al. |
| 2008/0318336 | A1 | 12/2008 | Scherninski et al. |
| 2009/0269277 | A1 | 10/2009 | Chang et al. |
| 2010/0035871 | A1 | 2/2010 | Stack et al. |
| 2010/0129293 | A1 | 5/2010 | Licha et al. |
| 2010/0323389 | A1 | 12/2010 | Xu et al. |
| 2012/0017931 | A1 | 1/2012 | Frohling |
| 2012/0045851 | A1 | 2/2012 | Scherninski et al. |
| 2013/0030282 | A1 | 1/2013 | Margel et al. |
| 2014/0063097 | A1 | 3/2014 | Liu et al. |

(Continued)

FOREIGN PATENT DOCUMENTS

| | | |
|---|---|---|
| JP | H5-150395 A | 6/1993 |
| JP | 2000-95758 A | 4/2000 |

(Continued)

OTHER PUBLICATIONS

Kriemen et al. Chem. Asian J. 2014, 9, 2197-2204. (Year: 2014).*
Li et al. Chem. Rev. 2022, 122, 17073-171154. (Year: 2022).*
Henry et al. J Label Compd Radiopharm. 2017, 60, S516. (Year: 2017).*
Choi et al. Nat. Biotech. 2013, 31, 148-154. (Year: 2013).*
Ciba-Geigy AG, "Use of dyes for shading during optical brightening of polyester and polyacrylonitrile substrates", Research Disclosure, 1982, vol. 216, Article No. 21611, pp. 107-109.
Yuan, L. et al. "A unique class of near-infrared functional fluorescent dyes with carboxylic-acid-modulated fluorescence ON/OFF switching rational design, synthesis, optical properties, theoretical calculations, and applications for fluorescence imaging in living animals", Journal of the American Chamical Society, 2012, vol. 134, No. 2, pp. 1200-1211.

(Continued)

*Primary Examiner* — Michael G. Hartley
*Assistant Examiner* — Sean R Donohue
(74) *Attorney, Agent, or Firm* — Troutman Pepper Locke LLP; Gabrielle L. Gelozin

(57) ABSTRACT

The present invention relates to zwitterionic metal chelators and their use as imaging, diagnostic, chemical processing, and treatment agents. These zwitterionic metal chelators have desirable properties that maximize solubility in aqueous environments, minimize non-specific interactions, and retain the ability to target thus resulting in an improved performance in a variety of medical, agricultural, and chemical processes. In in vivo and medical applications, zwitterionic metal chelators improve the signal-to-background ratio and therapeutic window as compared to other metal chelators while retaining high stability.

7 Claims, 5 Drawing Sheets

Specification includes a Sequence Listing.

(56) References Cited

U.S. PATENT DOCUMENTS

| | | | |
|---|---|---|---|
| 2015/0209451 | A1 | 7/2015 | Frangioni et al. |
| 2017/0290927 | A1 | 10/2017 | Frangioni et al. |
| 2022/0387631 | A1 | 12/2022 | Frangioni et al. |

FOREIGN PATENT DOCUMENTS

| | | | |
|---|---|---|---|
| JP | 2005-524072 | A | 8/2005 |
| JP | 2007-508282 | A | 4/2007 |
| JP | 2009-507035 | A | 2/2009 |
| JP | 2010-169677 | A | 8/2010 |
| JP | 2011-503067 | A | 1/2011 |
| JP | 2012-524153 | A | 10/2012 |
| JP | 2013-523725 | A | 6/2013 |
| JP | 2013-199477 | A | 10/2013 |
| WO | 2005/082423 | A2 | 9/2005 |
| WO | 2007/017602 | A2 | 2/2007 |
| WO | 2009/061473 | A2 | 5/2009 |
| WO | 2010/091243 | A1 | 8/2010 |
| WO | 2010/121163 | A2 | 10/2010 |
| WO | 2012/063028 | A1 | 5/2012 |
| WO | 2015/066290 | A1 | 5/2015 |

OTHER PUBLICATIONS

James, N.S. et al., "Evaluation of polymethine dyes as potential probes for near infrared fluorescence imaging of tumors: Part 1", Theranostics, Aug. 2013, vol. 3, No. 9, pp. 692-702.
Quek, C.-H. et al. "Near-infrared fluorescent nanoprobes for in vivo optical imaging", Nanomaterials, 2012, vol. 2, No. 2, pp. 92-112.
Ashitate, Y., et al. "Simultaneous mapping of pan and sentinel lymph nodes for real-time image guided surgery", Teranostics, Apr. 2014, vol. 4, No. 7, pp. 693-700.
Amiot, C. L. et al., "Near-infrared fluorescent materials for sensing of biological targets", Sensors, 2008, vol. 8, No. 5, pp. 3082-3105.
Tibre, A. G. J. et al., "Imaging technique implemented in CellTracks system," Cytometry, 2002, vol. 47, No. 4, pp. 248-255.
Chemical Physics Letters, Mar. 1996, vol. 250 pp. 261-265.
Gibbs "Near infrared fluorescence for image-guided surgery" Quant Imaging Med Surg, Jan. 1, 2012, pp. 177-187.
Journal of Photopolymer Science and Technology, 2000, vol. 13, No. 2, pp. 183-186.
Proceedings of SPIE, 2011, vol. 8114, pp. 81140 T-1 to 81140 T-9.
Sano, K. "Short PEG-linkers improve the performance of targeted, activable monoclonal antibody-indocyanine green optical imaging probes" Bioconjugate Chemistry, 2013 24(5), pp. 811-816.
European Journal of Medicinal Chemistry, 2012, vol. 54, pp. 647-659.
Office Action issued in Japanese Patent Application No. JP 2016-552234, dated Oct. 21, 2020.
Stoermer U et al., "Kann der metachromatische Index eine Hilfe bei der Krebsdiagnose sein?// The metachromatic index—an aid in cancer diagnosis?", Acta Histochemica, vol. 84, No. 1, Jan. 1, 1988, pp. 31-39.
Zimmermann U et al., "[Staining behavior and applicability of spectrally pure Capriblue GN, Stella Blue, Oxonin and Punky Blue]", Acta Histochemica, 1983, vol. 72, No. 1, pp. 55-69.
Winer, J. H., et al., "Intraoperative Localization of Insulinoma and Normal Pancreas Using Invisible Near-Infrared Fluorescent Light", Annals of Surgical Oncology, vol. 17, No. 4, Dec. 22, 2009, pp. 1094-1100.
Kate, P. G., et al., "Rapid and Selective Targeting of Heterogeneous Pancreatic Neuroendocrine Tumors", iScience, Apr. 24, 2020, pp. 101006-101006.
Extended European Search Report dated Feb. 13, 2023, issued during the prosecution of European Patent Application No. EP 22188587.4.
Ghanadzadeh et al. (Spectrochimica Acta Part A 2009, 73, 324-329).
Dao et al. (Australas. Phys. Eng. Sci. Med. 2004, 27, 224-229).
Sloviter (Cancer Res. 1949, 9, 677-680).
Yuan, L. et al. "A unique class of near-infrared functional fluorescent dyes with carboxylic-acid-modulated fluorescence on/off switching rational design, synthesis, optical properties, theoretical calculations, and applications for fluorescence imaging in living animals", Journal of the American Chemical Society, 2012, vol. 134, No. 2, pp. 1200-1211.
Ashitate, Y., et al. "Simultaneous mapping of pan and sentinel lymph nodes for real-time image guided surgery", Theranostics, Apr. 2014, vol. 4, No. 7, pp. 693-700.
Tibbe, A. G. J. et al., "Imaging technique implemented in CellTracks system," Cytometry, 2002, vol. 47, No. 4, pp. 248-255.
International Search Report issued in PCT/US2014/063104, dated Feb. 26, 2015.
International Search Report issued in PCT/US2014/063097, dated Apr. 10, 2015.
A. Swierzewski et al., DOTA-And DFO-Based Zwitterionic Chelators for 89ZR-PET), Universitat Hamburg, Fachbereich Chemie, Institute fur Pharmazie.
T. Lindner, et al., Radioligands Targeting Fibroblast Activation Protein (FAP)), Cancer 2021, 13, 5744.
Valk et al. (Clin. Cancer Res. 2020, 26, 3990-3998 and supplemental data).
Bao et al., (Chem. Commun. 2017, 53, 1611-1614.
Mulder et al. (Am Jnl. Nucl. Med. Mol. Imaging 2018, 8, 282-291).
De Jalon et al. (Mol. Imaging and Biol. 2023, 25, 144-155.
Hyun et al. (Mol. Imaging Biol. 2016, 18, 52-61).
Hensbergen et al. (Bioconj. Chem. 2020, 31, 375-395).
Njiojob et al. (J. Med. Chem. 2015, 58, 2845-2854).
Van Rymenant et al. (Frontier Chem. 2021, Article 640566, p. 1-12.
Slania et al. (J. Med. Chem 2021, 64, 4059-4070.
Park et al., Rapid & Selective Targeting of Heterogenous Pancreatic Neuroendocrine Tumors, IScience, 23, 101006, Apr. 24, 2020.

* cited by examiner $(ZWI)_4$-DOTA $(ZWI)_2$-macropa $(ZWI)_4$-porphyrin $(ZWI)_3$-NOTA $(ZWI)_3$-PyC3A $(ZWI)_4$-DFO*

(ZWI)$_3$-DOTA-tv

(ZWI)$_2$-macropa-tv

(ZWI)$_3$-porphyrin-tv

(ZWI)$_2$-NOTA-tv

(ZWI)$_3$-PYC$_3$A-tv

(ZWI)$_4$-DFO-tv

KUE dPSMA-617 cRGD

Scheme 2

(ZWI)$_3$-DOTA-AHX-KUE

Scheme 7

$NH_2$-$(ZWI)_4$-DFO*-$CO_2H$

SEQUENCE LISTING

```
Sequence total quantity: 6
SEQ ID NO: 1            moltype = AA  length = 9
FEATURE                 Location/Qualifiers
source                  1..9
                        mol_type = protein
                        organism = Homo sapiens
SEQUENCE: 1
CGQKRTRGC                                                          9

SEQ ID NO: 2            moltype = AA  length = 12
FEATURE                 Location/Qualifiers
source                  1..12
                        mol_type = protein
                        organism = Homo sapiens
SEQUENCE: 2
HTMYYHHYQH HL                                                      12

SEQ ID NO: 3            moltype = AA  length = 9
FEATURE                 Location/Qualifiers
source                  1..9
                        mol_type = protein
                        organism = Homo sapiens
SEQUENCE: 3
CRKRLDRNC                                                          9

SEQ ID NO: 4            moltype = AA  length = 6
FEATURE                 Location/Qualifiers
source                  1..6
                        mol_type = protein
                        organism = Homo sapiens
SEQUENCE: 4
CSPGAK                                                             6

SEQ ID NO: 5            moltype = AA  length = 8
FEATURE                 Location/Qualifiers
source                  1..8
                        mol_type = protein
                        organism = Homo sapiens
```

-continued

```
SEQUENCE: 5
FCFWKTCT                                                  8

SEQ ID NO: 6           moltype = AA  length = 14
FEATURE                Location/Qualifiers
source                 1..14
                       mol_type = protein
                       organism = Homo sapiens
SEQUENCE: 6
XQRLGNQWAV GHLM                                           14
```

ZWITTERIONIC METAL CHELATORS

CROSS-REFERENCE TO RELATED APPLICATIONS

This Application is a Continuation of application Ser. No. 18/640,169, filed Apr. 19, 2025, which application claims priority to U.S. Provisional Patent Application Ser. No. 63/538,038 filed Sep. 12, 2023, the entire contents of each of which are incorporated herein by references in their entireties.

SEQUENCE LISTING

A Sequence Listing conforming to the rules of WIPO Standard ST.26 is hereby incorporated by reference. Said Sequence Listing has been filed as an electronic document via PatentCenter encoded as XML in UTF-8 text. The electronic document, created on Apr. 17, 2024, is entitled "1515138 105US2.xml", and is 6,026 bytes in size.

FIELD OF THE INVENTION

The present invention relates to zwitterionic metal chelators and their use as imaging, diagnostic, chemical processing, and treatment agents. These zwitterionic metal chelators have desirable properties that maximize solubility in aqueous environments, minimize non-specific interactions, and retain the ability to target thus resulting in an improved performance in a variety of medical, agricultural, and chemical processes. In in vivo and medical applications, zwitterionic metal chelators improve the signal-to-background ratio and therapeutic window as compared to other metal chelators while retaining high stability.

BACKGROUND OF THE INVENTION

Cationic metals are insoluble in water. For this reason, whenever they are needed in a medical, agricultural, or chemical process they must be bound to, e.g. by coordination or chelation, to an organic compound that renders the complex soluble in aqueous environments and less toxic. Previously described metal chelators pay little attention to the polyionicity and sphere of hydration that is required to fully isolate the metal and thus result in unwanted non-specific interactions.

Chelated metals are commonly used in a variety of current imaging techniques. These techniques, like magnetic resonance imaging (MRI), single-photon emission computed tomography (SPECT), or positron emission tomography (PET), permit the detection of diseases at the cellular level. These imaging techniques rely on isotopes of Gd, Mn, Cu, Ga, Zr, Eu, Tc and many other metals—many of which are radioactive. In addition, isotopes of Cu, Lu, Ac, Pb, Bi, Y, Sc, Tb, Ra, Gd and others are often applied for therapeutic applications, such as radiotherapy and neutron capture therapy.

However, in the applications mentioned above, the metal isotope needs to be bound to metal chelators to prevent toxic effects and maintain association with the targeting vector. Many common metal chelators, such as DOTA, PyC3A, and macropa, lack the ability to be tuned with respect to the pharmacokinetics, solubility, non-specific tissue/organ uptake, and plasma-protein binding. In addition, common metal chelators are not easily cleared from the body resulting in accumulation in off-target tissues and organs. For diagnostic imaging, this results in higher background. For radiotherapy, this results in toxicity without benefit.

Similarly, in any agricultural or chemical processes that require metal chelation, little attention is currently paid to the level of aqueous solubility attained or mechanisms to minimize non-specific interactions that either lower the yield of the process or fail to block side reactions.

Some research has been undertaken to provide derivatives of these chelators by allowing for the conjugation of targeting vectors, such as antibodies, peptides, small molecules, and steroids. These derivatives are often produced by replacement of one or more carboxylic acid arms of the chelators to include a targeting vector. However, such replacement often has a substantial impact on the chelating properties of the chelator—rendering their metal-binding properties inferior, if not altogether useless for biomedical applications. In some instances, replacement alters the biodistribution and/or clearance of the molecule, which can lead to a higher background or a smaller therapeutic window.

As such, there remains a need for new and improved agents with high stability that maximize the solubility of metal complexes in aqueous environments, minimize non-specific/off-target interactions, equilibrate rapidly between the intravascular and extravascular spaces when injected into the body and are then cleared efficiently from the body, including by renal filtration. The zwitterionic metal chelators of the invention are directed toward these and other needs.

SUMMARY OF THE INVENTION

This invention provides for zwitterionic metal chelators which are useful for various medical, agriculture, and chemical processes. These chelators provide improved properties such as high solubility in aqueous environments and low non-specific interactions. When used in medical applications they can increase the signal-to-background ratio of imaged tissues and the therapeutic window of treated tissue, while allowing for easier and more efficient clearance by the subject.

In one aspect, the disclosure provides a zwitterionic metal chelator complex comprising a metal chelator having one or more zwitterionic groups and a metal or metal isotope selected from the group consisting of a radionuclide, a label, a paramagnetic metal and a heavy metal.

In certain embodiments, the metal chelator is a derivative of DOTA, deferoxamine, NOTA, PyC3A, macropa, or porphyrin. In still other embodiments, the zwitterionic metal chelator complexes further comprise one or more targeting vectors. In particular embodiments, the one or more targeting vectors are cRGD, PSMA-617, FAPI, octreotide, bombesin, or a homo- or hetero-dimer formed from their combination.

In some embodiments, wherein the metal chelator is a derivative of DOTA, the metal or metal isotope is Zr, Cu, Ga, In, Y, Gd, Lu, Ac, or Tb.

In other embodiments, wherein the metal chelator is PyC3A, the metal or metal isotope is Mn.

In still other embodiments, wherein the metal chelator is macropa, the metal or metal isotope is $Ac^{3+}$ or $Bi^{3+}$.

In yet other embodiments, wherein the metal chelator is a derivative of NOTA, the metal or metal isotope is $Ga^{3+}$, $Cu^{2+}$, $Gd^{3+}$, $Ac^{3+}$, or $Bi^{3+}$.

In other embodiments, wherein the metal chelator is a derivative of desferrioxamine, the metal or metal isotope is $Zr^{4+}$, $Fe^{3+}$, $Mn^{2+}$, or $Mn^{3+}$.

In still other embodiments, wherein the metal chelator is a derivative of porphyrin, the metal or metal isotope is $Mn^{2+}$, $Mn^{3+}$, $Fe^{2+}$, $Fe^{3+}$, $Gd^{3+}$, $Ac^{3+}$, or $Bi^{3+}$.

In some embodiments, the zwitterionic metal chelator of the zwitterionic metal chelator complex has the formula:

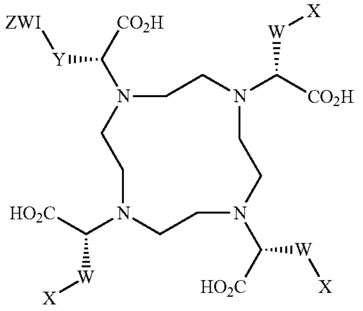

ZWI-DOTA-$X_3$ or

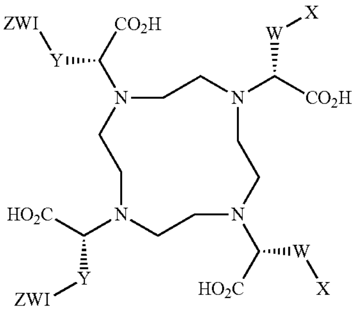

1,4-$(ZWI)_2$-DOTA-$X_2$ or

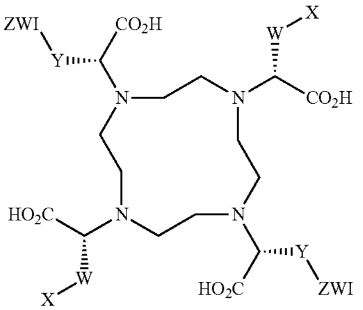

1,7-$(ZWI)_2$-DOTA-$X_2$

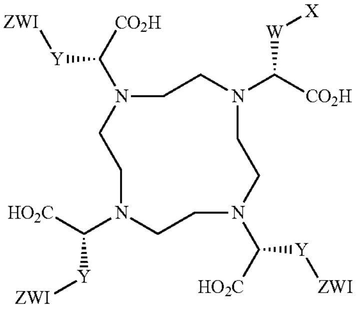

$(ZWI)_3$-DOTA-X or

-continued

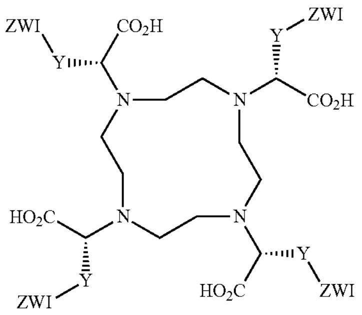

$(ZWI)_4$-DOTA wherein ZWI represents a zwitterionic group; each instance of W and Y independently represent a linking group, and each instance of X represents a reactive group.

In other embodiments, the zwitterionic metal chelator of the zwitterionic metal chelator complex has the formula:

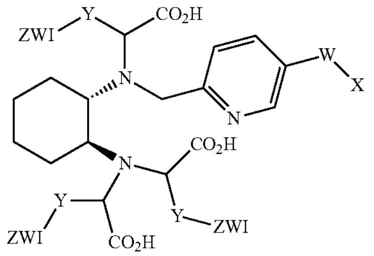

$(ZWI)_3$—$PyC_3A$-X

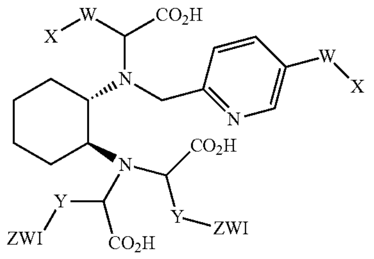

$(ZWI)_2$—$PyC_3A$-$X_2$

V1

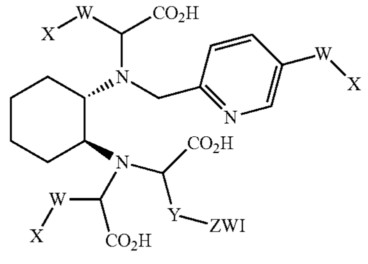

ZWI—$PyC_3A$-$X_3$

-continued

V2

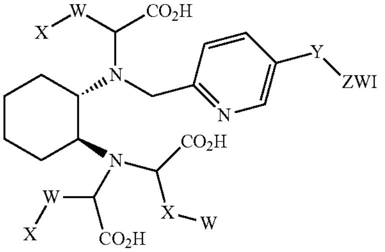

ZWI—PyC3A-X3

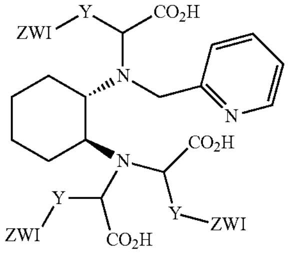

(ZWI)3—PyC3A

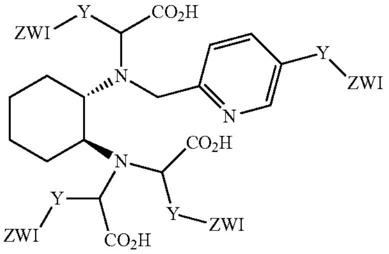

(ZWI)4—PyC3A wherein ZWI represents a zwitterionic group; each instance of W and Y independently represent a linking group, and each instance of X represents a reactive group.

In still other embodiments, the zwitterionic metal chelator of the zwitterionic metal chelator complex has the formula:

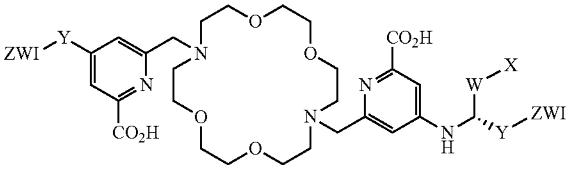

(ZWI)2-macropa-X

-continued

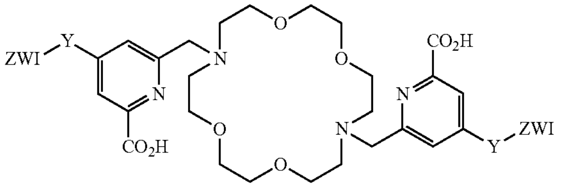

(ZWI)2-macropa

V1

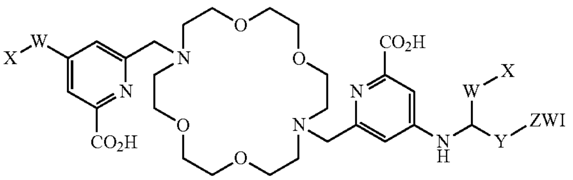

ZWI-macropa-X2

V2

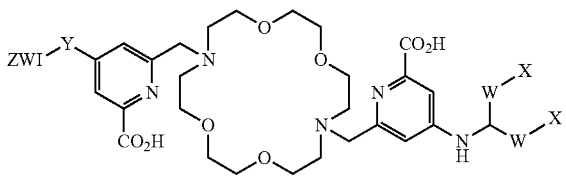

ZWI-macropa-X2 wherein ZWI represents a zwitterionic group; each instance of W and Y independently represent a linking group, and each instance of X represents a reactive group.

In yet other embodiments, the zwitterionic metal chelator of the zwitterionic metal chelator complex has the formula:

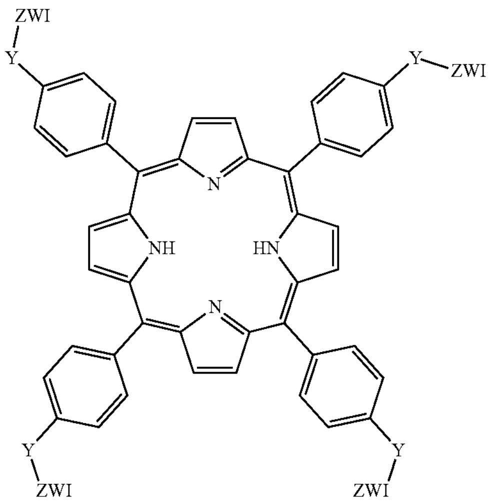

(ZWI)4-porphyrin

-continued

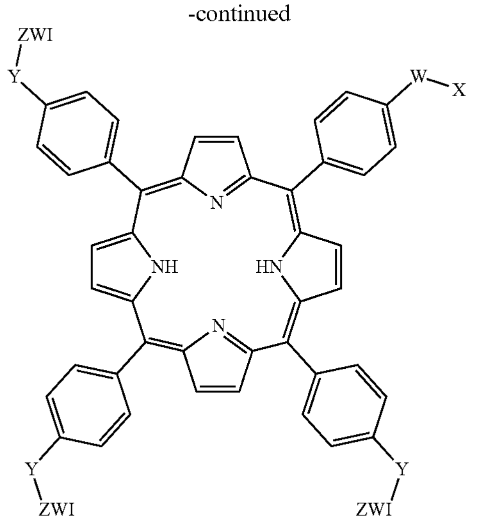

(ZWI)$_3$-porphyrin-X

V1

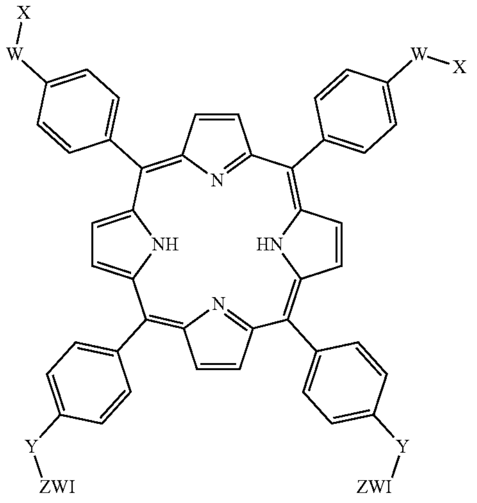

(ZWI)$_2$-porphyrin-X$_2$

V2

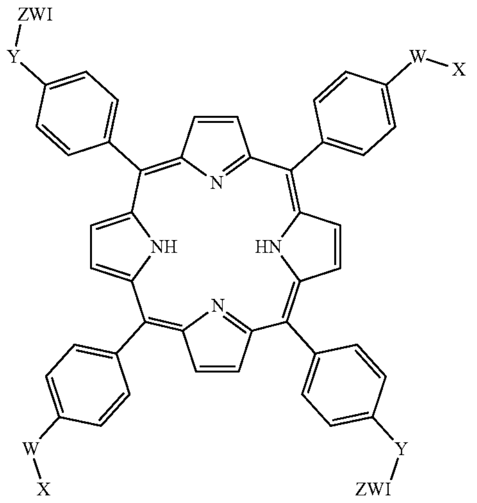

(ZWI)$_2$-porphyrin-X$_2$

-continued

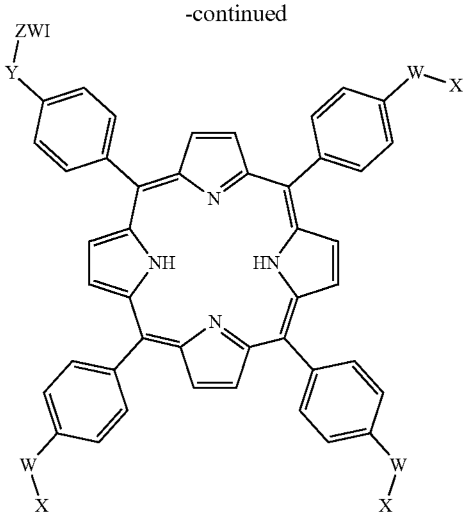

ZWI-porphyrin-X$_3$ wherein ZWI represents a zwitterionic group; each instance of W and Y independently represent a linking group, and each instance of X represents a reactive group.

In other embodiments, the zwitterionic metal chelator of the zwitterionic metal chelator complex has the formula:

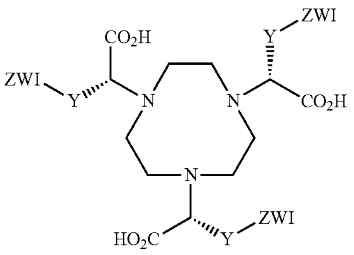

(ZWI)$_3$-NOTA

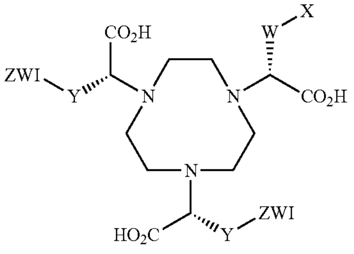

(ZWI)$_2$-NOTA-X

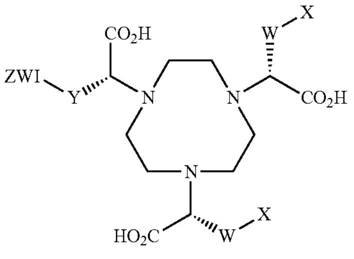

ZWI-NOTA-X$_2$ wherein ZWI represents a zwitterionic group; each instance of W and Y independently represent a linking group, and each instance of X represents a reactive group.
In yet other embodiments, the zwitterionic metal chelator of the zwitterionic metal chelator complex has the formula:
V1
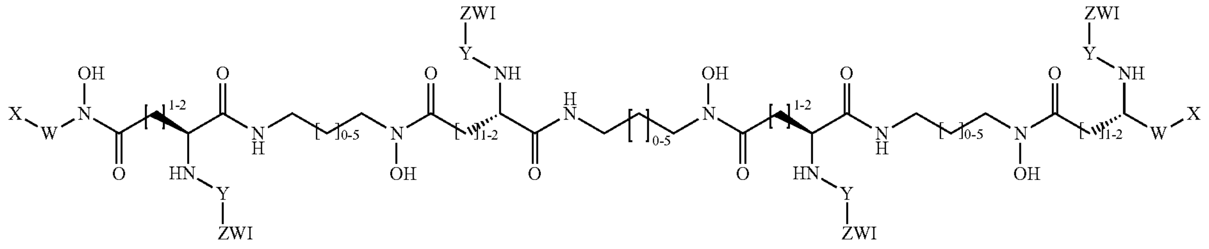
(ZWI)$_4$-DFO*-X$_2$
V1a
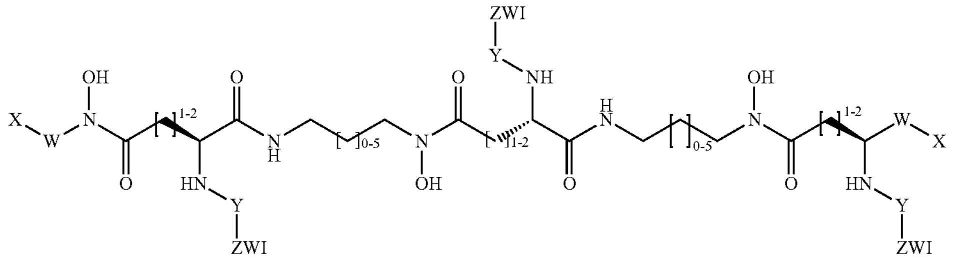
(ZWI)$_3$-DFO-X$_2$
V1b
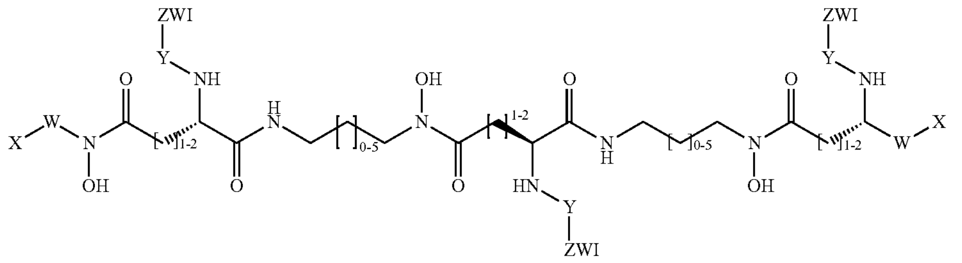
(ZWI)$_3$-DFO-X$_2$
V2
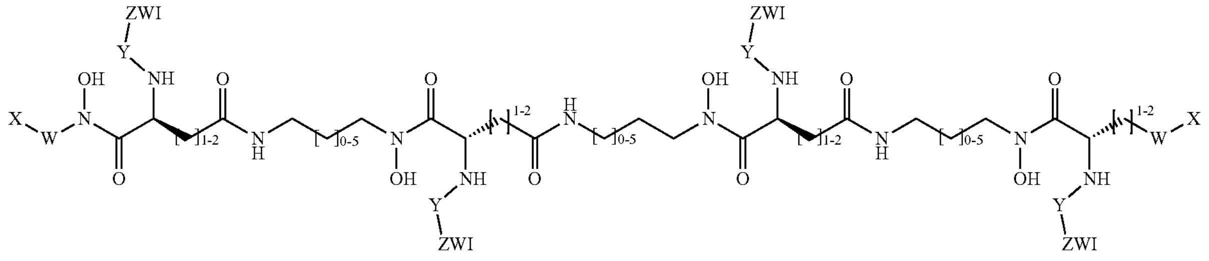
(ZWI)$_4$-DFO*-X$_2$ -continued
V2a
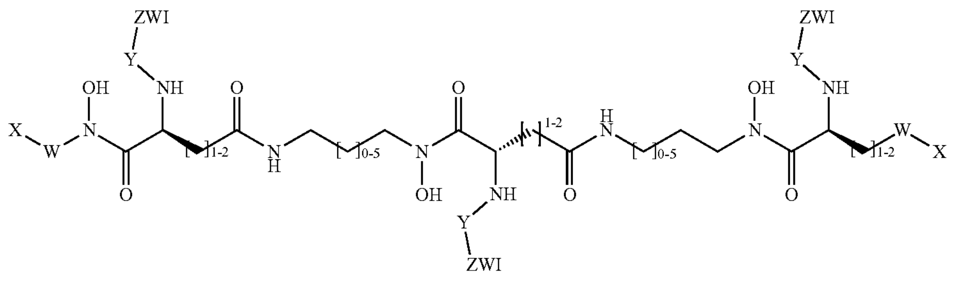
$(ZWI)_3$-DFO-$X_2$
V2b
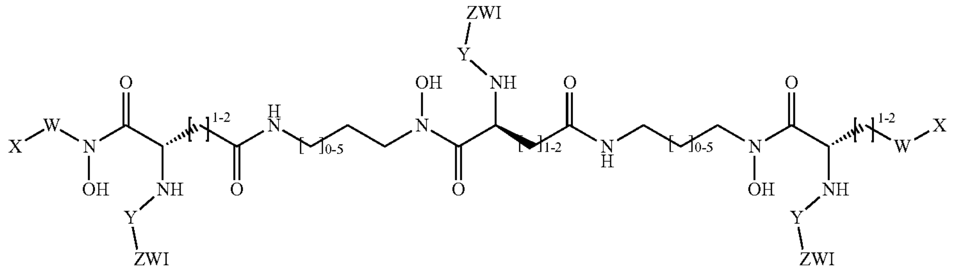
$(ZWI)_3$-DFO-$X_2$
V3
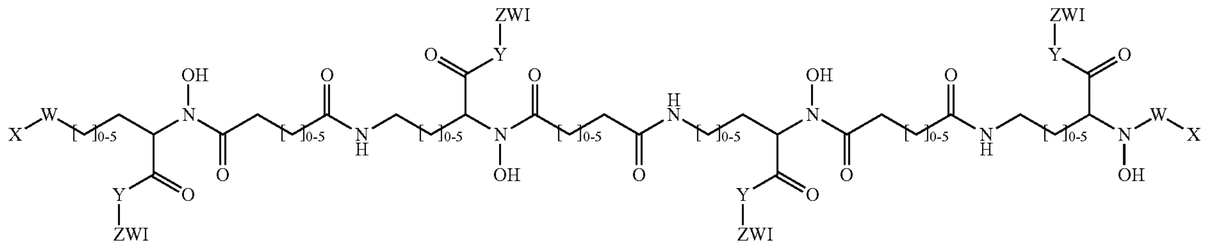
$(ZWI)_4$-DFO*-$X_2$
V3a
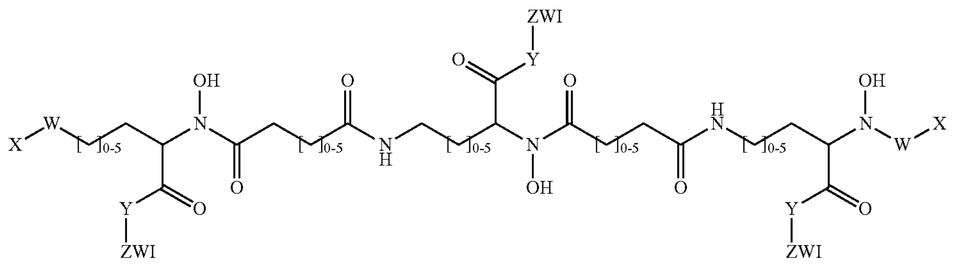
$(ZWI)_3$-DFO-$X_2$
V3b
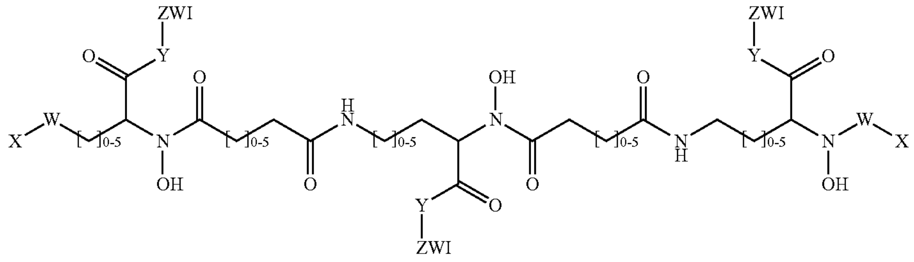
$(ZWI)_3$-DFO-$X_2$ -continued

V4

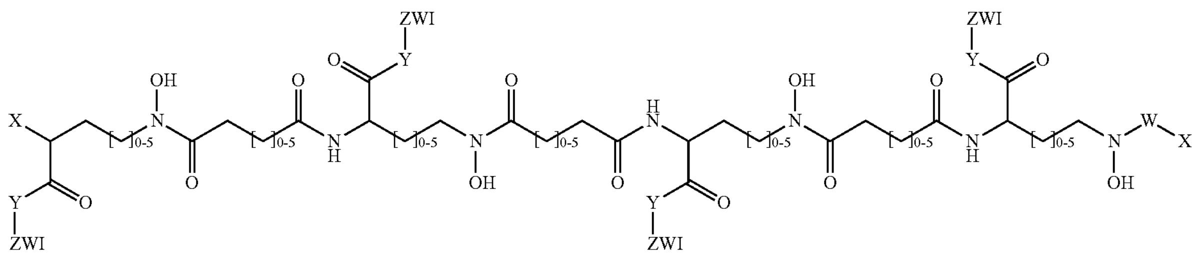

(ZWI)$_4$-DFO*-X$_2$

V4a

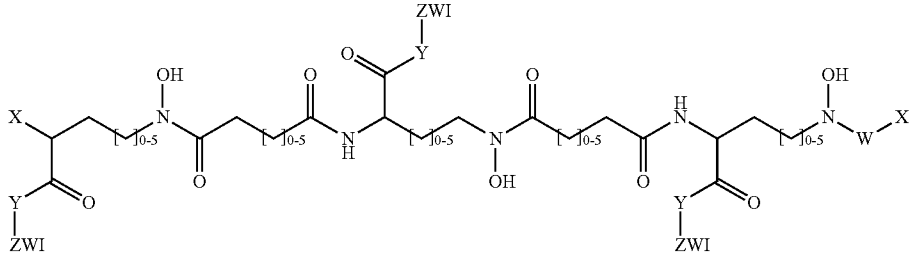

(ZWI)$_3$-DFO-X$_2$

V4b

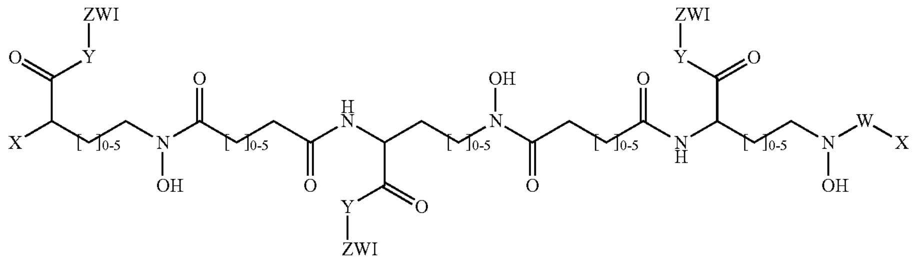

(ZWI)$_3$-DFO-X$_2$ wherein ZWI represents a zwitterionic group; each instance of W and Y independently represent a linking group, and each instance of X represents a reactive group.

In another aspect, the disclosure provides an imaging agent comprising a zwitterionic metal chelator complex according to the disclosure.

In another aspect, the disclosure provides a method of imaging cells, tissues, or organs, the method comprising:

(a) contacting cells with an imaging agent according to the disclosure; and (b) imaging the cells, tissues, or organs using positron emission tomography (PET), single-photon emission computerized tomography (SPECT), or magnetic resonance imaging (MRI).

In some embodiments of the method of imaging, the cells are tumor cells or cells undergoing angiogenesis.

In other embodiments of the method of imaging, t the imaging agent is administered to an organism comprising or suspected of comprising the cells.

In particular embodiments of the method of imaging, the organism is human.

In some embodiments of the method of imaging, the tissue or cells is imaged in vivo.

In another aspect, the disclosure provides therapeutic agent comprising a zwitterionic metal chelator complex according to the disclosure and a pharmaceutically acceptable carrier or excipient.

In another aspect, the disclosure provides a method of treating a cancerous condition in a subject in need thereof, the method comprising:

contacting cancer cells in the subject with an effective amount of a therapeutic agent according to the disclosure, wherein the metal atom complexed to the zwitterionic metal chelator is:

a radioactive metal isotope known to emit ionizing radiation that results in the death of cells that take up the analogs;

or a non-radioactive metal that is capable of releasing cytotoxic radiation upon irradiation with alpha emission, beta emission, neutron capture, or a combination thereof.

In some embodiments of the method of treatment, the metal atom complexed to the zwitterionic metal chelator is a non-radioactive metal that is capable of releasing cytotoxic radiation upon irradiation with alpha emission, beta emission, neutron capture, or a combination thereof; the method further comprising a step of irradiating the tumor cells using alpha emission, beta emission, neutron capture, or a combination thereof.

In some other embodiments of the method of treatment, the cancer cells are adult solid tumor cells or pediatric solid tumor cells.

In other embodiments of the method of treatment, the cancer cells are melanoma cells, neuroblastoma cells, lung cancer cells, adrenal cancer cells, colon cancer cells, colorectal cancer cells, ovarian cancer cells, prostate cancer cells, liver cancer cells, subcutaneous cancer cells, squamous cell cancer cells, intestinal cancer cells, retinoblastoma cells, cervical cancer cells, glioma cells, breast cancer cells, pancreatic cancer cells, Ewings sarcoma cells, rhabdomyosarcoma cells, osteosarcoma cells, retinoblastoma cells, Wilms' tumor cells, and pediatric brain tumor cells.

In some embodiments of the method of treatment, the cancer cells are prostate cancer cells. In some other embodiments of the method of treatment, the cancer cells are malignant cancer cells.

In another aspect, the disclosure provides method of treating a non-cancerous condition in a subject in need thereof, the method comprising:

administering to the subject an effective amount of a therapeutic agent according to the disclosure, wherein the metal atom complexed to the zwitterionic metal chelator is:

a radioactive metal isotope known to emit ionizing radiation that results in a therapeutic effect on the subject.

or a non-radioactive metal that is capable of releasing therapeutic radiation upon irradiation with alpha emission, beta emission, neutron capture, or a combination thereof.

In some embodiments of the method of treatment, the non-cancerous condition is a musculoskeletal disorders or a tissue hypertrophy disorder.

In some embodiments of the method of treatment, the subject is a human.

In another aspect, the disclosure provides a diagnostic agent comprising a zwitterionic metal chelator complex according to the disclosure and a pharmaceutically acceptable carrier or excipient.

In another aspect, the disclosure provides a method of measuring the efficacy of a biological system of a subject, the method comprising:

(a) administering a quantifiable amount of a diagnostic agent according to the disclosure to the subject;
(b) imaging the subject with positron emission tomography (PET), single-photon emission computerized tomography (SPECT), or magnetic resonance imaging (MRI); and
(c) determining the amount of therapeutic agent present in the biological system being observed in the subject.

In some embodiments of the method of measuring the efficacy of a biological system, the biological system is the renal system, the hepatic system, or the blood pool.

In another aspect, the disclosure provides a method of measuring the efficacy of renal function a subject, the method comprising:

(a) administering a quantifiable amount of a diagnostic agent according to the disclosure to the subject;
(b) imaging the subject with positron emission tomography (PET), single-photon emission computerized tomography (SPECT), or magnetic resonance imaging (MRI); and
(c) determining the amount of therapeutic agent present in the biological system being observed in the subject.

In another aspect, the disclosure provides a method of quantifying the glomerual filtration rate of a subject, the method comprising:

(a) administering a quantifiable amount of a diagnostic agent according to the disclosure to the subject;
(b) determining the amount of diagnostic agent present in the blood and urine of the subject as a function of time using either measurements of each bodily fluid or imaging the subject with positron emission tomography (PET), single-photon emission computerized tomography (SPECT), or magnetic resonance imaging (MRI)

In another aspect, the disclosure provides method for removing toxic or excess metals in a subject in need of such treatment, the method comprising:

(a) administering a therapeutically effective amount of a therapeutic agent according to the disclosure to the subject, wherein the therapeutic agent comprises a metal chelator having one or more zwitterionic groups which is not coordinated to a metal or metal isotope, and a pharmaceutically acceptable carrier or excipient.

In some embodiments of the method of removing toxic or excess metals in a subject, the metal chelator of the therapeutic agent has the formula:

V1

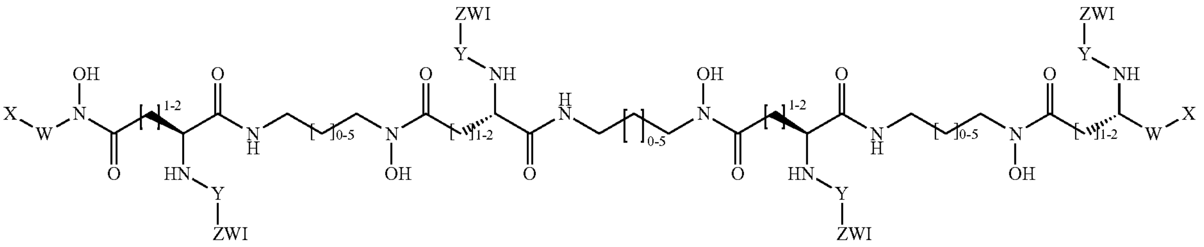

$(ZWI)_4$-DFO*-$X_2$

-continued
V1a
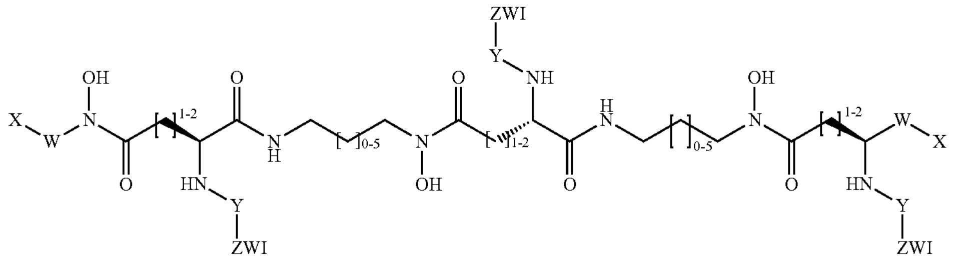
$(ZWI)_3$-DFO-$X_2$
V1b
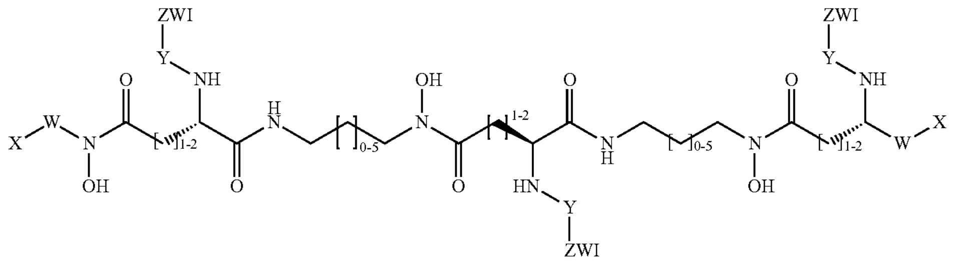
$(ZWI)_3$-DFO-$X_2$
V2
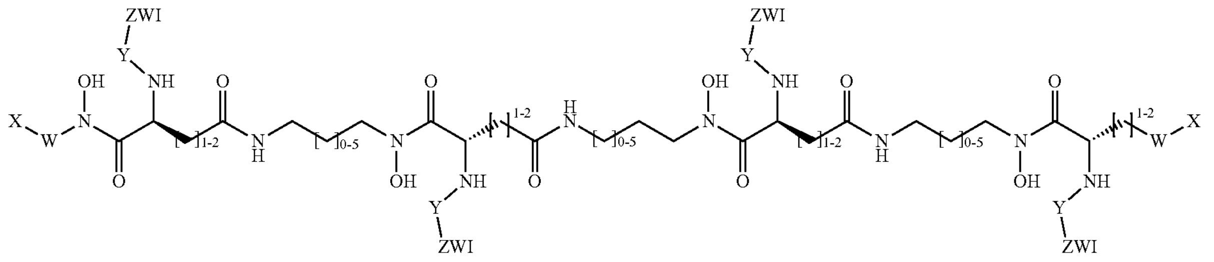
$(ZWI)_4$-DFO*-$X_2$
V2a
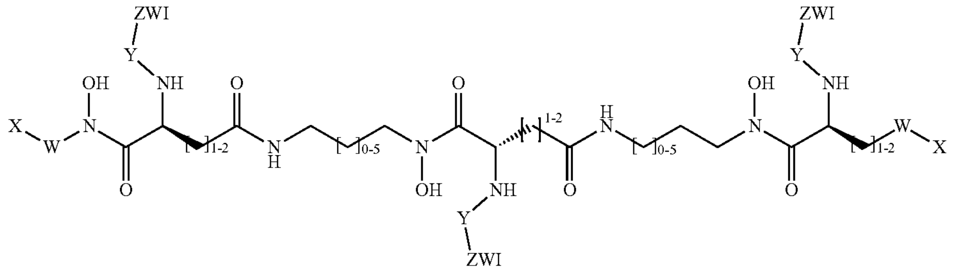
$(ZWI)_3$-DFO-$X_2$
V2b
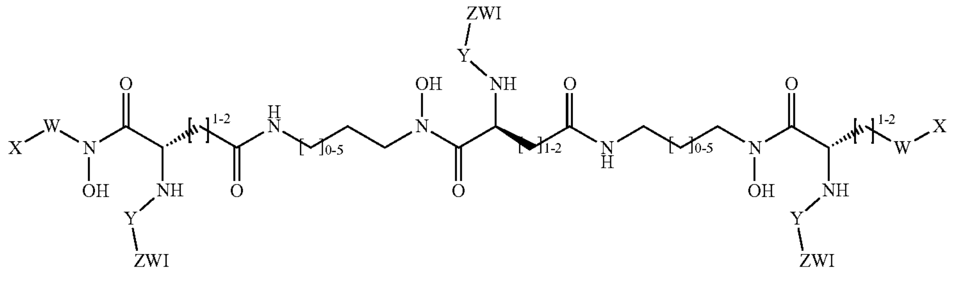
$(ZWI)_3$-DFO-$X_2$ -continued
V3
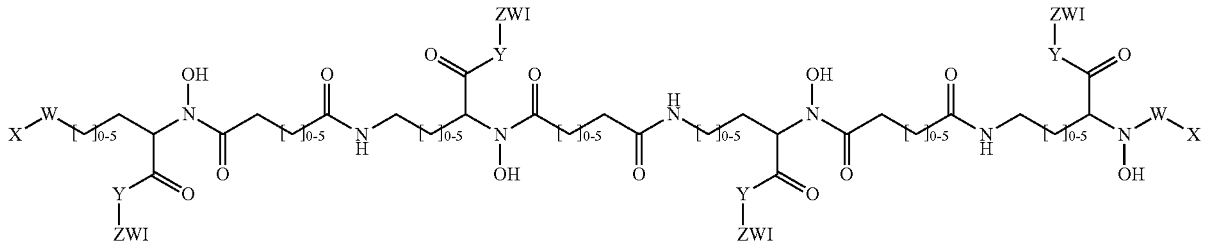
$(ZWI)_4$-DFO*-$X_2$
V3a
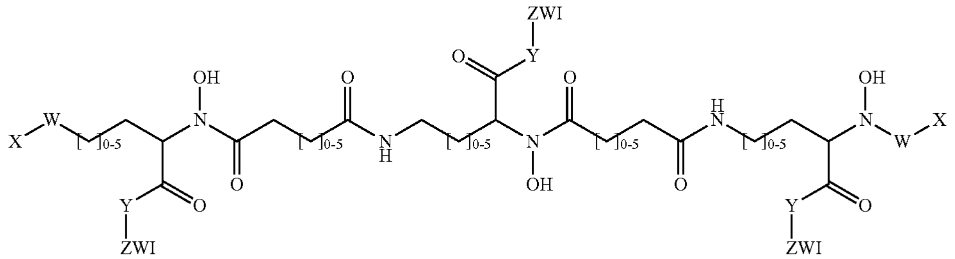
$(ZWI)_3$-DFO-$X_2$
V3b
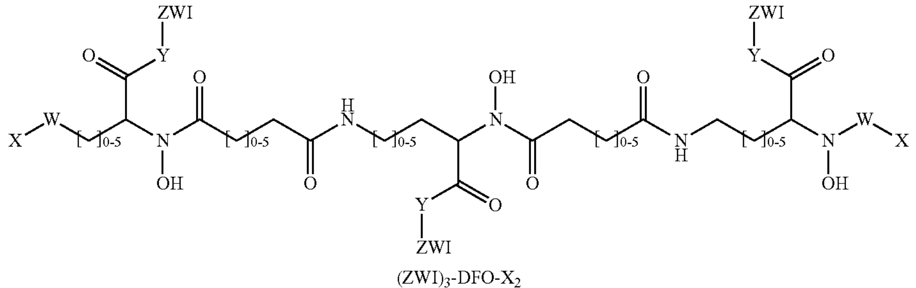
$(ZWI)_3$-DFO-$X_2$
V4
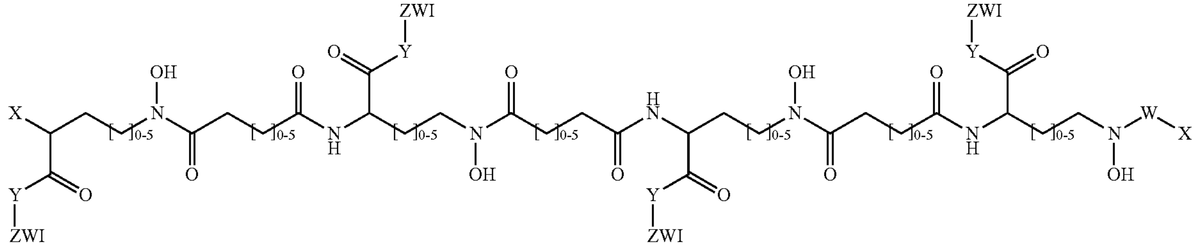
$(ZWI)_4$-DFO*-$X_2$
V4a
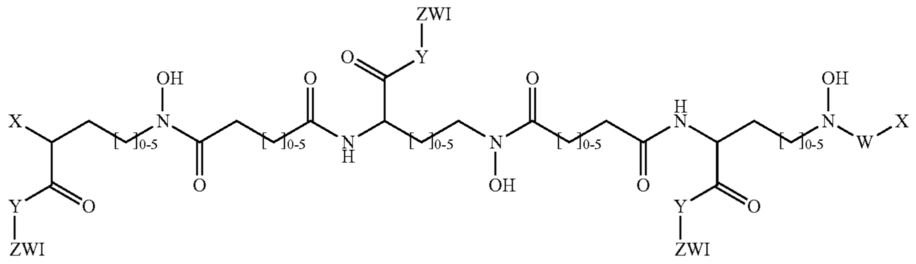
$(ZWI)_3$-DFO-$X_2$ -continued V4b

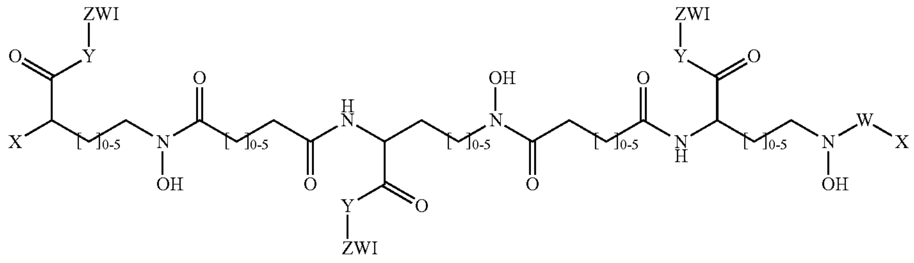

$(ZWI)_3$-DFO-$X_2$ wherein ZWI represents a zwitterionic group; each instance of W and Y independently represent a linking group, and each instance of X represents a reactive group.

In other embodiments of the method of removing toxic or excess metals in a subject, the toxic or excess metals are lead, mercury, arsenic, cadmium, thallium, iron, zinc, chromium, manganese, aluminum, cobalt, selenium, beryllium, lithium, silver, or tin.

In another aspect, the disclosure provides a radiosurgical method for treating a patient body, the method comprising: receiving a desired lesion pattern and planned radiation distribution;

administering an effective amount of a diagnostic agent according to the disclosure to the subject to effectively image the desired lesion pattern;

performing surgery on the desired lesion pattern to treat the patient body.

In some embodiments of the radiosurgical method of the disclosure, the zwitterionic metal chelator of the diagnostic agent further comprises one or more targeting vectors wherein the one or more targeting vectors are cRGD, PSMA-617, FAPI, octreotide, bombesin, or a homo- or hetero-dimer formed from their combination.

In other embodiments of the radiosurgical method of the disclosure, the desired lesion pattern is received from a user interface of a treatment planning module.

In still other embodiments of the radiosurgical method of the disclosure, the treatment planning module is pre-programmed with specifications for various disease states and cancerous conditions.

In yet other embodiments of the radiosurgical method of the disclosure, the the treatment planning module identifies lesion patterns for various disease states and cancerous conditions using artificial intelligence data.

In particular embodiments of the radiosurgical method of the disclosure, the n the surgery is performed using a sterotactic radiosurgical system.

In another aspect, the disclosure provides a method of treating a cancer by administering an effective amount of a therapeutic agent according to the disclosure, wherein the method comprises a step to diagnose the cancer and a step of administering the therapeutic agent to a subject determined to be in need thereof;

wherein the step to diagnose the cancer comprises:

contacting cells, tissues or organs of a subject with an imaging agent, imaging the cells, tissues, or organs of the subject using positron emission tomography (PET), single-photon emission computerized tomography (SPECT), or magnetic resonance imaging (MRI), and diagnosing the cancer in the cells tissues, or organs of the subject based on imaging data collected;

and wherein the metal atom complexed to the zwitterionic metal chelator is:

a radioactive metal isotope known to emit ionizing radiation that results in the death of cells that take up the analogs;

or a non-radioactive metal that is capable of releasing cytotoxic radiation upon irradiation with alpha emission, beta emission, neutron capture, or a combination thereof.

DETAILED DESCRIPTION

Figure 1:
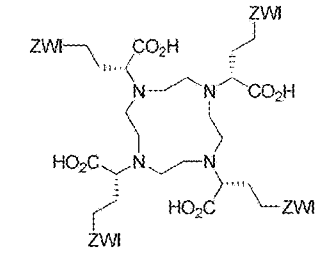
FIG. 1 is a representation of seven non-targeted zwitterionic metal chelators according to the invention.
Figure 1:
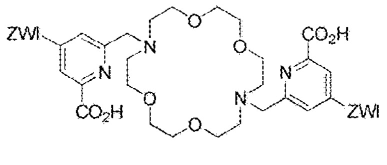
Figure 1:
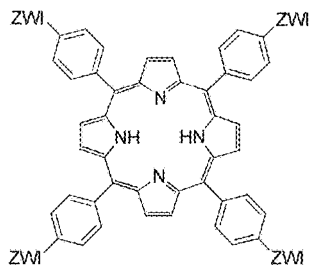
Figure 1:
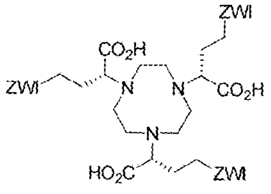
Figure 1:
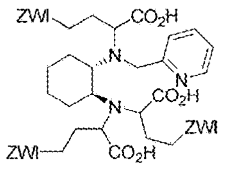
Figure 1:
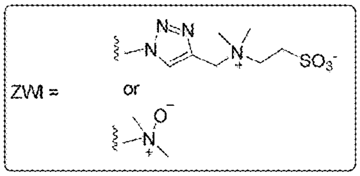
Figure 1:
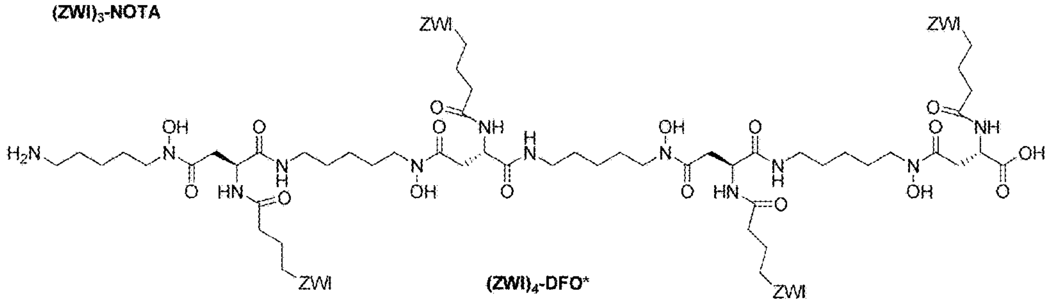

The present disclosure relates, inter alia, to an imaging, diagnostic, therapeutic or chemical agent that is composed of a zwitterionic metal chelator. In some aspects, the agents described herein are useful in, for example, the detection of abnormal or diseased biological tissues and cells. In some aspects, the zwitterionic metal chelators are particularly useful for imaging whole organisms as they have improved in vivo behavior, such as low non-specific binding to non-targeted tissues and high stability, resulting in an improved signal-to-background ratio in connection with the detected signal and/or improved therapeutic window. Similarly, in an agricultural or chemical process that now uses a metal chelator, zwitterionic metal chelators will improve solubility and minimize non-specific interactions. It is believed that these improved properties result from the balancing of formal charges on the metal chelator, rendering a polyionic yet "charge-balanced" molecule having a net charge that is neutral or close to neutral, with an extended sphere of hydration and better isolation of the metal.

DEFINITIONS AND ADDITIONAL EMBODIMENTS

The following definitions will be useful in understanding the instant invention.

As used herein, the term "comprising" is intended to mean that the compositions and methods include the recited elements, but do not exclude other elements. "Consisting essentially of", when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

As used in the specification and claims, the singular form "a", "an" and "the" include plural references unless the context clearly dictates otherwise.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless specifically stated or obvious from context, as used herein, the term "or" is understood to be inclusive.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

As used herein, the term "subject" or "patient" encompasses mammals and non-mammals. Examples of mammals include, but are not limited to, humans, chimpanzees, apes monkeys, cattle, horses, sheep, goats, swine; rabbits, dogs, cats, rats, mice, guinea pigs, and the like. Examples of non-mammals include, but are not limited to, birds, fish, parasites, microbes, and the like.

As used herein, the term "administration" or "administering" of the subject compound refers to providing a zwitterionic metal chelator of the invention and/or prodrugs thereof to a subject in need of diagnosis or treatment.

As used herein, the term "targeting vector" or "targeting ligand" refers to a moiety which is bound to or coordinated to the zwitterionic metal chelator of the invention to provide enhanced binding to particular cell types or an increased concentration in the presence of particular cell types. In certain embodiments, the targeting vector can be bound to the zwitterionic metal chelator in addition to the zwitterionic groups. In still other embodiments, the targeting vector can be bound to the zwitterionic metal chelator in place of one or more zwitterionic groups provided that the zwitterionic metal chelator retains at least one zwitterionic group.

As used herein, the term "therapeutic window" or "therapeutic index" refers to the relationship between the therapeutic and toxic dose of a given drug and is calculated using the ED50 and TD50 (Therapeutic Index=TD50/ED50). In certain embodiments of the invention, the zwitterionic metal chelators of the invention have a higher therapeutic index relative to other metal chelators. In certain other embodiments, the therapeutic window refers to a certainty safety factor (CSF) which is defined herein as the ratio of [$TD_1$/$ED_{99}$]. A CSF>1 indicates that the dose effective in 99% of the population is less than the dose that would be toxic in 1% of the population. In certain embodiments of the invention, the zwitterionic metal chelators of the invention have a higher CSF relative to other metal chelators.

As used herein, the term "carrier" refers to chemical compounds or agents that facilitate the incorporation of a compound described herein into cells or tissues.

As used herein, the term "acceptable" with respect to a formulation, composition or ingredient, as used herein, means having no persistent detrimental effect on the general health of the subject being treated.

As used herein, the term "diluent" refers to chemical compounds that are used to dilute a compound described herein prior to delivery. Diluents can also be used to stabilize compounds described herein.

As used herein, the term "zwitterionic group," "zwitterionic ligand," or "zwitterion" refer to one or more charged moieties or ligands which are present on or can be reacted with a metal chelator core. The zwitterionic metal chelators of the claimed invention are decorated by one or more zwitterionic groups, i.e., moieties combining positive (A+, FIG. 3) and negative charges (B−, FIG. 3) that sum to a net charge of zero. These zwitterionic groups are distinct from the chelator core itself, which typically has negative charges to chelate positively-charged metals. For example, a zwitterionic metal chelator with a chelator core of −4 that binds a +4 metal would have a total net charge of zero. Although a total net charge of zero is considered ideal, a zwitterionic metal chelator with a chelator core of −4 that binds a +2 metal, resulting in an overall charge of −2, would still be expected to exhibit improved properties in vivo because of shielding of the chelator core/metal complex by one or more zwitterionic groups. In the absence of zwitterionic groups, the molecule would have no such shielding or expanded water of hydration and would be more likely to bind non-specifically.

A particular active agent molecule may have several attached "zwitterionic groups" or charge pairs. In general, the anion portion and the cation portion of the zwitterionic group (charge pair) will be part of the same moiety, though it is possible for two ionic groups to be used as separate moieties to form a zwitterionic group. In particular embodiments, the zwitterionic group is covalently bound to the base structure via a carbon-carbon bond, a carbon-oxygen bond, or a nitrogen-carbon bond. Examples of zwitterionic groups (charge pairs) that can be included in the compounds and complexes of the claimed invention include, but are not limited to, ammoniophosphates, ammoniophosphonates, ammoniophosphinates, ammoniosulfonates, ammoniosulfates, ammoniocarboxylates, ammoniosulfonamides, ammonio-sulfon-imides, guanidiniocarboxylates, pyridiniocarboxylates, pyridiniosulfonates, ammonio(alkoxy)dicyanoethenolates, ammonioboronates, sulfoniocarboxylates, phophoniosulfonates, and phosphoniocarboxylates. The charged groups in these zwitterions can be separated by suitable spacer groups (C in FIG. 3) like linear or branched alkyl chains, aryl or heteroaryl moieties. In certain embodiments, the zwitterionic groups can be derivatives of amino acids, such as amino carboxylic acids, amino phosphonic acids, amino phosphinic acids or amino sulfonic acids, furthermore, aminoalkyl substituted sulfates or phosphates. Zwitterions can also be derivatives of betaines, such as carboxybetaines, sulfobetaines, sulfabetaines, phosphobetaines or phosphabetaines or N-oxides or derivatives of sulfamic acid. Particular examples of zwitterionic groups include ammonium sulfobetaines or N-oxides. A simple example of a zwitterionic group at physiological pH is the charge pair of a carboxylic acid (deprotonated at physiological pH) and an amine (protonated at physiological pH).

In some embodiments, the zwitterionic metal chelators of the invention can also comprise a targeting vector for an agricultural process, chemical process, disease, or tissue-specific epitope, such as the cyclic peptide cRGDyK (aka cRGD, FIG. 4) bound to one or more arms of the metal chelator. cRGD is a cyclic derivative of the tripeptide Arg-Gly-Asp which can be conjugated to one or more arms of the metal chelators of the invention. In still other embodiments, the targeting vector is octreotide or bombesin. In other embodiments, the targeting vector is KUE or dPSMA-617, a small molecule capable of targeting Fibroblast Activation Protein (FAP) also called FAP-inhibitor or FAPI, an amino acid or combination of amino acids, or derivatives thereof. In such embodiments, the targeting vector-conjugates can be formed in place of one or more zwitterionic groups. In certain embodiments, the targeting ligand includes one or more of LyP-1 peptide having a sequence of CGQKRTRGC (SEQ ID NO: 1) and binding to P32 for diagnosing/treating melanoma; K237 peptide having a sequence of HTMYYHHYQHHL (SEQ ID NO: 2) and binding to VEGFR-2 for diagnosing/treating breast tumor; IL4RPep-1 peptide having a sequence of CRKRLDRNC (SEQ ID NO: 3) and binding to IL4R for diagnosing/treating lung tumor, breast tumor, colon tumor; mUNO peptide having a sequence of CSPGAK (SEQ ID NO: 4) and binding to CD206 for diagnosing/treating breast tumor; folate receptors for diagnosing/treating ovarian and lung cancer; GE11, a dodecapeptide, binding to epidermal growth factor receptor (EGFR or ErbB1) for diagnosing/treating tumors of epithelial origin.

An ideal zwitterionic metal chelator conjugated to a targeting vector would adopt the total net charge of the targeting vector, which is purposeful because in most cases the charges on the targeting vector are crucial for the ability to bind its target. Targeted zwitterionic metal chelators thus retain the major advantage of minimizing non-specific binding while maximizing specific binding. It should be apparent to those skilled in the art that additional charges can be added to the zwitterionic metal chelator, if needed, to balance overall surface charge to zero.

In certain embodiments, the zwitterionic metal chelators of the invention chelator comprise a reactive linking group. Such reactive linking groups are typically an activated derivative of a carboxylic acid, such as an n-hydroxysuccinimide (NHS) ester, a sulfo-NHS ester, a pentafluorophenyl (PFP) ester, a hydroxybenzotriazole (HOBt) ester, a hydroxyazabenzotriazole (HOAt) ester, a tetrafluorophenyl (TFP) ester, an acid anhydride, an acid azide or an acid halide. Such reactive linking groups can be bound or substituted onto the chelator at any suitable structural location as would be understood by one of ordinary skill in the synthesis of such compounds. Reactive linking groups also include, but are not limited to, alkynes, azides, maleimides, thiols, amines, alcohols, phenols, carbonyls, phosphanes, alkenes and tetrazines.

As used herein, the term "contacting" refers to the bringing together of substances in physical contact such that the substances can interact with each other. For example, when an agent is "contacted" with tissue or cells, the tissue or cells can interact with the agent, for example, allowing the possibility of binding interactions between the agent and molecular components of the tissue or cells. "Contacting" is meant to include the administration of a substance such as an agent of the invention to an organism. Administration can be, for example, oral or parenteral.

As used herein, the term "ionic group" refers to a moiety comprising one or more charged substituents. The "charged substituent" is a functional group that is generally anionic or cationic when in substantially neutral aqueous conditions (e.g. a pH of about 6.5 to 8.0 or about physiological pH (7.4)). As recited above, examples of charged anionic substituents include anions of inorganic and organic acids such as sulfonate ($—SO_3^{1}—$), oxide, sulfinate, carboxylate, phosphinate, phosphonate, phosphate, and esters (such as alkyl esters) thereof. In some embodiments, the charged substituent is sulfonate or oxide. Examples of charged cationic substituents include quaternary ammonium ions ($—NR_3^+$) and phosphonium ions ($—PR_3^+$), where R is independently selected from $C_{1-6}$ linear alkyl, $C_{4-6}$ branched alkyl, $C_{3-6}$ cycloalkyl, aryl, heteroaryl and arylalkyl or heteroarylalkyl. Other charged cationic substituents include protonated primary, secondary, and tertiary amines, as well as guanidinium or amidinium or pyridinium or other protonated, alkylated or oxygenated nitrogen heterocycles. In some embodiments, the charged substituent is $—N(CH_3)_3^+$.

As used herein, the phrase "non-ionic oligomeric or polymeric solubilizing groups" refers to soluble polymers such as, for example, polyethylene glycol, polypropylene glycol, polyethylene oxide and propylene oxide copolymer, a carbohydrate, a dextran, polyacrylamide, a peptide and the like. The solubilizing group can be attached by any desired mode. The point of attachment can be, e.g., a carbon-carbon bond, a carbon-oxygen bond, or a nitrogen-carbon bond. The attachment group can be, e.g., an ester group, a carbonate group, an urea group, an alcohol group, an ether group, a sulfide group, an amino group, an alkylene group, an alkyne group, an azide group, a tetrazine, an amide group, a carbonyl group, or a phosphate group.

Some examples of solubilizing groups include polyethylene glycols, such as $—(CH_2CH_2O)_a—H$, $—OC(═O)O(CH_2CH_2O)_aH$, $—OC(═O)O(CH_2CH_2O)_aCH_3$, $—O(CH_2CH_2O)_aCH_3$, and $—S(CH_2CH_2O)_2CH_3$, "a" being an integer between about 2 and about 250. In some embodiments, "a" is 4 to 12 or 5 to 10. In further embodiments, "a" is 6, 7, or 8. Other examples of solubilizing groups include dextrans such as —OC(═O)O(dextran).

The solubilizing moiety can have an absolute molecular weight of from about 500 amu to about 100,000 amu, e.g., from about 1,000 amu to about 50,000 amu or from about 1,500 to about 25,000 amu.

Further examples of solubilizing groups include: $—(CH_2)_c—(OCH_2CH_2)_d—OR^a$, wherein "c" is 0 to 6, "d" is 1 to 200, and $R^a$ is H or $C_{1-6}$ alkyl. In some embodiments, "c" is 1 to 4, "d" is 1 to 10, and $R^a$ is H. In some embodiments, "d" is 6 or 7.

See WO 2008/017074, U.S. Ser. No. 12/376,243 (filed Feb. 3, 2009), and U.S. Ser. No. 12/376,225 (filed Feb. 3, 2009), each of which is incorporated herein by reference in its entirety, for a further description of suitable non-ionic oligomeric or polymeric solubilizing groups, and method for incorporating them into dyes.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Compounds of the invention can also include all isotopes of atoms occurring in the intermediates or final compounds. Isotopes include those atoms having the same atomic number but different mass numbers. For example, isotopes of hydrogen include tritium and deuterium.

The chemical substances represented herein by name, chemical formula, or structure are meant to include all stereoisomers, geometric isomers, tautomers, resonance structures, and isotopes of the same, unless otherwise specified.

The chemical substances described herein may be charged or include substituents with formal charges. When such chemical substances are represented as charged, it is understood that, unless otherwise specified, the charges are generally countered with an appropriate counterion. For example, chemical substances or functional groups having a charge of −1 are understood to be countered with an ion have a +1 charge. Suitable counterions with +1 charge include Na+, K+, tetraalkylammonium ions, and the like. Conversely chemical substances or functional groups having a charge of +1 are understood to be countered with an ion having a −1 charge. Suitable counterions with −1 charge include F−, Cl−, Br−, I−, sulfate, phosphate, perchlorate, acetate, trifluoroacetate, maleate, fumarate, mesylate, lactate, pyruvate, laevulinate, gluconate and the like.

Zwitterionic Metal Chelators Coordinated to a Metal Isotope

In certain aspects, the disclosure is directed to zwitterionic metal chelators coordinated to or labeled with a metal or metal isotope. In certain embodiments, the zwitterionic metal chelators coordinated to or labeled with a metal or metal isotope can be used medical, agricultural, or chemical processing applications.

Exemplary medical applications include applications for detection, imaging, or treatment in/of a subject or in a biological sample In certain embodiments, the disclosure further provides for treatment of benign and malignant tumors and tumor cells using a zwitterionic metal chelators labeled with a radioactive metal isotope known to emit ionizing radiation in a form that would result in the death of cells that take up the analogs labeled with the radioactive metal isotope. Metal chelators labeled with certain non-radioactive metal isotopes, such as Zr or Gd, can be used for neutron capture therapy.

Various zwitterionic metal chelators of the invention, particularly chelators suitable for use in the imaging methods provided by the invention, include one or more metals or radioisotopes capable of emitting one or more forms of radiation or other contrast (for example, effects on water relaxation) which are suitable for detection with any standard radiology method such as PET, SPECT, gamma cameras, MRI and the like.

For the disclosed methods of detecting/imaging benign or malignant tissues, any metal isotope known to emit radiation in a form that is readily detectable by conventional imaging means can be incorporated into the targeting backbone. Non-limiting examples of "conventional imaging means" include gamma ray detection, PET scanning, SPECT scanning, and MRT scanning. Non-limiting examples of metals that may be complexed with the chelators of the invention include Gd, Mn, Cu, Co, Y, In, Ga, Zr, Tc, Eu, Tb, Ac, Lu and other lanthanide or actinide metals. In some embodiments, the metals can be radioactive metal isotopes. Non-limiting examples of radioactive metal isotopes that may be used include Ga-66, Ga-67, Ga-68, Cu-64, Cu-67, Y-86, Co-55, Zr-89, Sr-83, Mn-52, As-72, Sc-44, Gd-153, Co-57, In-111, Ac-225, or Tc-99m.

For the disclosed methods of therapeutically treating malignant tumors, any radioactive metal isotope known to emit ionizing radiation in a form that would result in the death of cells that take up the analogs labeled with the radioactive metal isotope can be incorporated by chelation in the zwitterionic metal chelators of the invention. So, too, can non-radioactive metals that are capable of capturing neutrons and releasing cytotoxic radiation (neutron capture therapy). In some embodiments, the radioactive metal isotope emits its ionizing radiation in a form that minimizes damage to tissue outside of the cells that take up the labeled analogs. In certain embodiments, the invention provides compounds comprising one or more radioisotope suitable for use in radiation therapy. In certain embodiments, the zwitterionic metal chelators of the invention comprise at least one radioactive isotope of technetium, rhenium, gallium, indium, copper, yttrium, actinium, bismuth, samarium, dysprosium, holmium, or lutetium, including radioactive isotopes selected from Tc-99m, Tc-94m, Re-186, Re-188, Ga-68, Cu-64, Cu-67, Y-90, Y-86, Ac-225, Bi-213, In-111, Sm-153, Ho-166, Lu-177, Sc-43, Sc-44, Sc-47, Tb-149, Tb-152, Tb-155, Tb-161, and Dy-166. In other embodiments, non-limiting examples of metals used in neutron capture therapy include Zr-88 or Gd-157.

For the disclosed methods, the oxidation state of the metal coordinated to the chelator is not particularly limited. In general, the oxidation state can be adjusted based on the particular zwitterionic metal chelator used and the particular medical application used. In certain embodiments, the metal coordinated to the chelator has an oxidation state ranging from +1 to +5.

Various zwitterionic metal chelators of the invention are capable of generating at least a 2:1 target or signal to background ratio of radiation intensity, or more preferably about a 5:1, about a 10:1 or about a 15:1 ratio of radiation intensity between target and background.

Further, the zwitterionic metal chelators of the invention are excreted from tissues of the body quickly, and without significant non-specific uptake by off-target tissues and organs, to prevent prolonged exposure to the radiation of a radiolabeled compound or the toxic effects of non-radioactive metals administered to the patient. Typically zwitterionic metal chelators of the invention are eliminated from the body in less than about 24 hours. More preferably, compounds of the invention are eliminated from the body in less than about 16 hours, 12 hours, 8 hours, 6 hours, 4 hours, 2 hours, 90 minutes, or 60 minutes. Typically preferred compounds are eliminated in between about 60 minutes and about 120 minutes.

In some embodiments, the clearance of the zwitterionic metal chelators comprising the imaging agent or therapeutic agent is from the tumor, tissue, or organ in the subject. In some embodiments, there is more rapid clearance of the zwitterionic metal chelators comprising the imaging agent from the kidneys than from the tumor of the subject.

In some embodiments, the zwitterionic metal chelators are stable in vivo such that substantially all, e.g., more than about 50%, 60%, 70%, 80%, or more preferably 90% of the injected compound is not metabolized by the body prior to excretion. In other embodiments, the zwitterionic metal chelators are stable in vivo.

DOTA-Based Zwitterionic Metal Chelators

In one aspect, the invention provides a zwitterionic metal chelator based on 1,4,7,10-Tetraazacyclododecane-1,4,7,10-tetraacetic acid, also known as DOTA. Such zwitterionic metal chelators include the following:

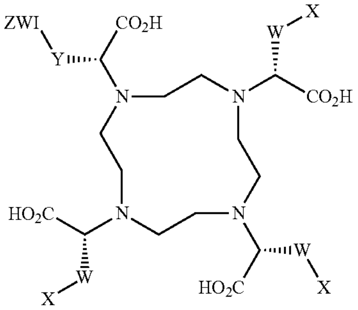

or

ZWI-DOTA-$X_3$

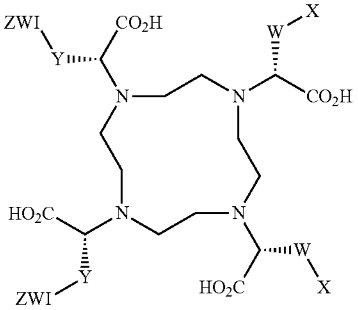

or 1,4-$(ZWI)_2$-DOTA-$X_2$

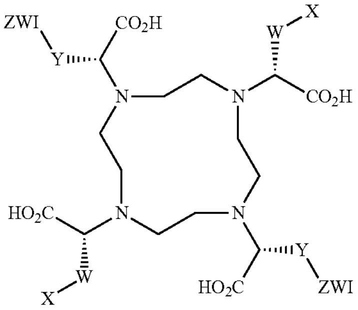

1,7-$(ZWI)_2$-DOTA-$X_2$

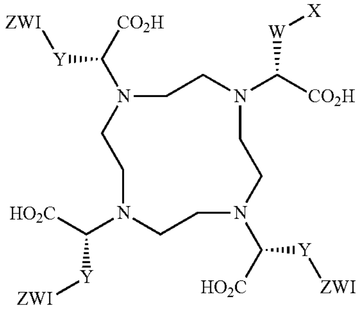

or $(ZWI)_3$-DOTA-X

-continued

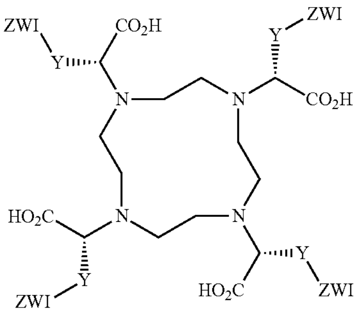

$(ZWI)_4$-DOTA in which ZWI represents a zwitterionic group; each instance of W and Y independently represent a linking group, and each instance of X represents a reactive group. In certain embodiments, ZWI represents an ammonium sulfobetaine group.

In such embodiments, a DOTA-based zwitterionic metal chelator contains stereogenic centers, any of these might have R or S-configuration. The DOTA-based zwitterionic metal chelator might be a single stereoisomer or might be a mixture of stereoisomers. The DOTA-based zwitterionic metal chelator includes 1, 2, 3, or 4 zwitterionic groups as defined in FIG. 3 and 1, 2 or 3 reactive groups X for conjugation to targeting vectors or other molecules or materials. This reactive group can be a carboxylic acid, an activated derivative of a carboxylic acid, such as an NHS ester, a sulfo-NHS ester, a PFP ester, a HOBt ester, a HOAt ester, a TFP ester, an acid anhydride, an acid azide or an acid halide. The reactive group X can also be an amine, azide, alkyne, alkene, ketone, aldehyde, alcohol, phenol, maleimide, thiol, phosphane or a tetrazine. The zwitterionic groups ZWI and the reactive groups X can be separated from the chelator core structure by appropriate spacer moieties W and Y including alkyl, aryl or heteroaryl groups. In particular embodiments, the DOTA-based zwitterionic metal chelator includes 1, 2, 3, or 4 zwitterionic groups and 4 carboxylate groups for complexation to the metal or metal isotope. In still other embodiments, the DOTA-based zwitterionic metal chelator includes 1, 2, 3, or 4 zwitterionic groups, 4 carboxylate groups for complexation to the metal or metal isotope, and one or more targeting vectors. These targeting vectors can be bound to the chelator at any suitable structural location (e.g. reactive group X) as would be understood by one of ordinary skill in the synthesis of such compounds.

DOTA-based zwitterionic metal chelators can be synthesized using the protocol described in Scheme 1.

Scheme 1

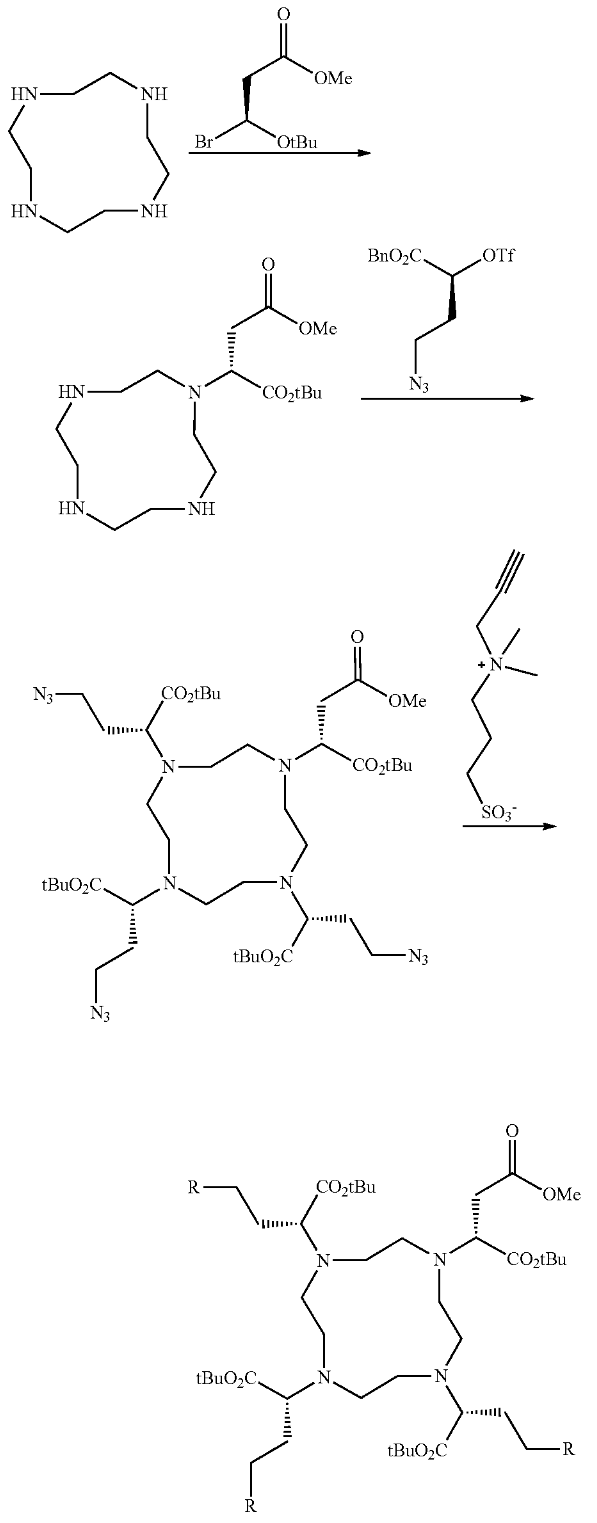

orthogonally protected
$(ZWI)_3$-DOTA-$CO_2Me$

-continued

R=

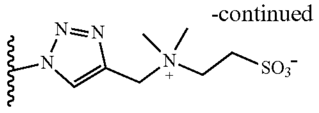

or

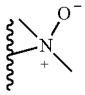

In a particular embodiment, the DOTA-based zwitterionic metal chelators can be complexed with Zr, Cu, Ga, In, Y, Gd, Lu, Ac, Tb or other metals.

In still other embodiments, one or more zwitterionic groups of the DOTA-based zwitterionic metal chelator can be replaced with a targeting vector, such as cRGD, dPSMA-617, KUE, a FAP-targeting small molecule, octreotide, bombesin, or their corresponding homo- or hetero-dimers provided that DOTA-based zwitterionic metal chelator remains zwitterionic. In certain embodiments, the targeting ligand includes one or more of LyP-1 peptide having a sequence of CGQKRTRGC (SEQ ID NO: 1) and binding to P32 for diagnosing/treating melanoma; K237 peptide having a sequence of HTMYYHHYQHHL (SEQ ID NO: 2) and binding to VEGFR-2 for diagnosing/treating breast tumor; IL4RPep-1 peptide having a sequence of CRKRLDRNC (SEQ ID NO: 3) and binding to IL4R for diagnosing/treating lung tumor, breast tumor, colon tumor; mUNO peptide having a sequence of CSPGAK (SEQ ID NO: 4) and binding to CD206 for diagnosing/treating breast tumor; folate receptors for diagnosing/treating ovarian and lung cancer; GE11, a dodecapeptide, binding to epidermal growth factor receptor (EGFR or ErbB1) for diagnosing/treating tumors of epithelial origin. Alternatively, the targeting vector can be covalently attached to a reactive linking group of the chelator compound of the invention through standard coupling procedures. For example, the carboxyl or activated carboxyl group of a reactive linking group can react with a nucleophilic functionality on the targeting vector, such as an amine or alcohol derivative, to form an amide or ester linkage. Additional details for the conjugation can be found in WO 2008/017074 and in Frangioni et al. Molecular Imaging, Vol. 1(4), 354-364 (2002), each of which is incorporated herein by reference in its entirety.

Figure 5:
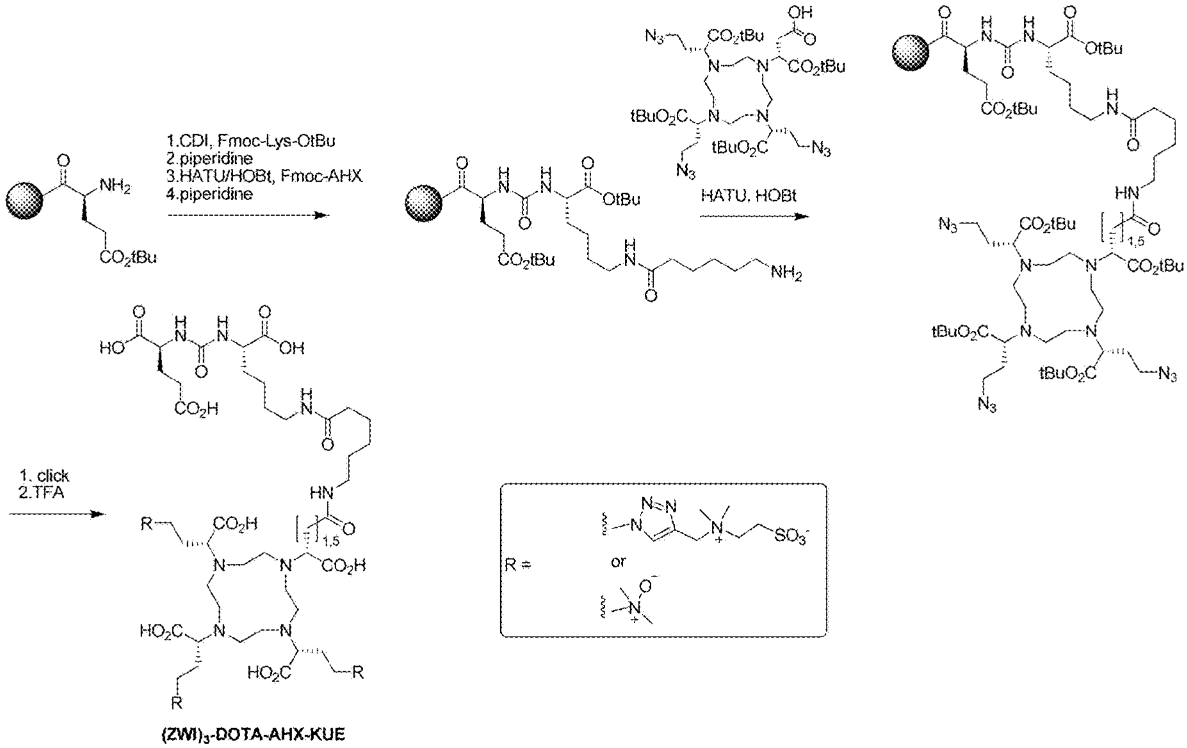
FIG. 5 is a representation of the synthesis of DOTA-based zwitterionic conjugates (Scheme 2)

It should be apparent to those skilled in the art, that if a targeting vector replaces a zwitterionic group, that zwitterionic group can be restored by adding it to the linker between the zwitterionic metal chelator and the targeting vector. The resulting structures of the conjugates are shown in FIG. 5. The zwitterions ZWI (as defined in FIG. 3) can be separated from the chelator core structure by appropriate spacer moieties Y including alkyl, aryl or heteroaryl groups. The targeting vectors (tv) can be separated from the chelator core structure by appropriate spacer moieties W including alkyl, aryl, heteroaryl, ether, ester, amide, imine and oxime groups. The spacers Y can also contain one or more ether or amide bond or a combination of both and might contain zwitterionic groups added to the sidechains of the spacer moiety. In certain embodiments, each of W and Y may independently be absent.

In certain embodiments, the agent further comprises a PEG-moiety to alter the circulation time in blood. Such moiety can be bound to the conjugate at any suitable structural location as would be understood by one of ordinary skill in the synthesis of such compounds.

In certain embodiments, the conjugate of the DOTA-based zwitterionic metal chelator and the targeting vector has the following formula with KUE, dPSMA-617, cRGD, FAPI, octreotide, bombesin, or as the targeting vector (tv):

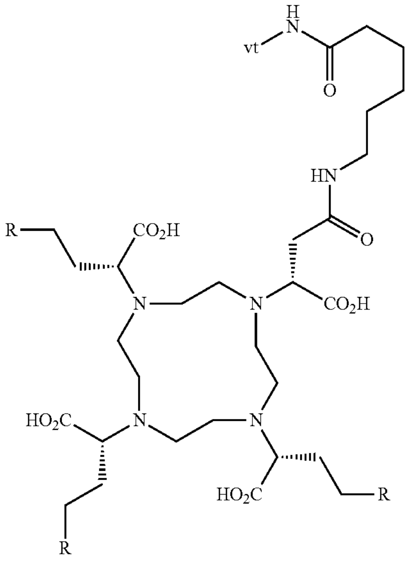

$(ZWI)_3$-DOTA-AHX-tv

-continued

R = 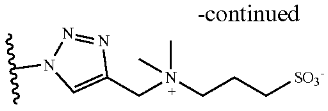 or 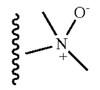

In certain embodiments, the targeting ligand includes one or more of LyP-1 peptide having a sequence of CGQKRTRGC (SEQ ID NO: 1) and binding to P32 for diagnosing/treating melanoma; K237 peptide having a sequence of HTMYYHHYQHHL (SEQ ID NO: 2) and binding to VEGFR-2 for diagnosing/treating breast tumor; IL4RPep-1 peptide having a sequence of CRKRLDRNC (SEQ ID NO: 3) and binding to IL4R for diagnosing/treating lung tumor, breast tumor, colon tumor; mUNO peptide having a sequence of CSPGAK (SEQ ID NO: 4) and binding to CD206 for diagnosing/treating breast tumor; folate receptors for diagnosing/treating ovarian and lung cancer; GE11, a dodecapeptide, binding to epidermal growth factor receptor (EGFR or ErbB1) for diagnosing/treating tumors of epithelial origin.

Such DOTA-based zwitterionic conjugates can be synthesized using the protocol described in Scheme 2 (shown in FIG. 5)

In certain embodiments, the DOTA-based zwitterionic metal chelators is not $ZWI_3$-DOTA-Ahx-cRGD.

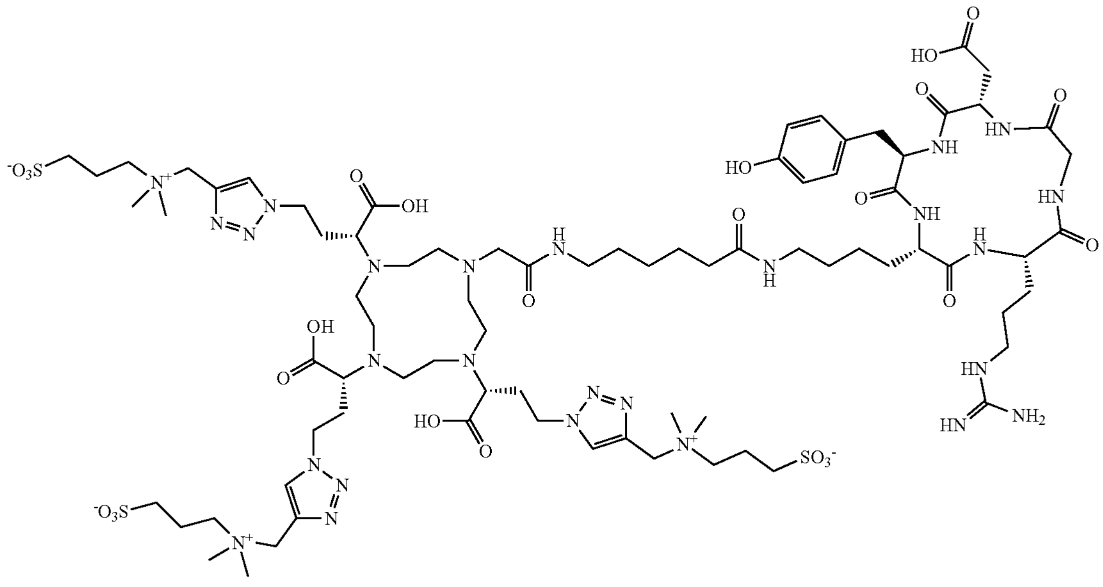

$ZWI_3$-DOTA-Ahx-cRGD

In certain embodiments, the DOTA-based zwitterionic metal chelators is not:
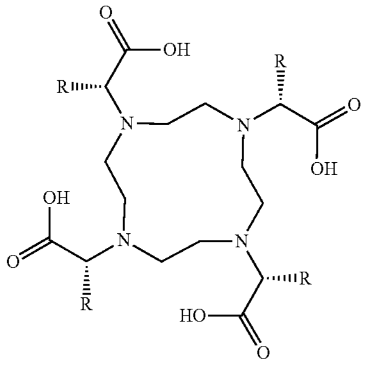
wherein
R =
triazol-ZWI =
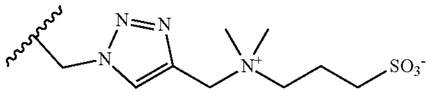
triazol-Solfo =
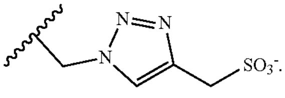
triazol-Kat =
In certain embodiments, the DOTA-based zwitterionic metal chelators is not:
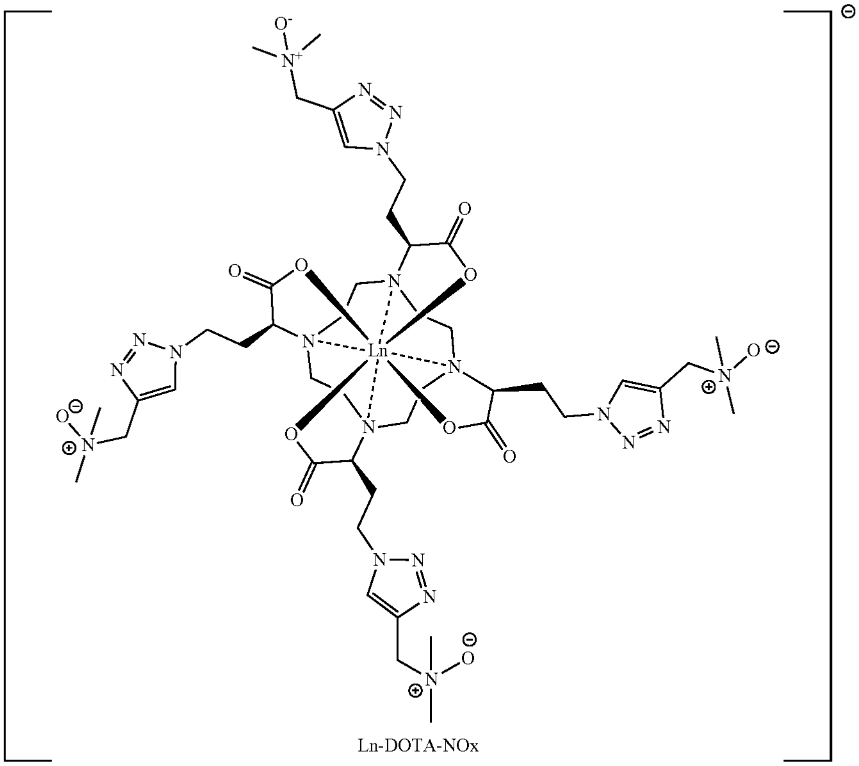
Ln-DOTA-NOx

PyC3A-Based Zwitterionic Metal Chelators

In one aspect, the invention provides a zwitterionic metal chelator based on N-picolyl-N,N',N'-trans-1,2-cyclohexenediaminetriacetate, also known as PyC3A. Such zwitterionic metal chelators include the following:

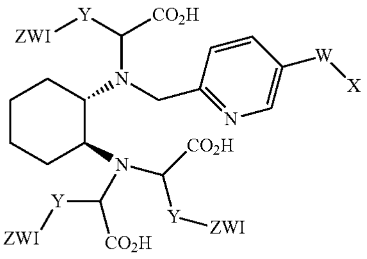

$(ZWI)_3$—$PyC_3A$-X

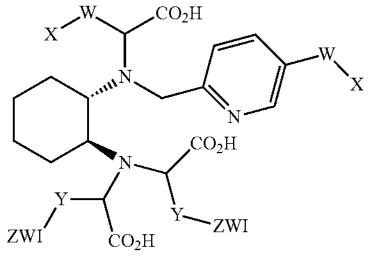

$(ZWI)_2$—$PyC_3A$-$X_2$

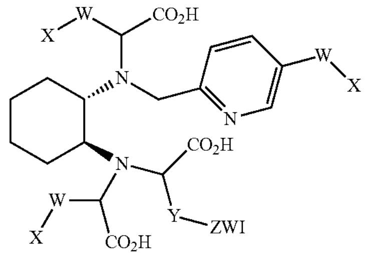

ZWI—$PyC_3A$-$X_3$

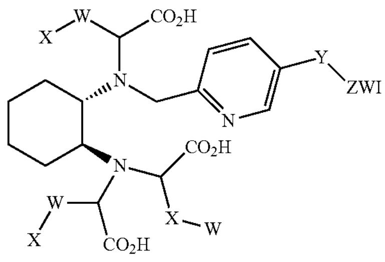

ZWI—$PyC_3A$-$X_3$

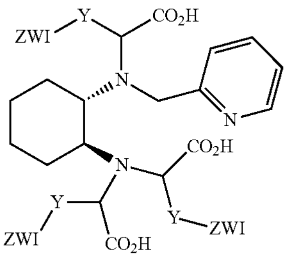

$(ZWI)_3$—$PyC_3A$

-continued

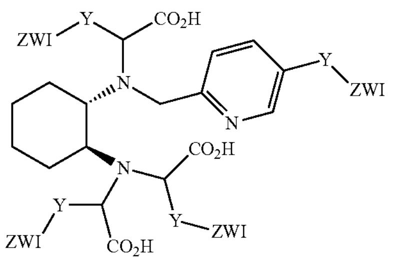

$(ZWI)_4$—$PyC_3A$

Figure 2:
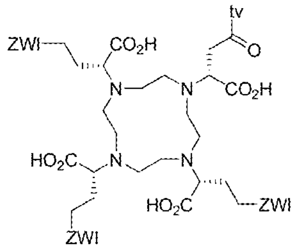
FIG. 2 is a representation of seven targeted zwitterionic metal chelators according to the invention (targeting vector=tv).
Figure 2:
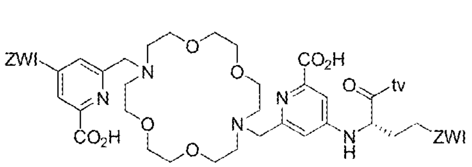
Figure 2:
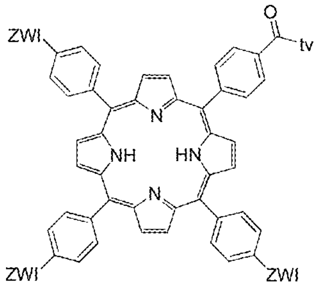
Figure 2:
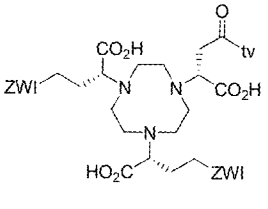
Figure 2:
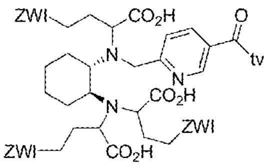
Figure 2:
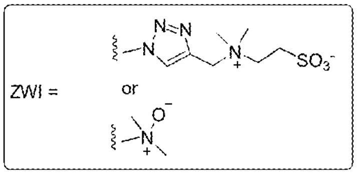
Figure 2:
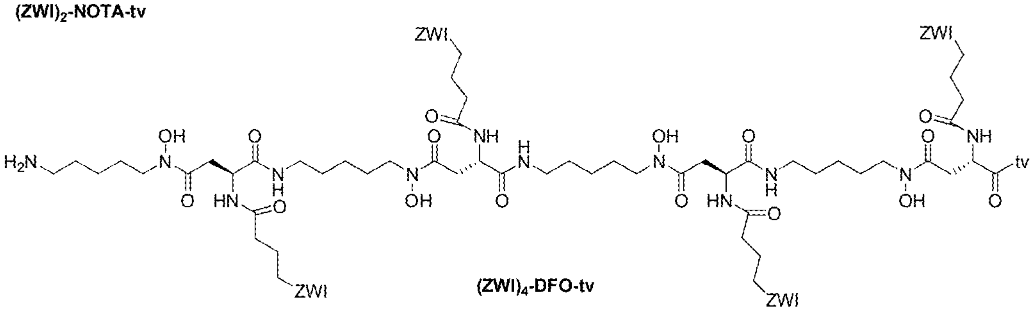
Figure 3:
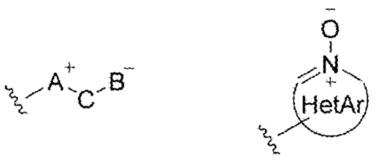
FIG. 3. is a representation of Zwitterionic groups according to the invention.

In such embodiments, a PyC3A-based zwitterionic metal chelator includes 1, 2 3 or 4, zwitterionic groups as defined in FIG. 3 and 1, 2 or 3 reactive groups X for conjugation to targeting vectors or other molecules or materials. This reactive group can be a carboxylic acid, an activated derivative of a carboxylic acid, such as an NHS ester, a sulfo-NHS ester, a PFP ester, a HOBt ester, a HOAt ester, a TFP ester, an acid anhydride, an acid azide or an acid halide. The reactive group X can also be an amine, azide, alkyne, alkene, ketone, aldehyde, alcohol, phenol, maleimide, thiol, phosphane or a tetrazine. The zwitterionic groups ZWI and the reactive groups X can be separated from the chelator core structure by appropriate spacer moieties W and Y including alkyl, aryl or heteroaryl groups. In certain embodiments, each of W and Y may independently be absent. In certain embodiments, ZWI represents an ammonium sulfobetaine group.

PyC3A-based zwitterionic metal chelators can be synthesized using the protocol described in Scheme 3.

Scheme 3

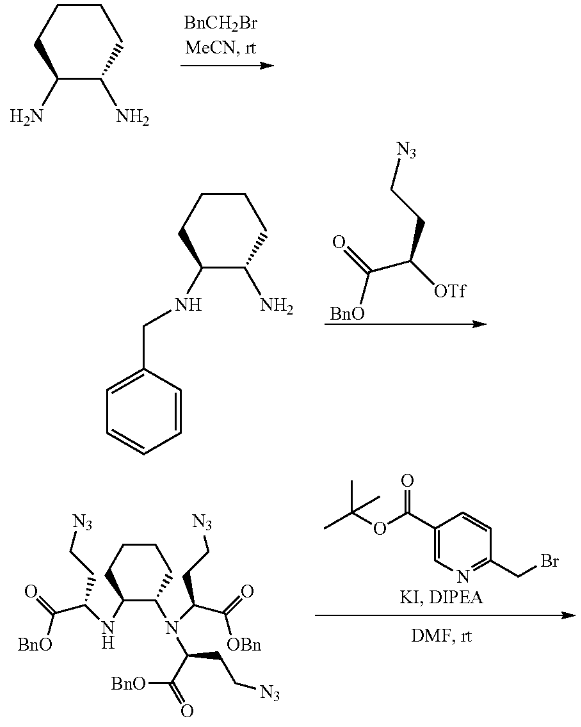

-continued

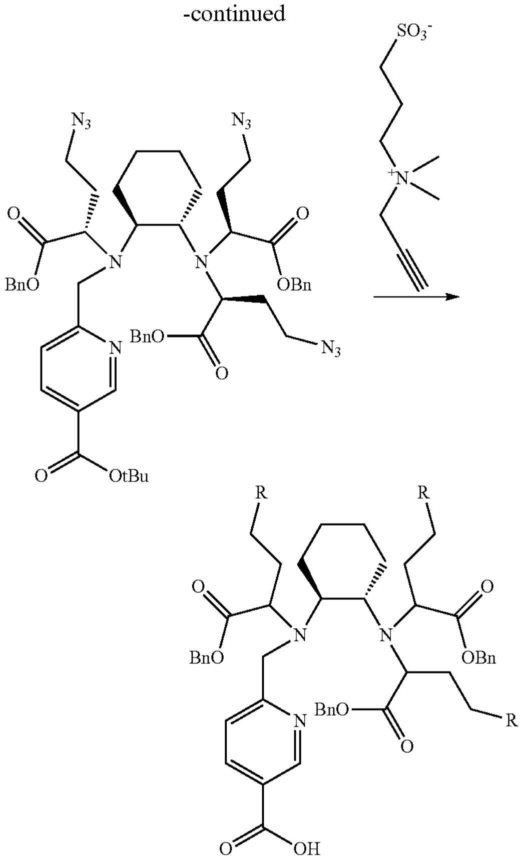

protected $(ZWI)_3$-$PyC_3A$-$CO_2H$

R = 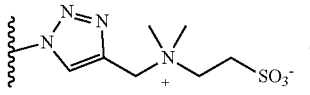 or 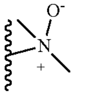

In particular embodiment, the PyC3A-based zwitterionic metal chelators can be complexed with Mn or similar metals.

In still other embodiments, one or more zwitterionic groups of the PyC3A-based zwitterionic metal chelator can be replaced with a targeting vector, such as cRGD, PSMA-617, FAPI, octreotide, bombesin, or corresponding homo- or hetero-dimers provided that PyC3A-based zwitterionic metal chelator remains zwitterionic. In certain embodiments, the targeting ligand includes one or more of LyP-1 peptide having a sequence of CGQKRTRGC (SEQ ID NO: 1) and binding to P32 for diagnosing/treating melanoma; K237 peptide having a sequence of HTMYYHHYQHHL (SEQ ID NO: 2) and binding to VEGFR-2 for diagnosing/treating breast tumor; IL4RPep-1 peptide having a sequence of CRKRLDRNC (SEQ ID NO: 3) and binding to IL4R for diagnosing/treating lung tumor, breast tumor, colon tumor; mUNO peptide having a sequence of CSPGAK (SEQ ID NO: 4) and binding to CD206 for diagnosing/treating breast tumor; folate receptors for diagnosing/treating ovarian and lung cancer; GE11, a dodecapeptide, binding to epidermal growth factor receptor (EGFR or ErbB1) for diagnosing/treating tumors of epithelial origin. Alternatively, the targeting vector can be covalently attached to a reactive linking group of the chelator compound of the invention through standard coupling procedures. For example, the carboxyl or activated carboxyl group of a reactive linking group can react with a nucleophilic functionality on the targeting vector, such as an amine or alcohol derivative, to form an amide or ester linkage. Additional details for the conjugation can be found in WO 2008/017074 and in Frangioni et al. Molecular Imaging, Vol. 1(4), 354-364 (2002), each of which is incorporated herein by reference in its entirety.

It should be apparent to those skilled in the art, that if a targeting vector replaces a zwitterionic group, that zwitterionic group can be restored by adding it to the linker between the zwitterionic metal chelator and the targeting vector. The resulting structures of the conjugates are shown below:

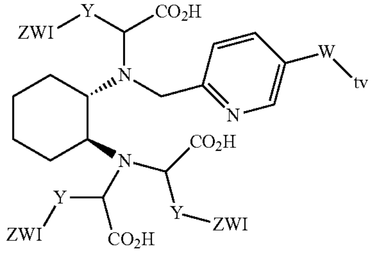

$(ZWI)_4$—$PyC_3A$-tv

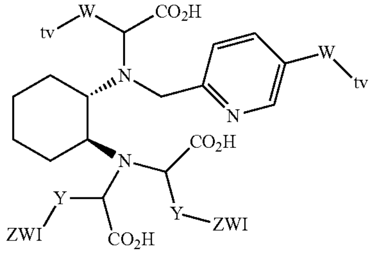

$(ZWI)_4$—$PyC_3A$-$(tv)_2$

V1

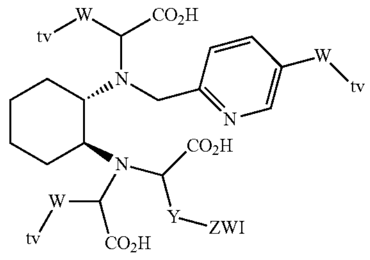

$(ZWI)_4$—$PyC_3A$-$(tv)_3$

V2

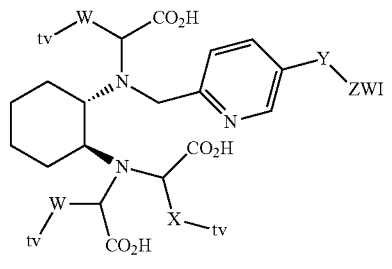

$(ZWI)_4$—$PyC_3A$-$(tv)_3$

The zwitterions ZWI (as defined in FIG. 3) can be separated from the chelator core structure by appropriate spacer moieties Y including alkyl, aryl or heteroaryl groups. The targeting vectors (tv) can be separated from the chelator core structure by appropriate spacer moieties W including alkyl, aryl, heteroaryl, ether, ester, amide, imine and oxime groups. The spacers Y can also contain one or more ether or amide bond or a combination of both and might contain zwitterionic groups added to the sidechains of the spacer moiety.

In certain embodiments, the agent further comprises a PEG-moiety to alter the circulation time in blood. Such moiety can be bound to the conjugate at any suitable structural location as would be understood by one of ordinary skill in the synthesis of such compounds.

Macropa-Based Zwitterionic Metal Chelators

In one aspect, the invention provides a zwitterionic metal chelator based on macropa. Such zwitterionic metal chelators include the following:

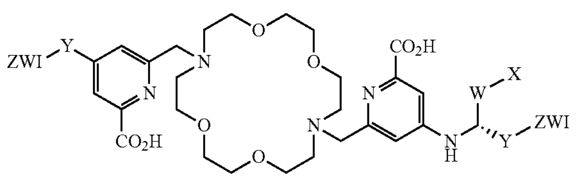

$(ZWI)_2$-macropa-X

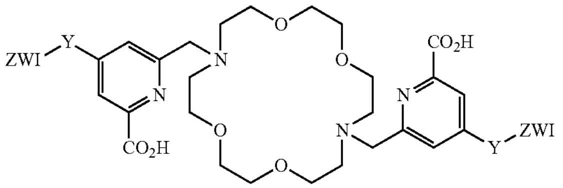

$(ZWI)_2$-macropa

V1

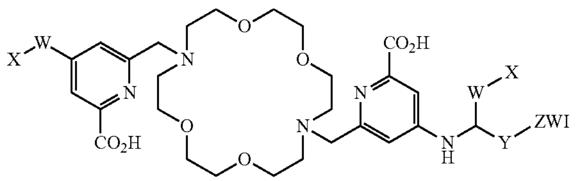

ZWI-macropa-$X_2$

-continued

V2

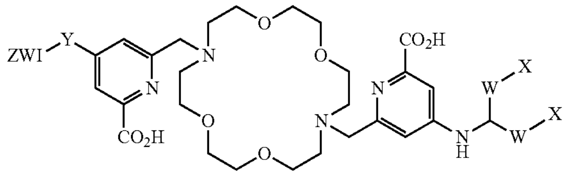

ZWI-macropa-$X_2$

In such embodiments, a macropa-based zwitterionic metal chelator includes 1 or 2 zwitterionic groups as defined in FIG. 3 and 1 or 2 reactive groups X for conjugation to targeting vectors or other molecules or materials. This reactive group can be a carboxylic acid, an activated derivative of a carboxylic acid, such as an NHS ester, a sulfo-NHS ester, a PFP ester, a HOBt ester, a HOAt ester, a TFP ester, an acid anhydride, an acid azide or an acid halide. The reactive group X can also be an amine, azide, alkyne, alkene, ketone, aldehyde, alcohol, phenol, maleimide, thiol, phosphane or a tetrazine. The zwitterionic groups ZWI and the reactive groups X can be separated from the chelator core structure by appropriate spacer moieties W and Y including alkyl, aryl or heteroaryl groups. In certain embodiments, each of W and Y may independently be absent.

In particular embodiments, the macropa-based zwitterionic metal chelator has the formula:

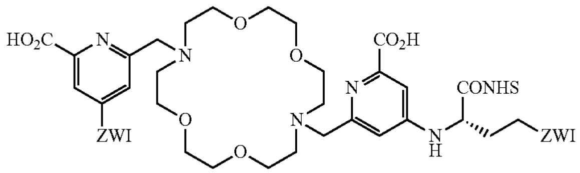

wherein ZWI represents a zwitterionic group. In certain embodiments, ZWI represents an ammonium sulfobetaine group.

Macropa-based zwitterionic metal chelators can be synthesized using the protocol described in Scheme 4.

Scheme 4

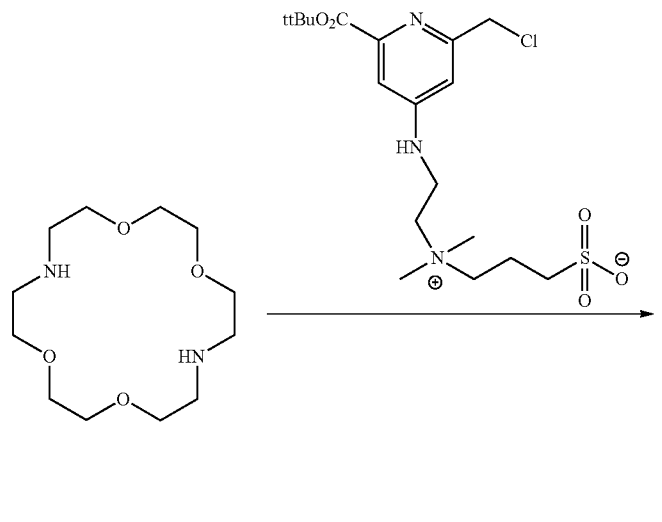

-continued

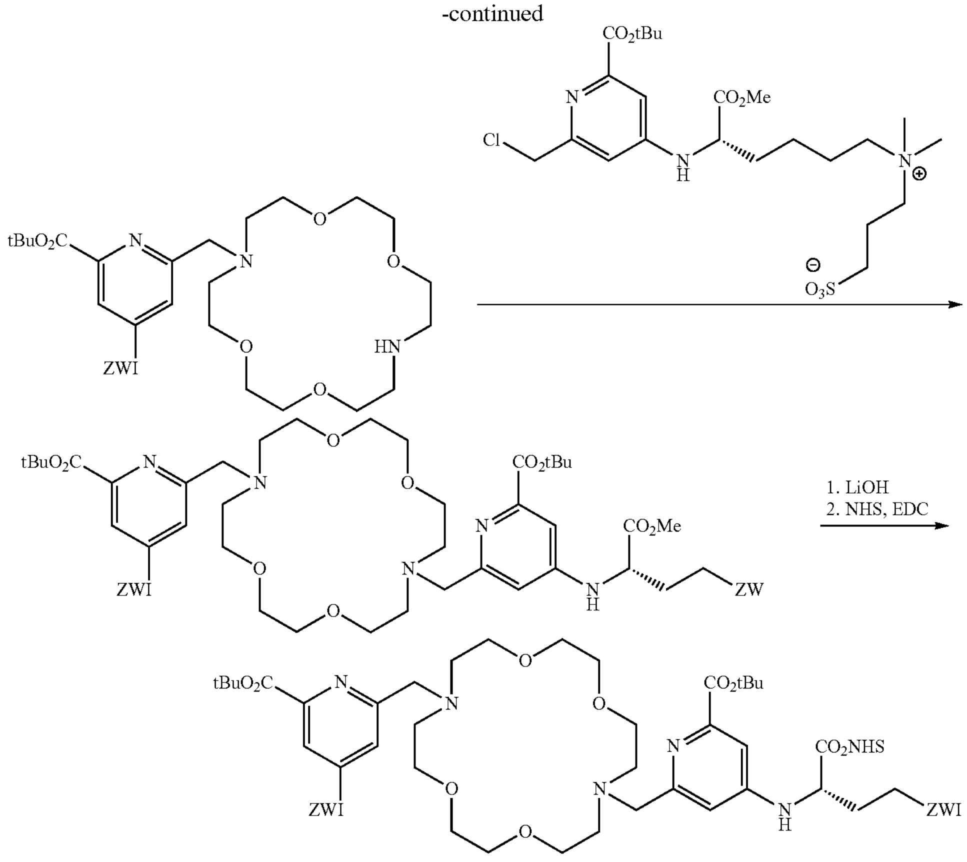

In a particular embodiment, the macropa-based zwitterionic metal chelators can be complexed with $Ac^{3+}$, $Bi^{3+}$, or similar metal cations.

In still other embodiments, one or more zwitterionic groups of the macropa-based zwitterionic metal chelator can be replaced with a targeting vector, such as cRGD, dPSMA-617, KUE, a FAP-targeting small molecule, octreotide, bombesin, or their corresponding homo- or heterodimers, provided that macropa-based zwitterionic metal chelator remains zwitterionic. In certain embodiments, the targeting ligand includes one or more of LyP-1 peptide having a sequence of CGQKRTRGC (SEQ ID NO: 1) and binding to P32 for diagnosing/treating melanoma; K237 peptide having a sequence of HTMYYHHYQHHL(SEQ ID NO: 2) and binding to VEGFR-2 for diagnosing/treating breast tumor; IL4RPep-1 peptide having a sequence of CRKRLDRNC (SEQ ID NO: 3) and binding to IL4R for diagnosing/treating lung tumor, breast tumor, colon tumor; mUNO peptide having a sequence of CSPGAK (SEQ ID NO: 4) and binding to CD206 for diagnosing/treating breast tumor; folate receptors for diagnosing/treating ovarian and lung cancer; GE11, a dodecapeptide, binding to epidermal growth factor receptor (EGFR or ErbB1) for diagnosing/treating tumors of epithelial origin. Alternatively, the targeting vector can be covalently attached to a reactive linking group of the chelator compound of the invention through standard coupling procedures. For example, the carboxyl or activated carboxyl group of a reactive linking group can react with a nucleophilic functionality on the targeting vector, such as an amine or alcohol derivative, to form an amide or ester linkage. Additional details for the conjugation can be found in WO 2008/017074 and in Frangioni et al. Molecular Imaging, Vol. 1(4), 354-364 (2002), each of which is incorporated herein by reference in its entirety.

It should be apparent to those skilled in the art, that if a targeting vector replaces a zwitterionic group, that zwitterionic group can be restored by adding it to the linker between the zwitterionic metal chelator and the targeting vector. The resulting structures of the conjugates are shown in FIG. 7. The zwitterions ZWI (as defined in FIG. 3) can be separated from the chelator core structure by appropriate spacer moieties Y including alkyl, aryl or heteroaryl groups. The targeting vectors (tv) can be separated from the chelator core structure by appropriate spacer moieties W including alkyl, aryl, heteroaryl, ether, ester, amide, imine and oxime groups. The spacers Y can also contain one or more ether or amide bond or a combination of both and might contain zwitterionic groups added to the sidechains of the spacer moiety. In certain embodiments, each of W and Y may independently be absent.

Conjugates of macropa-based zwitterionic chelators and targeting vectors (tv) include, but are not limited to:

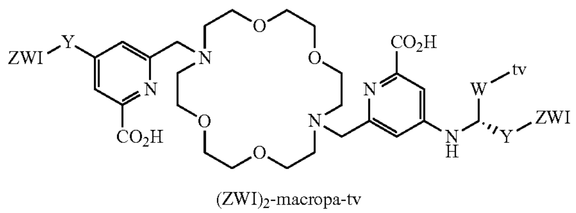

$(ZWI)_2$-macropa-tv

-continued

V1

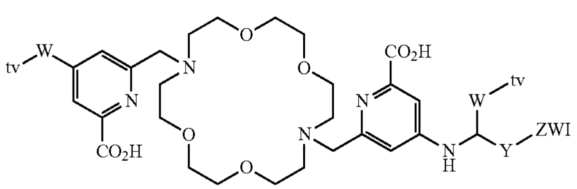

ZWI-macropa-tv$_2$

V2

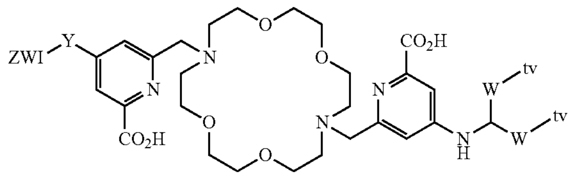

ZWI-macropa-tv$_2$

In certain embodiments, the agent further comprises a PEG-moiety to alter the circulation time in blood. Such moiety can be bound to the conjugate at any suitable structural location as would be understood by one of ordinary skill in the synthesis of such compounds.

Porphyrin-Based Zwitterionic Metal Chelators

In one aspect, the invention provides a zwitterionic metal chelator based on porphyrin. Such zwitterionic metal chelators include the following:

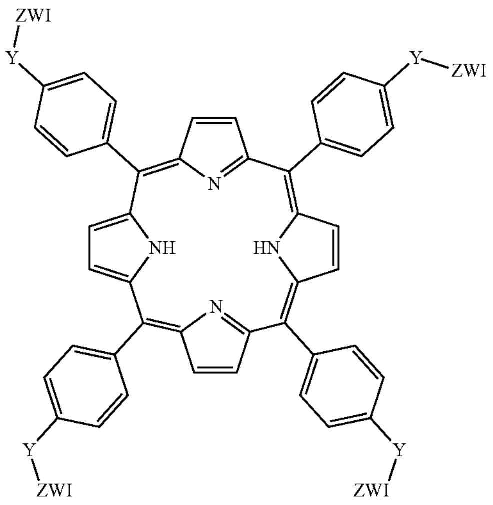

(ZWI)$_4$-porphyrin

-continued

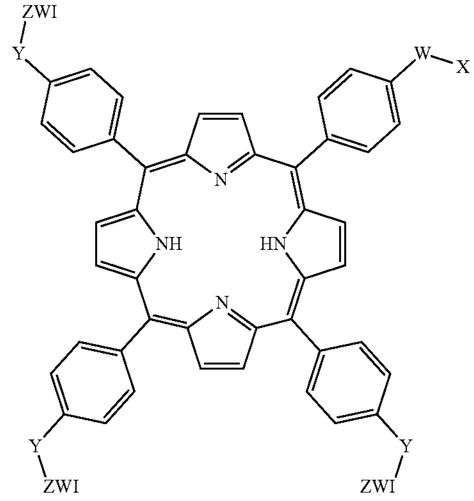

(ZWI)$_3$-porphyrin-X

V1

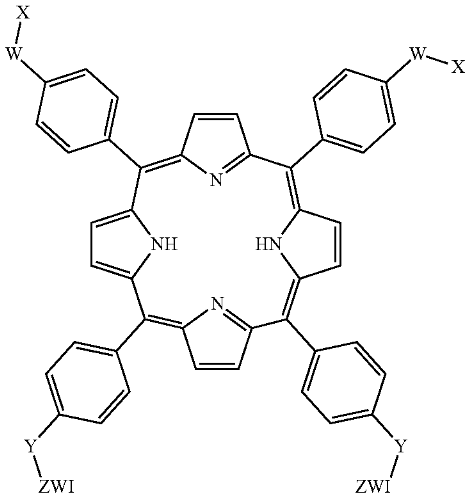

(ZWI)$_2$-porphyrin-X$_2$

V2

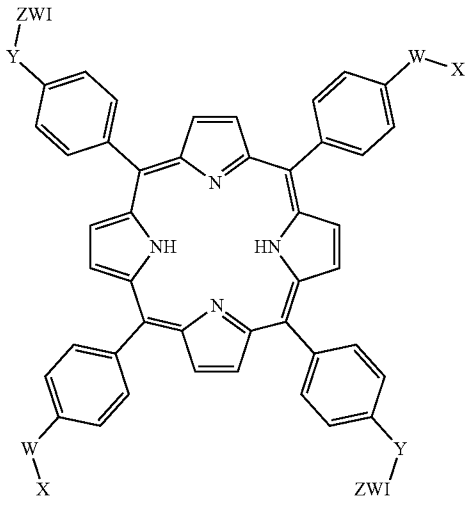

(ZWI)$_2$-porphyrin-X$_2$

-continued

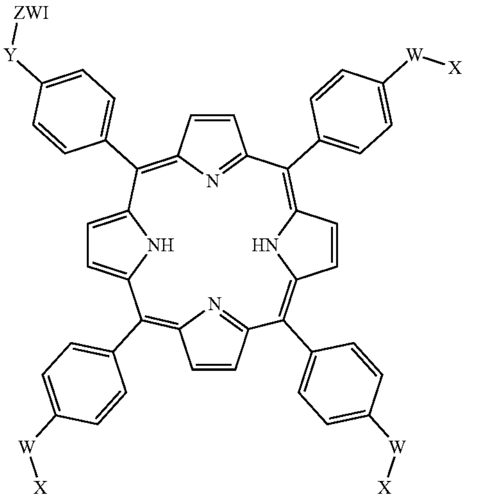

ZWI-porphyrin-$X_3$

In such embodiments, a porphyrin-based zwitterionic metal chelator includes 1, 2, 3, or 4 zwitterionic groups as defined in FIG. 3 and 1 or 2 reactive groups X for conjugation to targeting vectors or other molecules or materials. This reactive group can be a carboxylic acid, an activated derivative of a carboxylic acid, such as an NHS ester, a sulfo-NHS ester, a PFP ester, a HOBt ester, a HOAt ester, a TFP ester, an acid anhydride, an acid azide or an acid halide. The reactive group X can also be an amine, azide, alkyne, alkene, ketone, aldehyde, alcohol, phenol, maleimide, thiol, phosphane or a tetrazine. The zwitterionic groups ZWI and the reactive groups X can be separated from the chelator core structure by appropriate spacer moieties W and Y including alkyl, aryl or heteroaryl groups. In certain embodiments, each of W and Y may independently be absent. In particular embodiments, the porphyrin-based zwitterionic metal chelator includes 4 zwitterionic groups. In certain embodiments, ZWI represents an ammonium sulfobetaine group.

In certain embodiments, the chelator comprises a reactive linking group, typically an activated derivative of a carboxylic acid, such as an NHS ester, a sulfo-NHS ester, a PFP ester, a HOBt ester, a HOAt ester, a TFP ester, an acid anhydride, an acid azide or an acid halide. Such reactive linking groups can be bound or substituted onto the chelator at any suitable structural location as would be understood by one of ordinary skill in the synthesis of such compounds.

In particular embodiments, the porphyrin-based zwitterionic metal chelator has the formula:

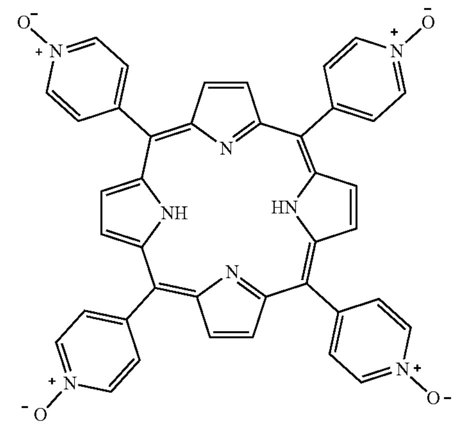

$(NOx)_4$-porphyrin

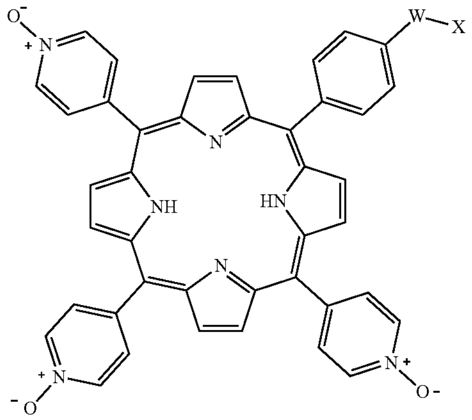

$(NOx)_3$-porphyrin-X

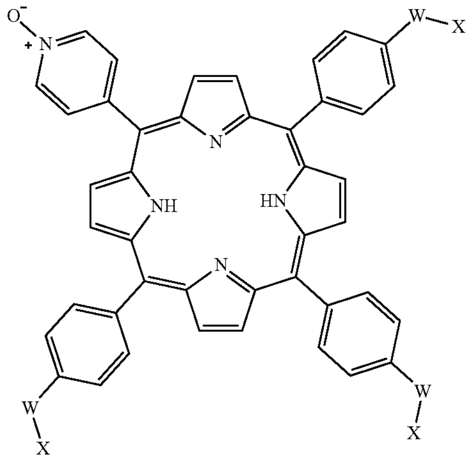

NOx-porphyrin-$X_3$ wherein the zwitterion is a pyridine-N-oxide (as drawn above) or an aromatic N-oxide derived from imidazole, pyrimidine or a similar heteroaromatic residue. X is a reactive group for conjugation to targeting vectors or other molecules or materials. This reactive group can be a carboxylic acid, an activated derivative of a carboxylic acid, such as an NHS ester, a sulfo-NHS ester, a PFP ester, a HOBt ester, a HOAt ester, a TFP ester, an acid anhydride, an acid azide or an acid halide.

The reactive group X can also be an amine, azide, alkyne, alkene, ketone, aldehyde, alcohol, phenol, maleimide, thiol, phosphane or a tetrazine. The reactive group X can be separated from the chelator core structure by appropriate spacer moieties W including alkyl, aryl or heteroaryl groups. In certain embodiments, each of W and Y may independently be absent.

Porphyrin-based zwitterionic metal chelators can be synthesized using the protocol described in Scheme 5.

Scheme 5

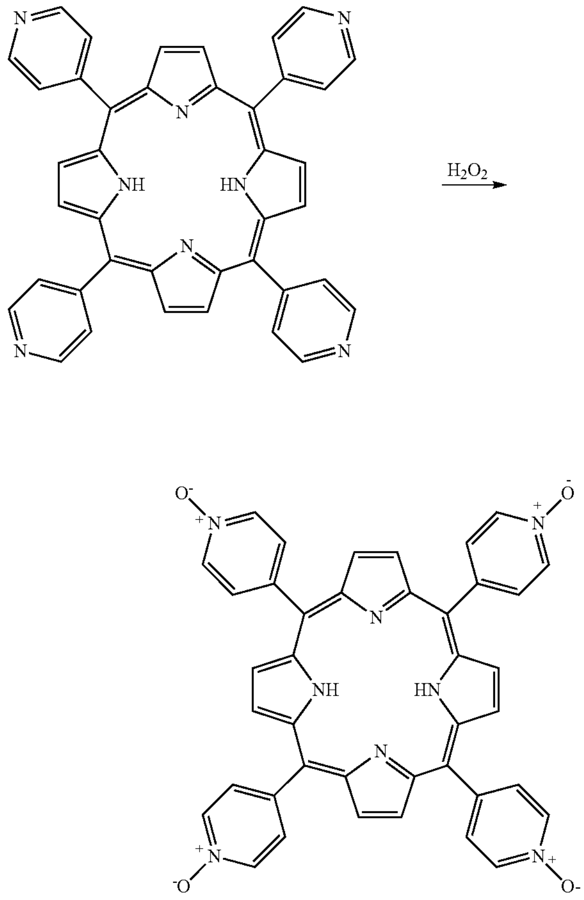

$(NOx)_4$-porphyrin

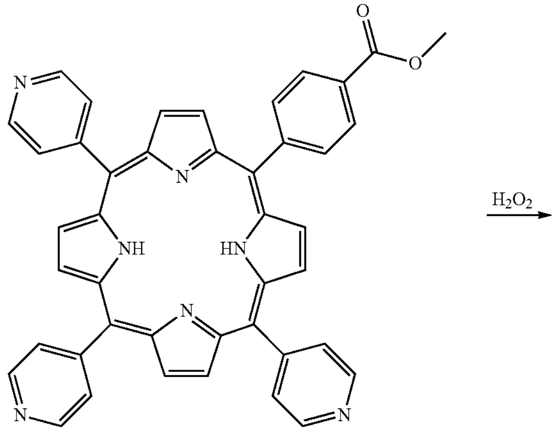

-continued

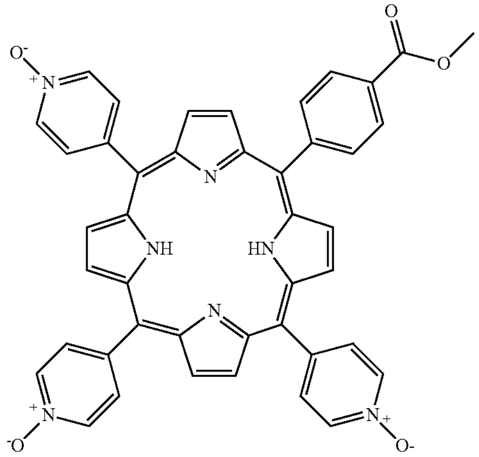

$(NOx)_3$-porphyrin-$CO_2Me$

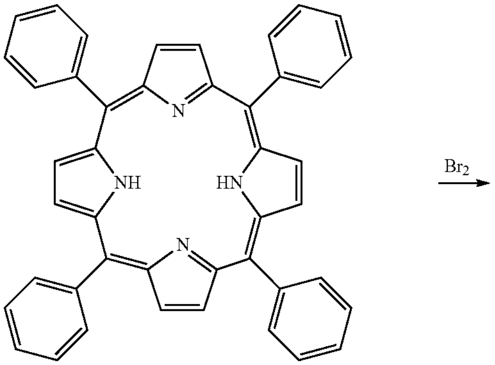

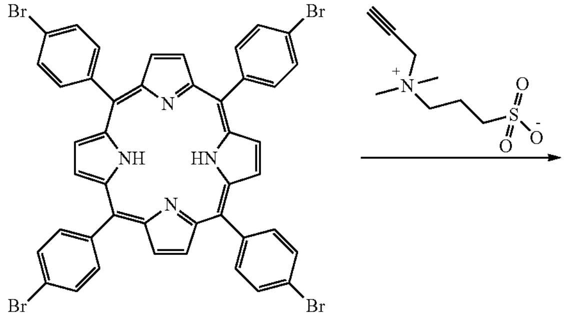

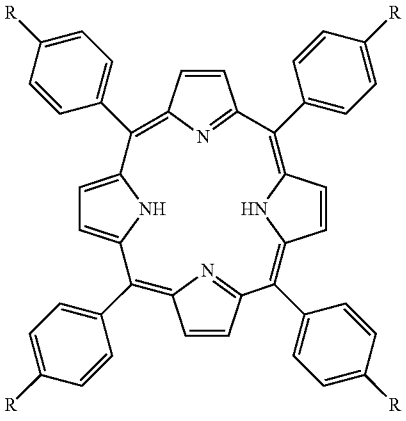

$(ZWI)_4$-prophyrin

-continued

R =

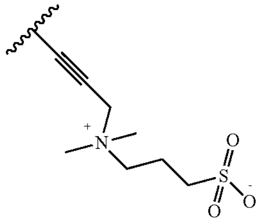

In a particular embodiment, the porphyrin-based zwitterionic metal chelators can be complexed with $Mn^{2+}$, $Mn^{3+}$, $Fe^{2+}$, $Fe^{3+}$, $Gd^{3+}$, $Ac^{3+}$, $Bi^{3+}$, or similar metal cations.

In still other embodiments, one or more zwitterionic groups of the porphyrin-based zwitterionic metal chelator can be replaced with a targeting vector, such as cRGD, dPSMA-617, KUE, a FAP-targeting small molecule, octreotide, bombesin, or their corresponding homo- or heterodimers, provided that porphyrin-based zwitterionic metal chelator remains zwitterionic. In certain embodiments, the targeting ligand includes one or more of LyP-1 peptide having a sequence of CGQKRTRGC (SEQ ID NO: 1) and binding to P32 for diagnosing/treating melanoma; K237 peptide having a sequence of HTMYYHHYQHHL (SEQ ID NO: 2) and binding to VEGFR-2 for diagnosing/treating breast tumor; IL4RPep-1 peptide having a sequence of CRKRLDRNC (SEQ ID NO: 3) and binding to IL4R for diagnosing/treating lung tumor, breast tumor, colon tumor; mUNO peptide having a sequence of CSPGAK (SEQ ID NO: 4) and binding to CD206 for diagnosing/treating breast tumor; folate receptors for diagnosing/treating ovarian and lung cancer; GE11, a dodecapeptide, binding to epidermal growth factor receptor (EGFR or ErbB1) for diagnosing/treating tumors of epithelial origin. Alternatively, the targeting vector can be covalently attached to a reactive linking group of the chelator compound of the invention through standard coupling procedures. For example, the carboxyl or activated carboxyl group of a reactive linking group can react with a nucleophilic functionality on the targeting vector, such as an amine or alcohol derivative, to form an amide or ester linkage. Additional details for the conjugation can be found in WO 2008/017074 and in Frangioni et al. Molecular Imaging, Vol. 1(4), 354-364 (2002), each of which is incorporated herein by reference in its entirety.

It should be apparent to those skilled in the art, that if a targeting vector replaces a zwitterionic group, that zwitterionic group can be restored by adding it to the linker between the zwitterionic metal chelator and the targeting vector. The resulting structures of the conjugates are shown in FIG. 8. The zwitterions ZWI (as defined in FIG. 3) can be separated from the chelator core structure by appropriate spacer moieties Y including alkyl, aryl or heteroaryl groups. The targeting vectors (tv) can be separated from the chelator core structure by appropriate spacer moieties W including alkyl, aryl, heteroaryl, ether, ester, amide, imine and oxime groups. The spacers Y can also contain one or more ether or amide bond or a combination of both and might contain zwitterionic groups added to the sidechains of the spacer moiety. In certain embodiments, each of W and Y may independently be absent.

Conjugates of porphyrin-based zwitterionic chelators and targeting vectors (tv) include, but are not limited to:

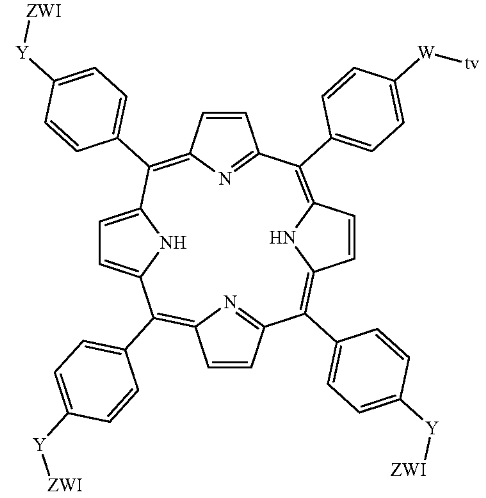

$(ZWI)_3$-porphyrin-tv

V1

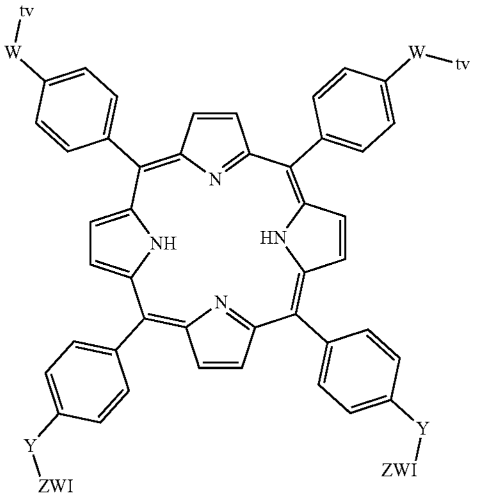

$(ZWI)_2$-porphyrin-$(tv)_2$

V2

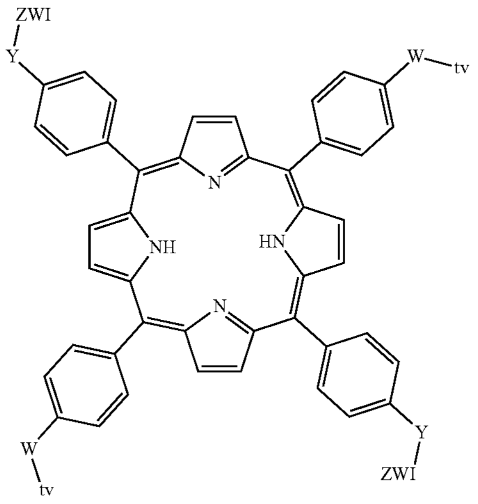

$(ZWI)_2$-porphyrin-$(tv)_2$

-continued

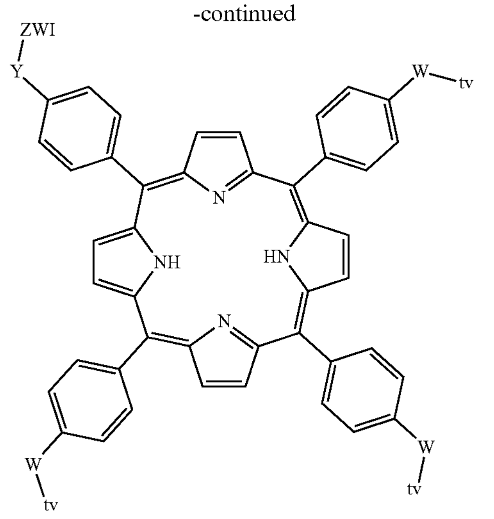

ZWI-porphyrin-(tv)$_3$

In certain embodiments, the porphyrin-based zwitterionic metal chelator has the formula:

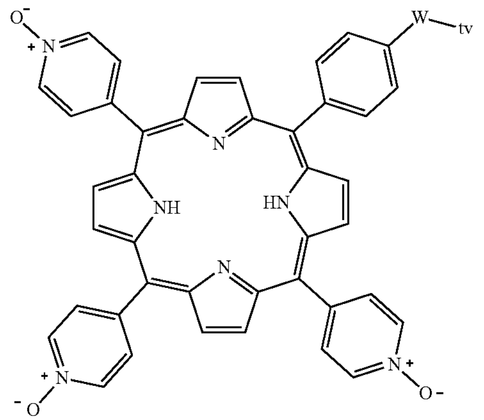

(NOx)$_3$-porphyrin-tv

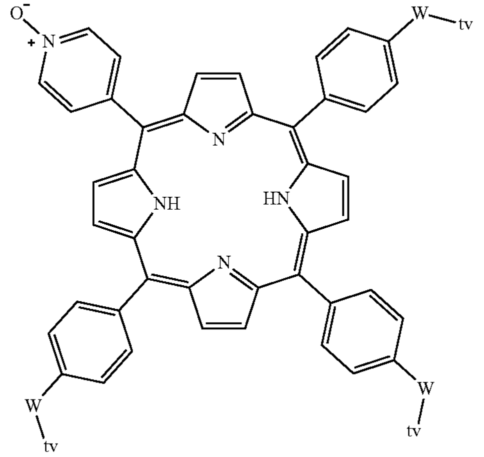

NOx-porphyrin-(tv)$_3$ wherein the zwitterion is a pyridine-N-oxide (as drawn above) or an aromatic N-oxide derived from imidazole, pyrimidine or a similar heteroaromatic residue.

In certain embodiments, the agent further comprises a PEG-moiety to alter the circulation time in blood. Such moiety can be bound to the conjugate at any suitable structural location as would be understood by one of ordinary skill in the synthesis of such compounds.

NOTA-Based Zwitterionic Metal Chelators

In one aspect, the invention provides a zwitterionic metal chelator based on NOTA. Such zwitterionic metal chelators include the following:

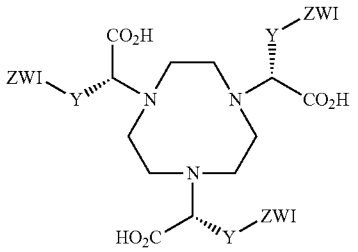

(ZWI)$_3$-NOTA

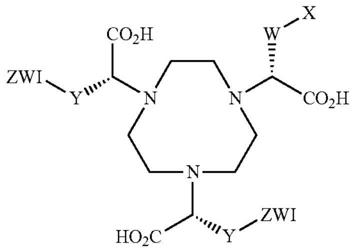

(ZWI)$_2$-NOTA-X

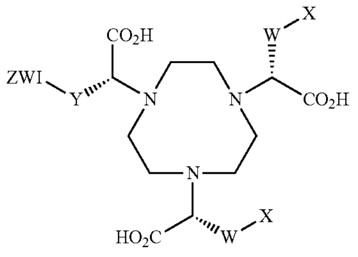

ZWI-NOTA-X$_2$

In such embodiments, a NOTA-based zwitterionic metal chelator includes 1, 2 or 3 zwitterionic groups. In particular embodiments, the NOTA-based zwitterionic metal chelator includes 2 zwitterionic groups as defined in FIG. 3 and 1 or 2 reactive groups X for conjugation to targeting vectors or other molecules or materials. This reactive group can be a carboxylic acid, an activated derivative of a carboxylic acid, such as an NHS ester, a sulfo-NHS ester, a PFP ester, a HOBt ester, a HOAt ester, a TFP ester, an acid anhydride, an acid azide or an acid halide. The reactive group X can also be an amine, azide, alkyne, alkene, ketone, aldehyde, alcohol, phenol, maleimide, thiol, phosphane or a tetrazine. The zwitterionic groups ZWI and the reactive groups X can be separated from the chelator core structure by appropriate spacer moieties W and Y including alkyl, aryl or heteroaryl groups. In certain embodiments, each of W and Y may independently be absent.

In particular embodiments, the NOTA-based zwitterionic metal chelator has the formula:

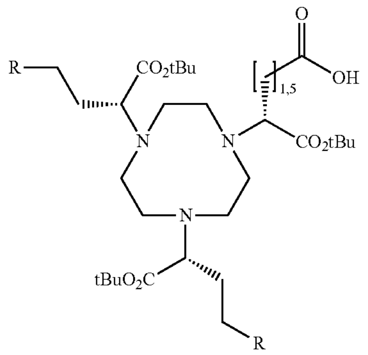

protected $(ZWI)_2$-NOTA-$CO_2H$

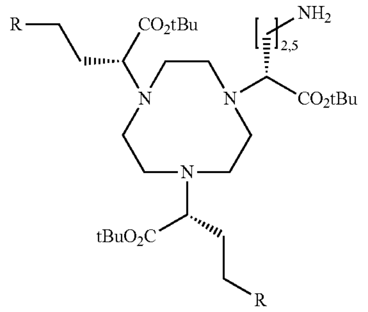

protected $(ZWI)_2$-NOTA-$NH_2$

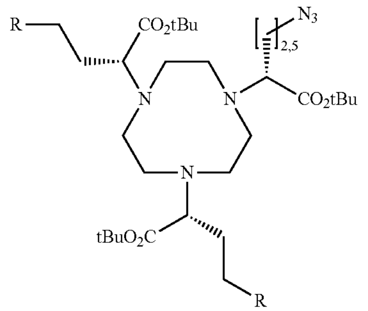

protected $(ZWI)_2$-NOTA-$N_3$

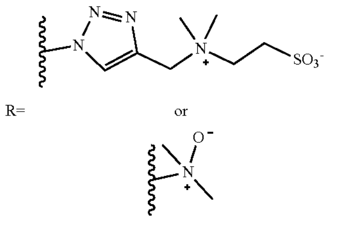

Such NOTA-based zwitterionic metal chelators can be synthesized using the protocol described in Scheme 6.

Scheme 6

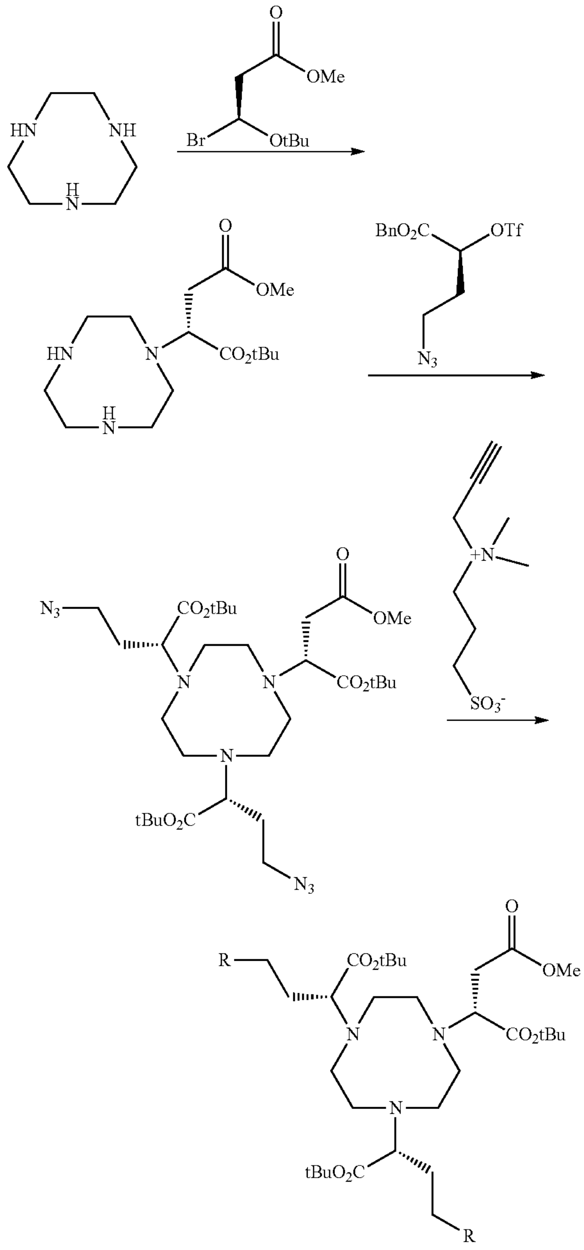

protected $(ZWI)_2$-NOTA-$CO_2Me$

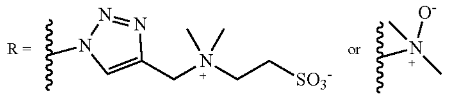

In a particular embodiment, the NOTA-based zwitterionic metal chelators can be complexed with $Ga^{3+}$, $Cu^{2+}$, $Gd^{3+}$, $Ac^{3+}$, $Bi^{3+}$, or similar metal cations.

In still other embodiments, one or more zwitterionic groups of the NOTA-based zwitterionic metal chelator can be replaced with a targeting vector, such as cRGD, dPSMA-617, KUE, a FAP-targeting small molecule, octreotide, bombesin, or their corresponding homo- and heterodimers, provided that NOTA-based zwitterionic metal chelator remains zwitterionic. In certain embodiments, the targeting ligand includes one or more of LyP-1 peptide having a sequence of CGQKRTRGC (SEQ ID NO: 1) and binding to P32 for diagnosing/treating melanoma; K237 peptide having a sequence of HTMYYHHYQHHL(SEQ ID NO: 2) and binding to VEGFR-2 for diagnosing/treating breast tumor; IL4RPep-1 peptide having a sequence of CRKRLDRNC (SEQ ID NO: 3) and binding to IL4R for diagnosing/treating lung tumor, breast tumor, colon tumor; mUNO peptide having a sequence of CSPGAK (SEQ ID NO: 4) and binding to CD206 for diagnosing/treating breast tumor; folate receptors for diagnosing/treating ovarian and lung cancer; GE11, a dodecapeptide, binding to epidermal growth factor receptor (EGFR or ErbB1) for diagnosing/treating tumors of epithelial origin. Alternatively, the targeting vector can be covalently attached to a reactive linking group of the chelator compound of the invention through standard coupling procedures. For example, the carboxyl or activated carboxyl group of a reactive linking group can react with a nucleophilic functionality on the targeting vector, such as an amine or alkoxy derivative, to form an amide or ester linkage. Additional details for the conjugation can be found in WO 2008/017074 and in Frangioni et al. Molecular Imaging, Vol. 1(4), 354-364 (2002), each of which is incorporated herein by reference in its entirety.

It should be apparent to those skilled in the art, that if a targeting vector replaces a zwitterionic group, that zwitterionic group can be restored by adding it to the linker between the zwitterionic metal chelator and the targeting vector. The resulting structures of the conjugates are shown in FIG. 9. The zwitterions ZWI (as defined in FIG. 3) can be separated from the chelator core structure by appropriate spacer moieties Y including alkyl, aryl or heteroaryl groups. The targeting vectors (tv) can be separated from the chelator core structure by appropriate spacer moieties W including alkyl, aryl, heteroaryl, ether, ester, amide, imine and oxime groups. The spacers Y can also contain one or more ether or amide bond or a combination of both and might contain zwitterionic groups added to the sidechains of the spacer moiety. In certain embodiments, each of W and Y may independently be absent.

Conjugates of NOTA-based zwitterionic chelators and targeting vectors (tv) include, but are not limited to:

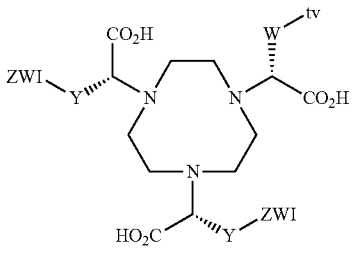

$(ZWI)_2$-NOTA-tv

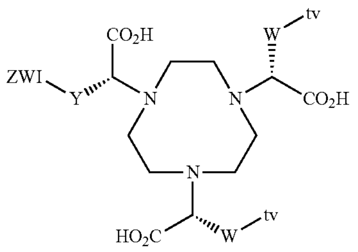

$(ZWI)_2$-NOTA-$(tv)_2$

In certain embodiments, the agent further comprises a PEG-moiety to alter the circulation time in blood. Such moiety can be bound to the conjugate at any suitable structural location as would be understood by one of ordinary skill in the synthesis of such compounds.

Deferoxamine-Based Zwitterionic Metal Chelators

In one aspect, the invention provides a zwitterionic metal chelator based on deferoxamine. Such zwitterionic metal chelators include the following:

VI

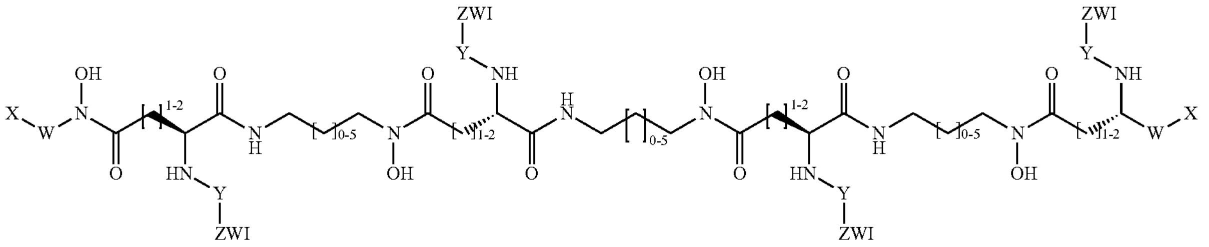

$(ZWI)_4$-DFO*-$X_2$

VIa

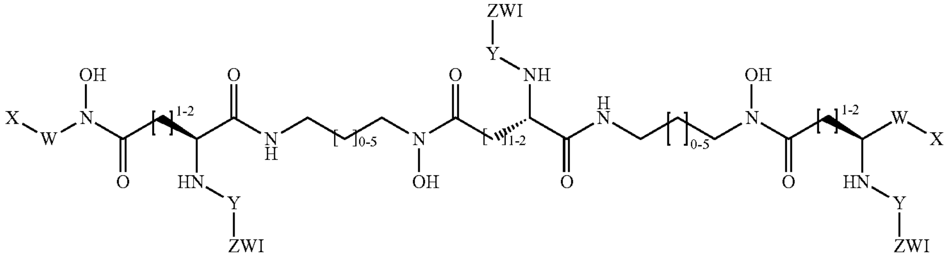

$(ZWI)_3$-DFO-$X_2$

-continued
V1b
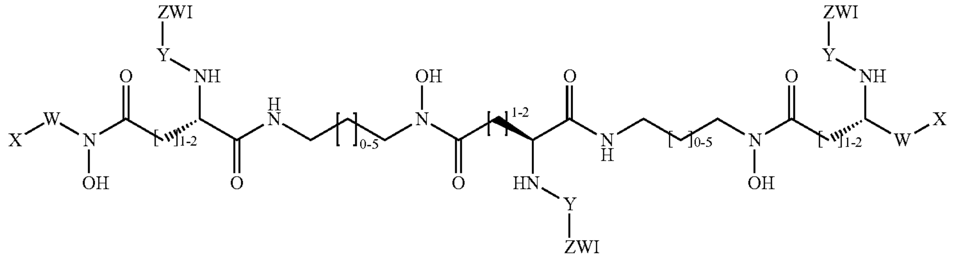
$(ZWI)_3$-DFO-$X_2$
V2
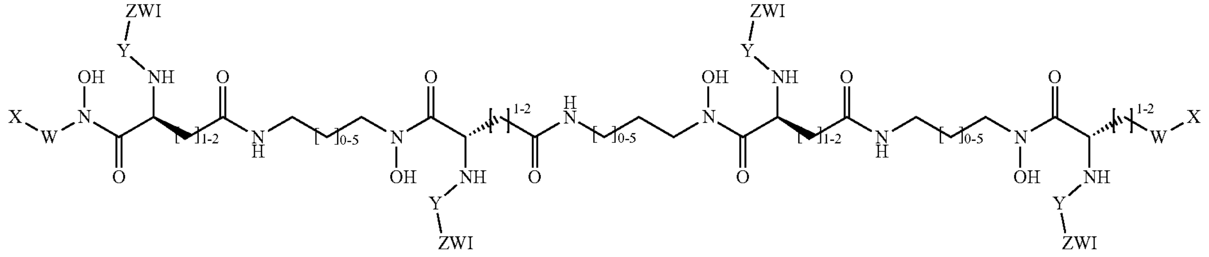
$(ZWI)_4$-DFO*-$X_2$
V2a
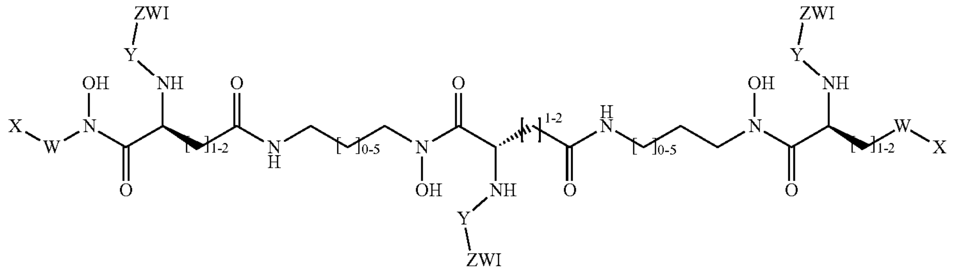
$(ZWI)_3$-DFO-$X_2$
V2b
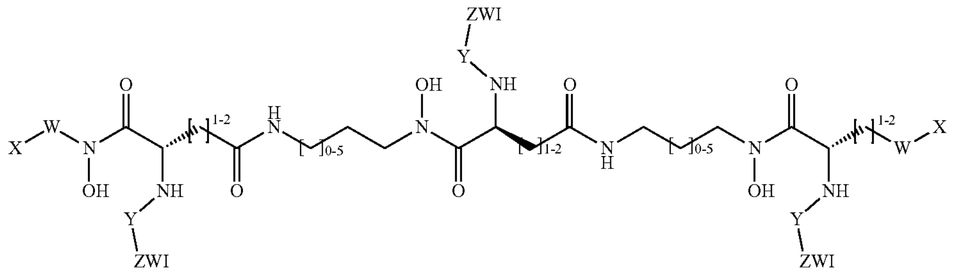
$(ZWI)_3$-DFO-$X_2$
V3
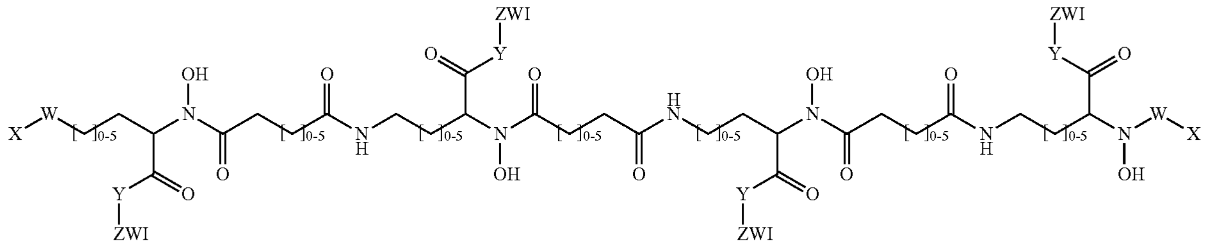
$(ZWI)_4$-DFO*-$X_2$ -continued
V3a
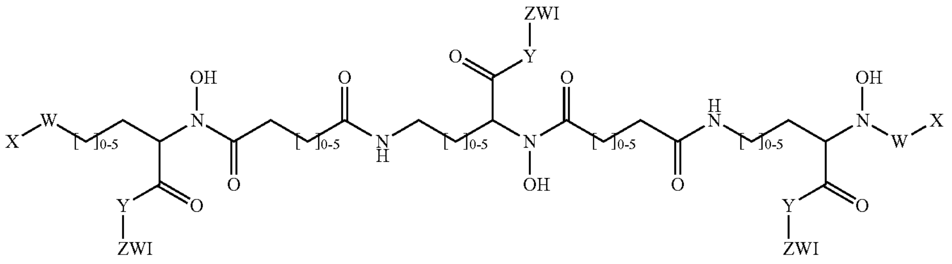
$(ZWI)_3$-DFO-$X_2$
V3b
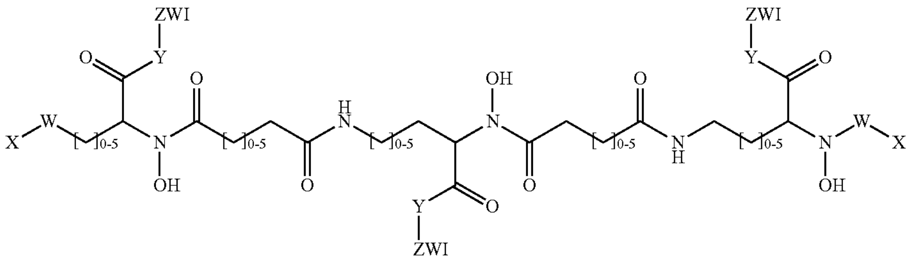
$(ZWI)_3$-DFO-$X_2$
V4
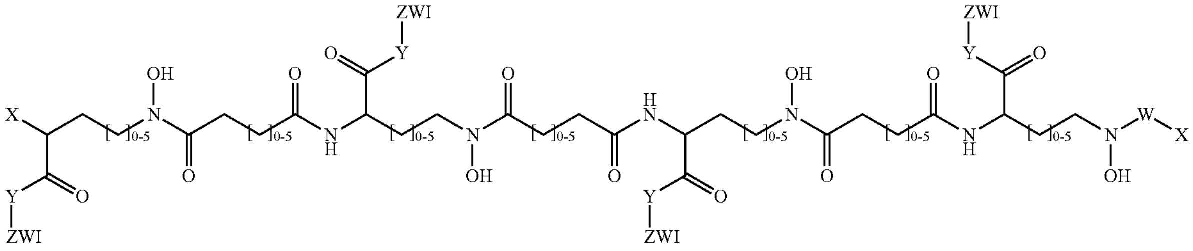
$(ZWI)_4$-DFO*-$X_2$
V4a
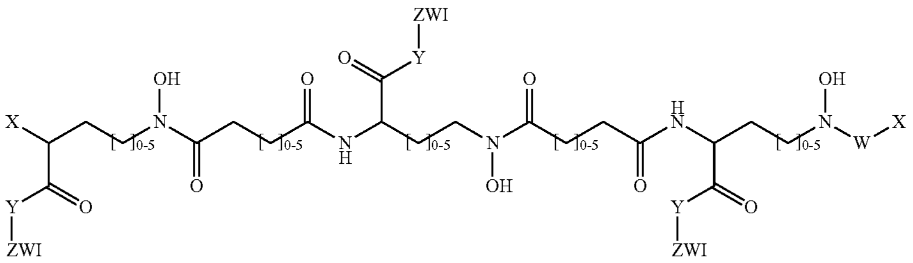
$(ZWI)_3$-DFO-$X_2$
V4b
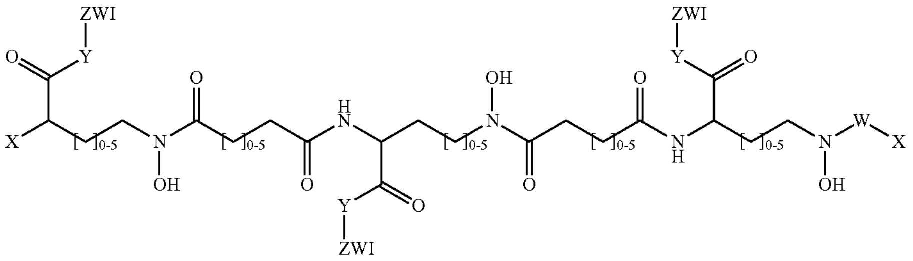
$(ZWI)_3$-DFO-$X_2$ In such embodiments, a deferoxamine-based zwitterionic metal chelator with four hydroxamate groups is derived from DFO* and one with three hydroxamate groups is derived from DFO. A deferoxamine-based zwitterionic metal chelator includes 1, 2, 3 or 4 zwitterionic groups as defined in FIG. 3 and 1 or 2 reactive groups X for conjugation to targeting vectors or other molecules or materials. This reactive group can be a carboxylic acid, an activated derivative of a carboxylic acid, such as an NHS ester, a sulfo-NHS ester, a PFP ester, a HOBt ester, a HOAt ester, a TFP ester, an acid anhydride, an acid azide or an acid halide. The reactive group X can also be an amine, azide, alkyne, alkene, ketone, aldehyde, alcohol, phenol, maleimide, thiol, phosphane or a tetrazine. The zwitterionic groups ZWI and the reactive groups X can be separated from the chelator core structure by appropriate spacer moieties W and Y including alkyl, aryl or heteroaryl groups. In certain embodiments, each of W and Y may independently be absent. In still other embodiments, W-X can represent a hydrogen or an alkyl group.

In certain embodiments, the chelator comprises a reactive linking group, typically an activated derivative of a carboxylic acid, such as an NHS ester, a sulfo-NHS ester, a PFP ester, a HOBt ester, a HOAt ester, a TFP ester, an acid anhydride, an acid azide or an acid halide. Such reactive linking groups can be bound or substituted onto the chelator at any suitable structural location as would be understood by one of ordinary skill in the synthesis of such compounds.

Figure 6:
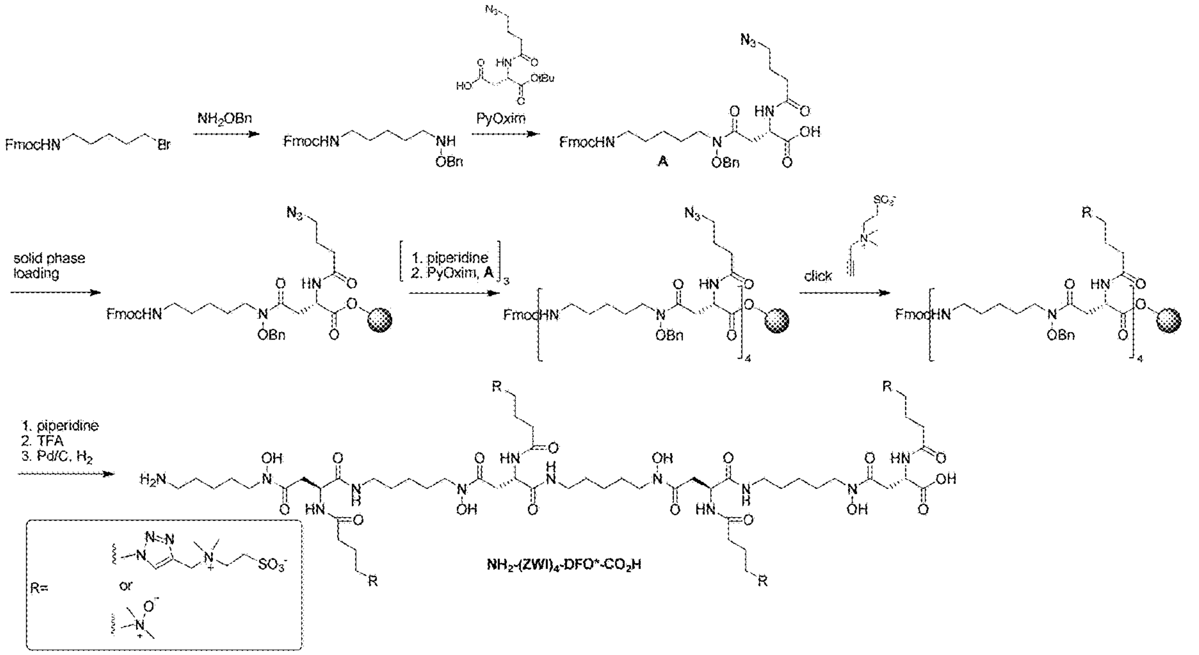
FIG. 6 is a representation of the synthesis of deferoxamine-based zwitterionic conjugates (Scheme 7)

Such deferoxamine-based zwitterionic metal chelators can be synthesized using the protocol described in Scheme 7 (FIG. 6).

In a particular embodiment, the deferoxamine-based zwitterionic metal chelators can be complexed with $Zr^{4+}$, $Fe^{3+}$, $Mn^{2+}$, $Mn^{3+}$, or similar metal cations.

In still other embodiments, the deferoxamine-based zwitterionic metal chelator can be conjugated with a targeting vector, such as cRGD, dPSMA-617, KUE, a FAP-targeting small molecule, octreotide, bombesin, or their corresponding homo- and heterodimers, provided that the deferoxamine-based zwitterionic metal chelator remains zwitterionic. In certain embodiments, the targeting ligand includes one or more of LyP-1 peptide having a sequence of CGQKRTRGC (SEQ ID NO: 1) and binding to P32 for diagnosing/treating melanoma; K237 peptide having a sequence of HTMYYHHYQHHL (SEQ ID NO: 2) and binding to VEGFR-2 for diagnosing/treating breast tumor; IL4RPep-1 peptide having a sequence of CRKRLDRNC (SEQ ID NO: 3) and binding to IL4R for diagnosing/treating lung tumor, breast tumor, colon tumor; mUNO peptide having a sequence of CSPGAK (SEQ ID NO: 4) and binding to CD206 for diagnosing/treating breast tumor; folate receptors for diagnosing/treating ovarian and lung cancer; GE11, a dodecapeptide, binding to epidermal growth factor receptor (EGFR or ErbB1) for diagnosing/treating tumors of epithelial origin. The targeting vector can be covalently attached to a reactive linking group of the chelator compound of the invention through standard coupling procedures. For example, the carboxyl or activated carboxyl group of a reactive linking group can react with a nucleophilic functionality on the targeting vector, such as an amine or alkohol derivative, to form an amide or ester linkage. Additional details for the conjugation can be found in WO 2008/017074 and in Frangioni et al. Molecular Imaging, Vol. 1(4), 354-364 (2002), each of which is incorporated herein by reference in its entirety. On the other hand, other reactive groups X can be used for conjugation of the targeting vector. For example, an amine group can react with an electrophile such as a carboxylic acid, an activated derivative thereof or an isocyanate to form an amide or a urea linkage. The amine might also be converted via other chemical transformations such as nucleophilic substitution or reductive amination to give physiologically stable linkages to the targeting vector. One or two reactive groups at any position of the deferoxamine-based zwitterionic chelator might be used for conjugation of one or more targeting vectors. Two examples of the resulting conjugates are shown in FIG. 10. The zwitterions ZWI (as defined in FIG. 3) can be separated from the chelator core structure by appropriate spacer moieties Y including alkyl, aryl or heteroaryl groups. The targeting vectors (tv) can be separated from the chelator core structure by appropriate spacer moieties W including alkyl, aryl, heteroaryl, ether, ester, amide, imine and oxime groups. The spacers Y can also contain one or more ether or amide bond or a combination of both and might contain zwitterionic groups added to the sidechains of the spacer moiety. In certain embodiments, each of W and Y may independently be absent.

Exemplary conjugates of deferoxamine-based zwitterionic chelators and targeting vectors (tv) include, but are not limited to:

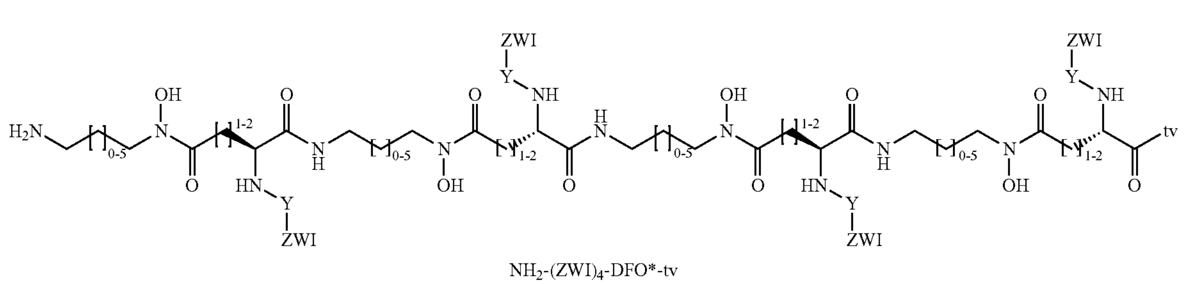

$NH_2$-(ZWI)$_4$-DFO*-tv

-continued

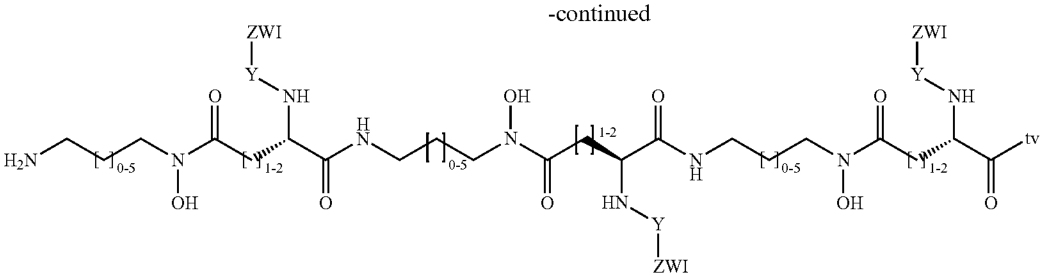

$NH_2$-(ZWI)$_3$-DFO-tv

In certain embodiments, the agent further comprises a PEG-moiety to alter the circulation time in blood. Such moiety can be bound to the conjugate at any suitable structural location as would be understood by one of ordinary skill in the synthesis of such compounds.

Targeting Vectors

In some embodiments of the metal chelators of the invention, one or more zwitterionic groups of the zwitterionic metal chelator can be replaced with a targeting vector, such as cRGD, a PSMA binding vector, such as PSMA-617 or KUE, a FAP-targeting molecule (FAP-inhibitor or FAPI), octreotide, bombesin, or their corresponding homo- and hetero-dimers provided that zwitterionic metal chelator remains zwitterionic.

In certain embodiments of the invention, the targeting ligand according to the invention can be a cyclic-RGD having the following structure:

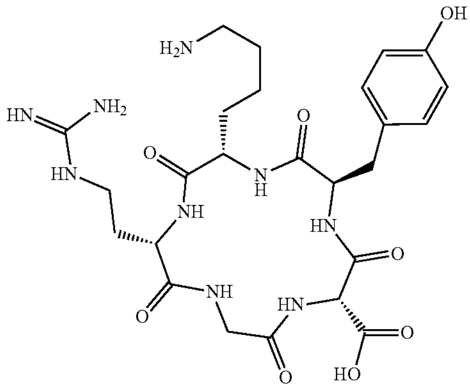

cRGD Peptide Targeting Ligand

In certain embodiments, the FAPI-targeting ligand includes NH2-FAPI-74. Specific details regarding NH2-FAPI-74 are described in: Linder et al., "Radioligands Targeting Fibroblast Activation Protein (FAP)," the entirety of which is incorporated herein by reference. In general, NH2-FAPI-74 has the following structure: the FAPI-targeting ligand includes $NH_2$-FAPI-74

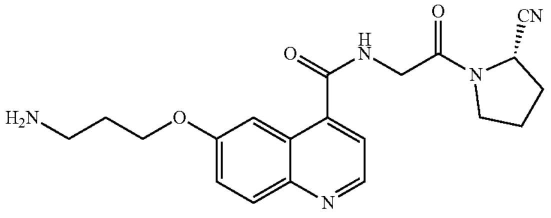

$NH_2$-FAPI-74

In certain embodiments, the targeting ligand includes one or more of LyP-1 peptide having a sequence of CGQKRTRGC (SEQ ID NO: 1) and binding to P32 for diagnosing/treating melanoma; K237 peptide having a sequence of HTMYYHHYQHHL(SEQ ID NO: 2) and binding to VEGFR-2 for diagnosing/treating breast tumor; IL4RPep-1 peptide having a sequence of CRKRLDRNC(SEQ ID NO: 3) and binding to IL4R for diagnosing/treating lung tumor, breast tumor, colon tumor; mUNO peptide having a sequence of CSPGAK (SEQ ID NO: 4) and binding to CD206 for diagnosing/treating breast tumor; folate receptors for diagnosing/treating ovarian and lung cancer; GE11, a dodecapeptide, binding to epidermal growth factor receptor (EGFR or ErbB1) for diagnosing/treating tumors of epithelial origin.

In a particular aspect, the invention provides a zwitterionic metal chelator conjugated to a targeting vector for prostate specific membrane antigen (PSMA). For example, a targeting vector based on (((S)-5-((S)-2-((1r,4S)-4-(aminomethyl)cyclohexane-1-carboxamido)-3-(naphthalen-2-yl)propanamido)-1-carboxypentyl)carbamoyl)-L-glutamic acid, which is a derivative of PSMA-617 or Vipivotide tetraxetan. This PSMA-targeting vector is called dPSMA-617 (for "derivative of PSMA-617) in this disclosure.

An alternative PSMA-targeting vector is (((S)-5-amino-1-carboxypentyl)carbamoyl)-L-glutamic acid (KUE).

Figure 4:
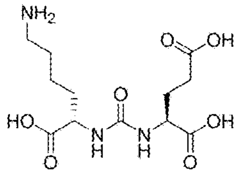
FIG. 4 is a representation of three targeting vectors encompassed by the invention.
Figure 4:
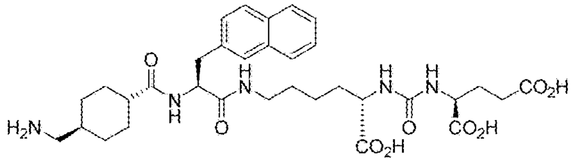
Figure 4:
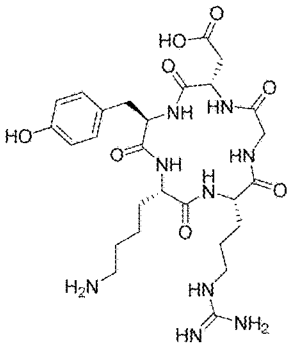

The structures of dPSMA-617 and KUE are shown in FIG. 4.

In such embodiments, a KUE or dPSMA-617-conjugated zwitterionic metal chelator includes 1-4 zwitterionic groups. In particular embodiments, the KUE or dPSMA-617-conjugated zwitterionic metal chelator includes 1-3 zwitterionic groups.

In particular embodiments, the KUE or PSMA-617-conjugated zwitterionic metal chelator has the formula:
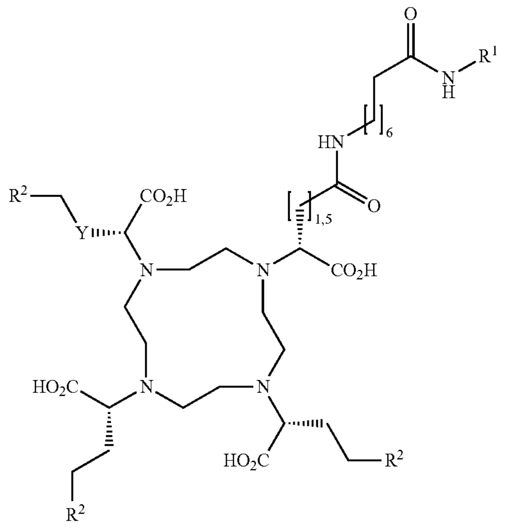
$(ZWI)_3$-DOTA-spacer-$R^1$
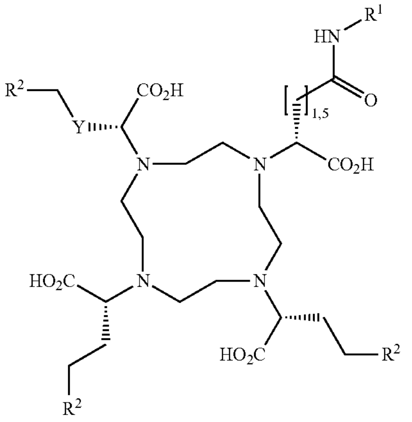
$(ZWI)_3$-DOTA-$R^1$
$R^2$ =
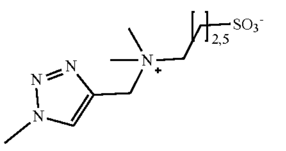
$R^1$ =
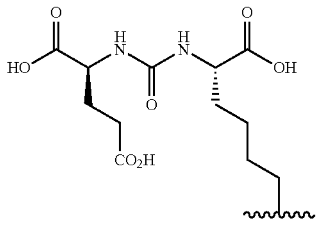
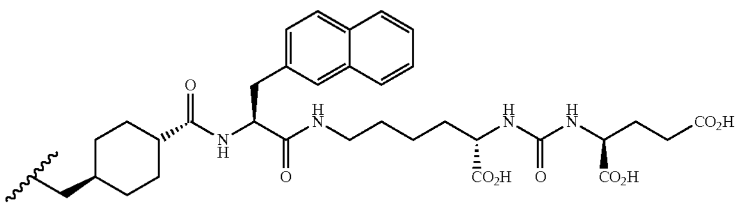
In particular embodiment, the KUE or PSMA-617-conjugated zwitterionic metal chelators can be complexed with $Ga^{3+}$, $Cu^{2+}$, $Lu^{3+}$, $Zr^{4+}$, $Mn^{2+}$, $Mn^{3+}$, $Tb^{3+}$, $Gd^{3+}$, or similar metal cations.

In general, the structure of octreotide (SEQ ID No: 5) is:

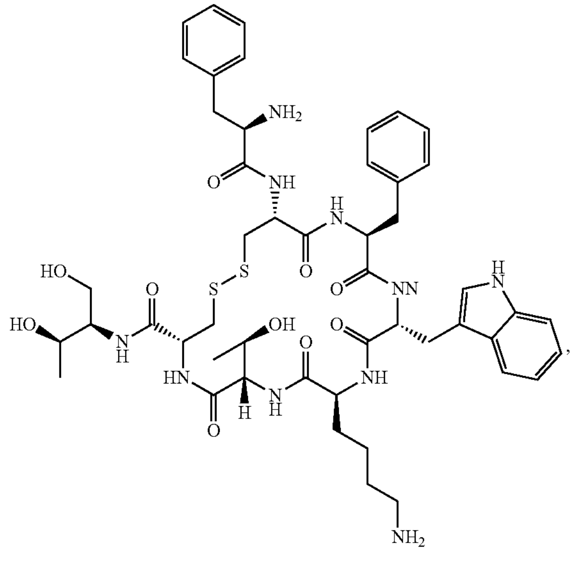

or a derivative thereof.

In general, the structure of bombesin (SEQ ID No: 6) is:

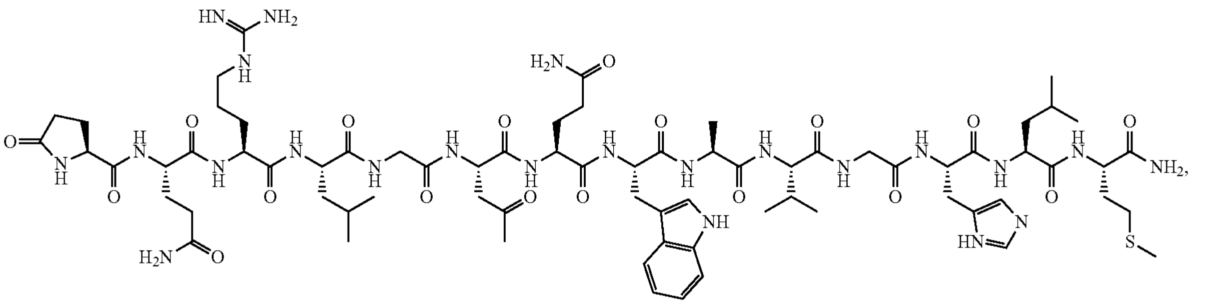 [SMILES: CSCC[C@H](NC(=O)[C@H](CC(C)C)NC(=O)[C@H](Cc1c[nH]cn1)NC(=O)CNC(=O)[C@@H](NC(=O)[C@H](C)NC(=O)[C@H](Cc1c[nH]c2ccccc12)NC(=O)[C@H](CCC(N)=O)NC(=O)[C@H](CC(C)=O)NC(=O)CNC(=O)[C@H](CC(C)C)NC(=O)[C@H](CCCNC(=N)N)NC(=O)[C@H](CCC(N)=O)NC(=O)[C@@H]1CCC(=O)N1)C(C)C)C(N)=O]

or a derivative thereof.

The synthetic protocol described in Scheme 2 can be used to produce conjugated zwitterionic metal chelators based on DOTA, NOTA, porphyrin, deferoxamine and Py3CA using cRGD, a FAP-targeting molecule, octreotide, or dimers including a combination of cRGD, dPSMA-617, a FAP-targeting molecule, octreotide, and bombesin. In certain embodiments, the targeting ligand includes one or more of LyP-1 peptide having a sequence of CGQKRTRGC (SEQ ID NO: 1) and binding to P32 for diagnosing/treating melanoma; K237 peptide having a sequence of HTMYYHHYQHHL(SEQ ID NO: 2) and binding to VEGFR-2 for diagnosing/treating breast tumor; IL4RPep-1 peptide having a sequence of CRKRLDRNC(SEQ ID NO: 3) and binding to IL4R for diagnosing/treating lung tumor, breast tumor, colon tumor; mUNO peptide having a sequence of CSPGAK (SEQ ID NO: 4) and binding to CD206 for diagnosing/treating breast tumor; folate receptors for diagnosing/treating ovarian and lung cancer; GE11, a dodecapeptide, binding to epidermal growth factor receptor (EGFR or ErbB1) for diagnosing/treating tumors of epithelial origin. Depending on the reactive group of the zwitterionic metal chelator other common chemical methods may be used to conjugate the targeting vector, such as azide-alkyne-cycloadditions, nucleophilic displacements, Diels-Alder-reactions, urea and urethane formations, thiol-ene conjugations or similar conversions. For some of these conversions derivatives of KUE or dPSMA-617 with other reactive functional groups can be used. For example, a conjugation via a copper-catalyzed azide-alkyne-cycloaddition could require either an alkyne or an azide group as the reactive group at the zwitterionic chelator and a matching alkyne or azide group as the reactive group at the targeting vector.

In certain embodiments, the targeting ligand can further include a molecular scaffold moiety to which the binding moiety and other groups can attach. For example, the molecule scaffold can bear one or more of the following: (1) a moiety designed to react with the reactive linking group of the dye to form a covalent bond, (2) a charge balancing moiety, such as any of the ionic groups described herein, and (3) a moiety that binds to the biological target. An example of a molecular scaffold is an adamantane derivative, such as described in U.S. Pat. App. Pub. No. 2006/0063834, which is incorporated herein by reference in its entirety, and illustrates the preparation of a targeting ligand that incorporates an adamantane scaffold. Specifically, the adamantane core holds (1) an amino group capable of reacting with the dye compounds, (2) a charge-balancing moiety that will neutralize a negative charge on the dye molecule, and (3) two moieties that bind to the biological target PSMA. For a description of moieties that bind to PSMA, see, Humblet, V. et al. Mol. Imaging, 2005, 4: 448-62; Misra P. et al. J. Nucl. Med. 2007, 48: 1379-89; Chen, Y., et al. J. Med. Chem, 2008, 51: 7933-43; Chandran, S. S., et al. Cancer Biol. Ther., 2008, 7: 974-82; Banerjee, S. R., J. Med. Chem. 2008, 51: 4504-17; Mease, R. C., et al. Clin. Cancer Res., 2008, 14: 3036-43; Foss, C. A. et al. Clin. Cancer. Res., 2005, 11: 4022-8, each of which is incorporated herein by reference in its entirety.

Imaging Methods

In one aspect, the invention provides for methods of biomedical imaging of tissues or cells in a biological sample. In particular embodiment, the invention encompasses a method for detecting or imaging one or more cancer cells in a biological sample.

In some embodiments, the method is suitable for imaging of abnormal, but not malignant, tissue, such as defects of the musculoskeletal system using FAP as a targeting vector or vascular system using cRGD as a targeting vector.

In some embodiments, the method is suitable for imaging of cancer, tumor or neoplasm. In a further embodiment, the cancer is selected from eye or ocular cancer, rectal cancer, colon cancer, cervical cancer, prostate cancer, breast cancer and bladder cancer, oral cancer, benign and malignant tumors, stomach cancer, liver cancer, pancreatic cancer, lung cancer, corpus uteri, ovary cancer, prostate cancer, testicular cancer, renal cancer, brain/cns cancer (e.g., gliomas), throat cancer, skin melanoma, acute lymphocytic leukemia, acute myelogenous leukemia, Ewing's Sarcoma, Kaposi's Sarcoma, basal cell carinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, lymphoma, neurofibromatosis, tuberous sclerosis, hemangiomas, and lymphangiogenesis.

In some embodiments, the cancer cells are adult solid tumor cells or pediatric solid tumor cells. Non-limiting examples of such cells include melanoma cells, neuroblastoma cells, lung cancer cells, adrenal cancer cells, colon cancer cells, colorectal cancer cells, ovarian cancer cells, prostate cancer cells, liver cancer cells, subcutaneous cancer cells, squamous cell cancer cells, intestinal cancer cells, retinoblastoma cells, cervical cancer cells, glioma cells, breast cancer cells, pancreatic cancer cells, Ewings sarcoma cells, rhabdomyosarcoma cells, osteosarcoma cells, retinoblastoma cells, Wilms' tumor cells, and pediatric brain tumor cells.

In particular embodiments, the cancer cells are prostate cancer cells.

In some embodiments, the biological sample is part or all of a subject. In some embodiments, the biological sample is obtained from a subject.

In particular embodiments, the method includes the steps of (a) contacting the biological sample with one or more of the zwitterionic metal chelators described above, wherein the zwitterionic metal chelator is coordinated to a metal atom capable of being detected by one or more conventional scanning methods.

In some embodiments, the compound is administered by parenteral, intranasal, sublingual, rectal, or transdermal delivery. In some such embodiments, the compound is administered intravenously. In some embodiments, the compound is administered intratumorally.

In some embodiments, the tumor or cell is found in a subject. The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal (non-human) subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. In some embodiments, the subject is human. In other embodiments, the subject is non-human.

In particular embodiments, the subject is a human.

The methods of imaging tissue or cells include the following basic steps:

(a) contacting the tissue or cells with an imaging agent comprising a zwitterionic metal chelator; and
(b) imaging the tissue or cells using positron emission tomography (PET), single-photon emission computerized tomography (SPECT), or magnetic resonance imaging (MRI).

The imaging agent described herein is a substance to that can be used to image tissues or cells, such as those of a living organism, for purposes of diagnosis, therapy, image-guided surgery, and the like. In some embodiments, the organism is a mammal, such as a human.

The imaging agents described herein generally has improved "signal-to-background ratio" (SBR) compared to presently known imaging agents. The improvement in SBR is believed to be a result of improved in vivo properties due to "charge-balancing." SBR is a measure of the intensity of the signal obtained from a target (peak signal) over the measure of the intensity of the signal obtained nearby the target (background signal), the target being the tissues or cells targeted by the imaging agent. SBR measurements can be readily obtained through routine measurement procedures. Higher SBR values are more desirable, resulting in greater resolution of the imaged tissues. In some embodiments, the imaging agents achieve an SBR of at least about 1.1 (i.e., peak signal is at least 10% over background). In further embodiments, the imaging agents achieve an SBR of at least about 1.2, at least about 1.3, at least about 1.4, at least about 1.5, at least about 1.6, at least about 1.7, at least about 1.8, at least about 1.9, or at least about 2.0. In yet further embodiments, the imaging agents achieve an SBR of about 1.1 to about 50, about 1.5 to about 30, about 2.0 to about 20, about 2.0 to about 5.0, or about 5.0 to about 10.

The zwitterionic metal chelators of the invention generally have good solubility in substantially neutral aqueous media, and in particular, blood and blood serum. In some embodiments, the imaging agent has a solubility in 10 mM HEPES solution, pH 7.4, of at least about 10 μM. In further embodiments, the imaging agent has a solubility in 10 mM HEPES solution, pH 7.4, of at least about 15 μM at least about 20 μM, at least about 25 μM, at least about 30 μM, at least about 40 μM, or at least about 50 μM.

The zwitterionic metal chelators of the invention has significant improvements with regard to stability over time, allowing for dramatically improved operability and use for imaging and mapping. Similarly, the stability of the imaging agent allows for increased accuracy during surgery as the signal does not degrade over time. This is particularly important for complexes of Gd that are used as contrast for MRI. It has been established that Gd accumulates for long periods of time due to either instability in its metal chelator and/or inefficient elimination from the body. Zwitterionic metal chelators of Gd solve this problem by maximizing stability of the metal complex while maximizing rapid elimination from the body through renal clearance.

In another aspect, the disclosure encompasses a method of measuring and/or monitoring the effectiveness of various biological functions of a subject. In particular embodiments, the method provides for measuring the effectiveness of hepatic function, renal function, or blood pooling in a subject. In such embodiments, the zwitterionic metal chelators may be used with or without the addition of a targeting vector. The method includes the step of administering to a subject in need of measurement of a biological function with a quantifiable amount of one or more of the zwitterionic metal chelators described above; imaging the subject using positron emission tomography (PET), single-photon emission computerized tomography (SPECT), or magnetic resonance imaging (MRI); and determining the amount of the zwitterionic metal chelator present in the biological function being observed.

Treatment, Diagnosis, and Monitoring Methods

Cancerous Conditions

In another aspect, the disclosure encompasses a method for inhibiting the proliferation or growth of malignant or non-malignant cells. The method includes the step of contacting one or more cells with an effective amount of one or more of the zwitterionic metal chelators described above, wherein the metal atom is a radioactive metal isotope known to emit ionizing radiation in a form that would result in the death of cells that take up the analogs.

Non-limiting examples of metal isotopes that are used include Lu-177, Y-90, Ho-166, Re-186, Re-188, Cu-67, Au-199, Rh-105, Ra-223, Ac-225, As-211, Pb-212, and Th-227.

In some embodiments, the method is performed in vivo, ex vivo, or in vitro.

In some embodiments, the malignant cells are adult solid tumor cells or pediatric solid tumor cells. Non-limiting examples of such cells include melanoma cells, neuroblastoma cells, lung cancer cells, adrenal cancer cells, colon cancer cells, colorectal cancer cells, ovarian cancer cells, prostate cancer cells, liver cancer cells, subcutaneous cancer cells, squamous cell cancer cells, intestinal cancer cells, retinoblastoma cells, cervical cancer cells, glioma cells, breast cancer cells, pancreatic cancer cells, Ewings sarcoma cells, rhabdomyosarcoma cells, osteosarcoma cells, retinoblastoma cells, Wilms' tumor cells, and pediatric brain tumor cells.

In another aspect, the disclosure encompasses a method of diagnosing cancer in a subject. The method includes one or more of the imaging/detection steps outlined above. In the method, the biological sample is obtained from, part of, or all of a subject. If cancer cells are detected or imaged in the method steps, the subject is diagnosed with cancer. In certain embodiments, the method of diagnosing cancer in a subject is followed by a step of treating the subject diagnosed with cancer with a cancer therapy. In some embodiments, the cancer therapy is, surgery, chemotherapy or radiotherapy.

In some embodiments, the cancer that is diagnosed is an adult solid tumor or a pediatric solid tumor. Non-limiting examples of such cancer include melanoma, neuroblastoma, lung cancer, adrenal cancer, colon cancer, colorectal cancer, ovarian cancer, prostate cancer, liver cancer, subcutaneous cancer, squamous cell cancer, intestinal cancer, retinoblastoma, cervical cancer, glioma, breast cancer, pancreatic cancer, Ewings sarcoma, rhabdomyosarcoma, osteosarcoma, retinoblastoma, Wilms' tumor, and pediatric brain tumors.

In still another aspect, the disclosure encompasses a method of monitoring the efficacy of a cancer therapy in a human subject. The method includes performing one or more of the imaging/detection steps outlined above at two or more different times on the biological sample, wherein the biological sample is obtained from, part of, or all of a subject. The change in strength of the signals characteristic of the metal isotope between the two or more different times is correlated with the efficacy of the cancer therapy.

In another aspect, the disclosure encompasses a method of treatment of abnormal, but not malignant, tissue, such as defects of the musculoskeletal system using FAP as a targeting vector or vascular system using cRGD as a targeting vector. The method includes the step of contacting one or more abnormal cells with an effective amount of one or more of the zwitterionic metal chelators described above, wherein the metal atom is a radioactive metal isotope known to emit ionizing radiation in a form that would result in a therapeutic effect on the cells that take up the analogs.

In another aspect, the disclosure encompasses a method of treating a cancer by administering an effective amount of a therapeutic agent comprising a zwitterionic metal chelator complex and a pharmaceutically acceptable carrier or excipient. The method comprises a step to diagnose the cancer and a step of administering the therapeutic agent to a subject determined to be in need thereof;

wherein the step to diagnose the cancer comprises:
- contacting cells, tissues or organs of a subject with an imaging agent,
- imaging the cells, tissues, or organs of the subject using positron emission tomography (PET), single-photon emission computerized tomography (SPECT), or magnetic resonance imaging (MRI), and
- diagnosing the cancer in the cells tissues, or organs of the subject based on imaging data collected;

and wherein the metal atom complexed to the zwitterionic metal chelator is:
- a radioactive metal isotope known to emit ionizing radiation that results in the death of cells that take up the analogs;
- or a non-radioactive metal that is capable of releasing cytotoxic radiation upon irradiation with alpha emission, beta emission, neutron capture, or a combination thereof.

In still another aspect, the disclosure encompasses a method of treating a rare or childhood cancer by administering an effective amount of a therapeutic agent comprising a zwitterionic metal chelator complex and a pharmaceutically acceptable carrier or excipient. In such aspects, the therapeutic agent may further comprise one or more targeting vectors selected from the group consisting of cRGD, PSMA, FAP, octreotide, bombesin, or a homomeric or heteromeric oligomers formed from their combination.

In certain embodiments, the targeting ligand includes one or more of LyP-1 peptide having a sequence of CGQKRTRGC (SEQ ID NO: 1) and binding to P32 for diagnosing/treating melanoma; K237 peptide having a sequence of HTMYYHHYQHHL(SEQ ID NO: 2) and binding to VEGFR-2 for diagnosing/treating breast tumor; IL4RPep-1 peptide having a sequence of CRKRLDRNC(SEQ ID NO: 3) and binding to IL4R for diagnosing/treating lung tumor, breast tumor, colon tumor; mUNO peptide having a sequence of CSPGAK (SEQ ID NO: 4) and binding to CD206 for diagnosing/treating breast tumor; folate receptors for diagnosing/treating ovarian and lung cancer; GE11, a dodecapeptide, binding to epidermal growth factor receptor (EGFR or ErbB1) for diagnosing/treating tumors of epithelial origin. In addition, the metal atom complexed to the zwitterionic metal chelator is:
- a radioactive metal isotope known to emit ionizing radiation that results in the death of cells that take up the analogs;
- or a non-radioactive metal that is capable of releasing cytotoxic radiation upon irradiation with alpha emission, beta emission, neutron capture, or a combination thereof.

In particular embodiments, the rare or childhood cancer is: Acinic cell carcinoma, ACTH-secreting tumor, Actinic keratosis, Adamantinoma, Adenoid cystic carcinoma, Alveolar soft part sarcoma, Ampullary cancer, Angiosarcoma, Appendix (appendiceal) neuroendocrine (carcinoid) tumor, Askin tumor—a type of Ewing tumor (Ewing sarcoma), Bartholin gland cancer, Basaloid squamous cell carcinoma of the anus, Bowen disease, Bronchioloalveolar carcinoma, Carcinoid tumor, Carcinoma of the ampulla of Vater, Cardiac angiosarcoma, Castleman disease, Cholangiocarcinoma, Choriocarcinoma, Choroid plexus tumor, Chondrosarcoma, Chordoma, Chromophobe renal cell carcinoma, Clear cell sarcoma, Craniopharyngioma, Dermatofibrosarcoma protuberans, Desmoid tumor, Desmoplastic small round cell tumor, Dysgerminoma, Embryonal carcinoma, Endodermal sinus tumor, Endometrial stromal sarcoma, Ependymoma, Epithelial appendix (appendiceal) cancer, Epithelial-myoepithelial carcinoma, Epithelioid hemangioendothelioma (EHE), Epithelioid sarcoma, Essential thrombocythemia, Esthesioneuroblastoma (olfactory neuroblastoma), Extra-cranial malignant rhabdoid tumor (MRT), Extranodal NK/T-cell lymphoma-nasal type, Fallopian tube cancer,Fibrolamellar carcinoma, Fibromatosis, Fibromyxoid sarcoma (Evans' tumor), Fibrosarcoma Folliculotropic mycosis fungoides, Ganglioglioma, Ganglioneuroblastoma, Gastric Adenocarcinoma and Proximal Polyposis of the Stomach (GAPPS), Gastrinoma, Gastroesophageal junction (GEJ) cancer, Gestational trophoblastic disease (GTD) (hydatidiform mole; gestational trophoblastic neoplasia), Germ cell tumor, Giant cell tumor of bone, Glucagonoma, Granulomatous slack skin, Heart cancer (cardiac angiosarcoma), Hemangioendothelioma, Hemangiosarcoma, Hepatobiliary cancer, Hepatoblastoma, Hepatocellular carcinoma, Hepatoma, Hereditary diffuse gastric cancer (HDGC), Hurthle cell cancer (oxyphil cell carcinoma), Insulinoma, Islet cell tumor, Keratoacanthoma, Klatskin tumor, Large cell neuroendocrine carcinoma, Leiomyosarcoma, Leydig cell tumor, Lip cancer, Liposarcoma, Lymphomatoid papulosis, Lymphoplasmacytic lymphoma, Malignant mesenchymoma, Malignant mixed mullerian tumor, Malignant peripheral nerve sheath tumor (MPNST), Malignant rhabdoid tumor of the kidney, Medulloepithelioma, Meningioma, Mesoblastic nephroma, Metaplastic cancer of the breast, Monoclonal gammopathy of undetermined significance (MGUS), Mouth cancer, Mucinous cystic neoplasm, Mucoepidermoid carcinoma, Muscle cancer (myosarcoma), Myoepithelial carcinoma, Mycosis fungoides, Myelofibrosis, Myxofibrosarcoma, Nephroblastoma, Neuroendocrine carcinoma of the skin, NUT carcinoma, Oat cell cancer, Occult primary cancer, Ocular or intraocular melanoma, Olfactory neuroblastoma (esthesioneuroblastoma), Oligodendroglioma, Oncocytic carcinoma, Ovarian small cell cancer, Paget disease, Pagetoid reticulosis, Paraganglioma, Parathyroid cancer, Periosteal osteosarcoma, Peripheral primitive neuroectodermal tumor (PPNET), Pheochromocytoma, Phyllodes tumor, Pineoblastoma, Plasmacytoma, Polycythemia vera, Polymorphous low-grade adenocarcinoma, Primary cutaneous lymphoma, Primary peritoneal carcinoma, Prolactinoma (lactotroph adenoma), Renal cell carcinoma, Sarcomatoid carcinoma (carcinosarcoma), Schwannoma, Sclerosing epithelioid fibrosarcoma, Sebaceous carcinoma, Seminoma, Sertoli cell tumor, Sezary syndrome, Sinus cancer, Skin adnexal tumors, Solid pseudopapillary neoplasm, Solitary fibrous tumor, Solitary plasmacytoma, Somatostatinoma, Spermatocytic seminoma, Spindle cell neoplasm, spindle cell tumor, spindle cell carcinoma, spindle cell sarcoma, Subcutaneous panniculitis-like T-cell lymphoma, Synovial sarcoma, T-cell lymphoma, Teratoma, Throat cancer, Thymoma, Tongue cancer, Tonsil cancer, Trabecular cancer, Translocation renal cell carcinoma, Transitional cell carcinoma (urothelial carcinoma), Undifferentiated pleomorphic sarcoma, Urachal cancer, Urethral cancer, Urothelial carcinoma (transitional cell carcinoma), Uterine cancer, Verrucous carcinoma, VIPoma, Vocal cord/voice box cancer, Womb cancer, or Yolk sac tumor.

Non-Cancerous Conditions

In another aspect, the invention provides a method of treating a non-cancerous condition in a subject in need thereof, the method comprising: administering to the subject an effective amount of a therapeutic agent comprising a zwitterionic metal chelator complex and a pharmaceutically acceptable carrier or excipient. In certain embodiments, the metal atom complexed to the zwitterionic metal chelator is:

a radioactive metal isotope known to emit ionizing radiation that results in a therapeutic effect on the subject.

or a non-radioactive metal that is capable of releasing therapeutic radiation upon irradiation with alpha emission, beta emission, neutron capture, or a combination thereof.

In certain embodiments, the non-cancerous condition is a musculoskeletal disorders or a tissue hypertrophy disorder. In still other embodiments, the non-cancerous condition is myocardial infarction, atherosclerosis, or fibro-inflammatory disease (including, but not limited to interstitial lung disease, rheumatoid arthritis, liver fibrosis, and keloids).

In still other embodiments, the subject is a human.

Efficacy Measurements of Biological Systems

In another aspect, the disclosure encompasses a method of measuring the efficacy of a biological system of a subject. In particular embodiments, the biological system to be measured or monitored is the renal system, the hepatic system, or the blood pool.

In particular embodiments, the method of measuring the efficacy of a biological system includes:

(a) administering a quantifiable amount of a diagnostic agent comprising a zwitterionic metal chelator complex and a pharmaceutically acceptable carrier or excipient to the subject;

(b) imaging the subject with positron emission tomography (PET), single-photon emission computerized tomography (SPECT), or magnetic resonance imaging (MRI); and (c) determining the amount of therapeutic agent present in the biological system being observed in the subject.

In a particular aspect, the disclosure encompasses a method of measuring the efficacy of renal function a subject. In particular embodiments, the method comprises:

(a) administering a quantifiable amount of a diagnostic agent comprising a zwitterionic metal chelator complex and a pharmaceutically acceptable carrier or excipient to the subject;

(b) imaging the subject with positron emission tomography (PET), single-photon emission computerized tomography (SPECT), or magnetic resonance imaging (MRI); and (c) determining the amount of therapeutic agent present in the biological system being observed in the subject.

In another aspect, the invention provides a method of quantifying the glomerual filtration rate of a subject. In particular embodiments, the method comprises:

(a) administering a quantifiable amount of a diagnostic agent comprising a zwitterionic metal chelator complex and a pharmaceutically acceptable carrier or excipient to the subject; and (b) determining the amount of diagnostic agent present in the blood and urine of the subject as a function of time using either measurements of each bodily fluid or imaging the subject with positron emission tomography (PET), single-photon emission computerized tomography (SPECT), or magnetic resonance imaging (MRI).

Radiosurgery

Radiosurgery is a known method of treating targets in the body. During radiosurgery, the target is bombarded with a series of X-ray beams fired from various different positions and orientations by using a radiation delivery system, to affect the tumor biology using the cumulative radiation dose at the target. The radiation can be delivered invasively in conjunction with traditional scalpel surgery, or through a percutaneous catheter. CyberKnife™ (Accuray Inc.) and Trilogy™ (Varian Medical Systems) are two such radiation delivery systems. Advances in stereotactic surgery have provided increased accuracy in registering the position of tissue targeted for treatment and a radiation source. For example, see U.S. Pat. Nos. 6,351,662 and 6,402,762. Stereotactic radiosurgery systems may be commercially available from ACCURAY, INC. of Sunnyvale, Calif., and BRAINLAB. The Accuray Cyberknife™ stereotactic radiosurgery system has reportedly been used to provide targeted, painless, and fast treatment of tumors.

In one aspect, the invention provides a radiosurgical method for treating a patient body, the method comprising:

receiving a desired lesion pattern and planned radiation distribution;

administering an effective amount of a diagnostic agent comprising a zwitterionic metal chelator complex and a pharmaceutically acceptable carrier or excipient to the subject to effectively image the desired lesion pattern; and performing surgery on the desired lesion pattern to treat the patient body.

In certain embodiments, the surgery can be using scalpel surgery or a stereotactic radiosurgery system to administer a cumulative radiation dose.

In other embodiments, the zwitterionic metal chelator of the diagnostic agent further comprises one or more targeting vectors wherein the one or more targeting vectors are cRGD, KUE, dPSMA-617, a FAP-targeting molecule, octreotide, bombesin, or homomeric or heteromeric oligomers formed from their combination. In certain embodiments, the targeting ligand includes one or more of LyP-1 peptide having a sequence of CGQKRTRGC (SEQ ID NO: 1) and binding to P32 for diagnosing/treating melanoma; K237 peptide having a sequence of HTMYYHHYQHHL(SEQ ID NO: 2) and binding to VEGFR-2 for diagnosing/treating breast tumor; IL4RPep-1 peptide having a sequence of CRKRLDRNC (SEQ ID NO: 3) and binding to IL4R for diagnosing/treating lung tumor, breast tumor, colon tumor; mUNO peptide having a sequence of CSPGAK (SEQ ID NO: 4) and binding to CD206 for diagnosing/treating breast tumor; folate receptors for diagnosing/treating ovarian and lung cancer; GE11, a dodecapeptide, binding to epidermal growth factor receptor (EGFR or ErbB1) for diagnosing/treating tumors of epithelial origin.

In still other embodiments, the desired lesion pattern is received from a user interface of a treatment planning module. Such planning modules can be pre-programmed with specifications for various disease states and cancerous conditions. Alternatively, specifications for desired lesion patterns can be identified and produced using artificial intelligence data.

Toxic Metals

The zwitterionic metal chelators described herein can also be used as a treatment for removal of toxic or excess metals in a subject. In such methods, the zwitterionic metal chelators are administered without a metal coordinated thereto. The chelators act to bind excess or toxic metals in the subject which are then cleared along with the chelators through the kidneys and the renal system. The use of zwitterionic metal chelators for this method allows for faster removal of excess metals from a subject with increased clearance times and less damage to the liver and other organs.

As such, in one aspect, this disclosure encompasses a method for removing toxic or excess metals in a subject in need of such treatment, the method comprising:

(a) administering a therapeutically effective amount of a therapeutic agent to the subject, wherein the therapeutic agent comprises a metal chelator having one or more zwitterionic groups which is not coordinated to a metal or metal isotope, and a pharmaceutically acceptable carrier or excipient.

In certain embodiments, the metal chelator of the therapeutic agent has the formula:

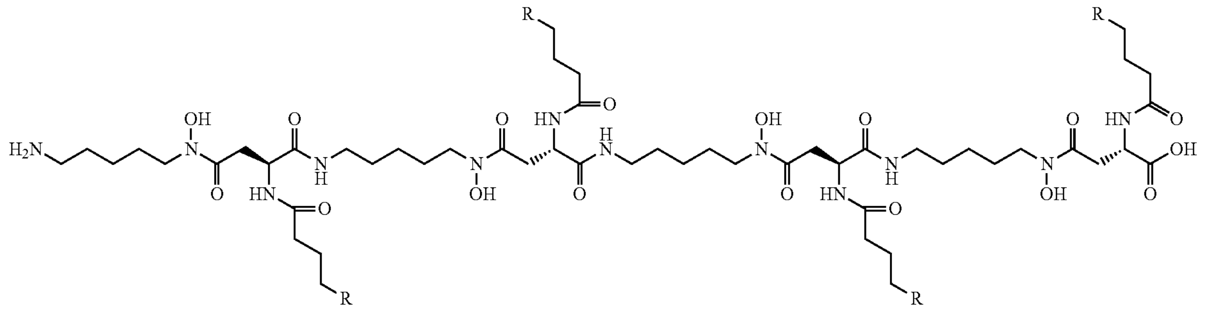

$NH_2$-$(ZWI)_4$-DFO*-$CO_2H$

-continued

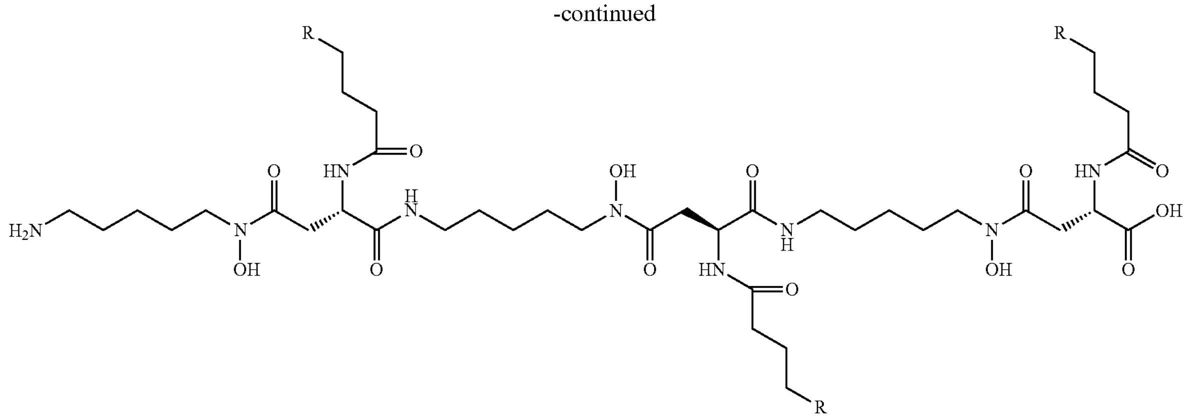

$NH_2$-(ZWI)$_3$-DFO-$CO_2H$

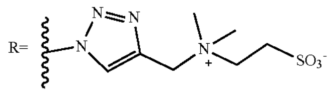

In still other embodiments, the toxic or excess metals are lead, mercury, arsenic, cadmium, thallium, iron, zinc, chromium, manganese, aluminum, cobalt, selenium, beryllium, lithium, silver, or tin.

In still other embodiments, the toxic or excess metals are lead, mercury, arsenic, cadmium, thallium, iron, zinc, chromium, manganese, aluminum, cobalt, selenium, beryllium, lithium, silver, or tin.

Other Applications—Agricultural and Chemical Processes

Zwitterionic metal chelators improve solubility and minimize non-specific interactions. It is believed that these improved properties result from the balancing of formal charges on the metal chelator, rendering a polyionic yet "charge-balanced" molecule having a net charge that is neutral or close to neutral, with an extended sphere of hydration and better isolation of the metal.

The zwitterionic metal chelators described herein can also be used in agricultural systems. In particular embodiments, zwitterionic metal chelators described herein can be used to supply micronutrients (trace metals such as iron, zinc, manganese, and copper) to various crops and plants. These micronutrients can help prevent drought and other diseases, particularly those caused by over-usage of certain fertilizers (particularly phosphorous fertilizer). Similarly, the zwitterionic metal chelators described herein can be used to supply various herbicidal formulations which are otherwise insoluble.

Similarly, the zwitterionic metal chelators described herein can also be used in chemical processes. As with the exposure to toxic metals described herein, certain chemical processes require the sequestration and removal of excess metals, such as metal catalysts. As such, the zwitterionic metal chelators described herein can also be used in such chemical process to remove insoluble metal impurities and/or unwanted metal components from the chemical process.

In particular, the zwitterionic metal chelators described herein have an advantage as compared to traditional metal chelators in the polarity of the zwitterionic molecules. As a result of this polarity, the zwitterionic metal chelators described herein can be used in aqueous solution, e.g. to increase solubility of a metal, and can then be precipitated from solution by addition of less polar solvents. This precipitation allows for the capture and subsequent disposal of undesired metals,—for example in capturing iron from wastewater (urban mining). In other embodiments, the zwitterionic metal chelators described herein which include sulfobetaines, precipitation can be induced by salt addition.

Dosage Forms and Administration Methods

In the methods of the invention, the zwitterionic metal chelators are administered at a predetermined dosage. The predetermined dosage amount is not particularly limited provided that the predetermined dosage is administered at least a minimum amount capable of being cleared by the kidneys within twelve hours. In particular embodiments utilizing non-radioactive techniques, the predetermined dosage is 0.5 mg/kg of body weight; 0.25 mg/kg of body weight; 0.1 mg/kg of body weight; 0.05 mg/kg of body weight; 0.01 mg/kg of body weight; 0.005 mg/kg of body weight; or 0.001 mg/kg of body weight. In other embodiments, the predetermined dosage is 5.0 mg; 2.5 mg, 1.0 mg; 0.75 mg; 0.5 mg; 0.25 mg; or 0.1 mg. In particular embodiments utilizing radioactive techniques, the dose will be limited by dose-limiting toxicity. In general, effective doses will be in the range of 0.1 mCi to 20 mCi for imaging, and 0.1-10 mCi/kg for therapy.

In some embodiments, a detectably effective amount of the zwitterionic metal chelators of the presently disclosed methods is administered to a subject. In accordance with the presently disclosed subject matter, "a detectably effective amount" of the imaging agent is defined as an amount sufficient to yield an acceptable image using equipment which is available for clinical use. A detectably effective amount of the agent may be administered in more than one injection. The detectably effective amount of the imaging agent can vary according to factors such as the degree of susceptibility of the individual, the age, sex, and weight of the individual, idiosyncratic responses of the individual, the dosimetry, and instrument and film-related factors. Optimization of such factors is well within the level of skill in the art.

The administration of the agent of the invention can be by any means described herein and as generally acceptable to the patient and one of ordinary skill in the art. In particular, the administration of the charge-balanced imaging agent is intravenous.

The predetermined target amount is dependent on a variety of factors including, but not limited to the type of tumor or condition to be observed and the location of any cells desired to be imaged. As such, the predetermined amount is set by one of ordinary skill in the art prior to administration of the agent. Such factors include, but are not limited to, the determined dosage amount, the height, weight, age, body mass index, and gender of the patient or any combination thereof.

In particular embodiments utilizing non-radioactive techniques, when the predetermined dosage amount is between about 2.5 mg and about 5.0 mg or greater, the predetermined target amount is 50% of the pre-determined dosage amount. In other embodiments, when the predetermined dosage amount is between about 0.5 mg and about 2.5 mg, the predetermined target amount is 60% of the pre-determined dosage amount. In still other embodiments, when the predetermined dosage amount is about 0.5 mg or less, the predetermined target amount is 80% of the pre-determined dosage amount.

Any route of administration may be suitable for administering the disclosed agents to a subject. In one embodiment, the disclosed zwitterionic metal chelators may be administered to the subject via intravenous injection. In another embodiment, the disclosed zwitterionic metal chelators may be administered to the subject via any other suitable systemic deliveries, such as parenteral, intranasal, sublingual, rectal, or transdermal administrations.

In another embodiment, the disclosed zwitterionic metal chelators may be administered to the subject via intraperitoneal injection or IP injection.

In another embodiment, the disclosed zwitterionic metal chelators may be administered to the subject via intratumoral injection.

For treatment of non-malignant or malignant tissues using neutron capture therapy, the subject is bombarded with neutrons at the appropriate energy after administration of the (typically targeted) zwitterionic chelator and adequate time for biodistribution, binding, and clearance of unbound dose.

The disclosure also includes methods of using pharmaceutical compositions comprising one or more of the disclosed zwitterionic metal chelators in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for parenteral, intranasal, sublingual or rectal administration, or for administration by inhalation or insufflation.

For preparing solid compositions such as tablets, the principal active ingredient is mixed with a pharmaceutically acceptable carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture for a zwitterionic metal chelator of the present invention, or a pharmaceutically acceptable salt thereof. When referring to these preformulation compositions as homogeneous, it is meant that the active ingredient is dispersed evenly throughout the composition so that the composition may be easily subdivided into equally effective unit dosage forms such as tablets, pills and capsules. This solid pre-formulation composition is then subdivided into unit dosage forms of the type described above containing from 0.1 to about 500 mg of the active ingredient of the present invention. Typical unit dosage forms contain from 1 to 100 mg, for example, 1, 2, 5, 10, 25, 50 or 100 mg, of the active ingredient. The tablets or pills of the novel composition can be coated or otherwise compounded to provide a dosage affording the advantage of prolonged action. For example, the tablet or pill can comprise an inner dosage and an outer dosage component, the latter being in the form of an envelope over the former. The two components can be separated by an enteric layer which, serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the zwitterionic metal chelators may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium caboxymethylcellulose, methylcellulose, polyvinylpyrrolidone or gelatin.

The disclosed zwitterionic metal chelators are particularly useful when formulated in the form of a pharmaceutical injectable dosage, including in combination with an injectable carrier system. As used herein, injectable and infusion dosage forms (i.e., parenteral dosage forms) include, but are not limited to, liposomal injectables or a lipid bilayer vesicle having phospholipids that encapsulate an active drug substance. Injection includes a sterile preparation intended for parenteral use.

Five distinct classes of injections exist as defined by the USP: emulsions, lipids, powders, solutions and suspensions. Emulsion injection includes an emulsion comprising a sterile, pyrogen-free preparation intended to be administered parenterally. Lipid complex and powder for solution injection are sterile preparations intended for reconstitution to form a solution for parenteral use. Powder for suspension injection is a sterile preparation intended for reconstitution to form a suspension for parenteral use. Powder lyophilized for liposomal suspension injection is a sterile freeze dried preparation intended for reconstitution for parenteral use that is formulated in a manner allowing incorporation of liposomes, such as a lipid bilayer vesicle having phospholipids used to encapsulate an active drug substance within a lipid bilayer or in an aqueous space, whereby the formulation may be formed upon reconstitution. Powder lyophilized for solution injection is a dosage form intended for the solution prepared by lyophilization ("freeze drying"), whereby the process involves removing water from products in a frozen state at extremely low pressures, and whereby subsequent addition of liquid creates a solution that conforms in all respects to the requirements for injections. Powder lyophilized for suspension injection is a liquid preparation intended for parenteral use that contains solids suspended in a suitable fluid medium, and it conforms in all respects to the requirements for Sterile Suspensions, whereby the medicinal agents intended for the suspension are prepared by lyophilization. Solution injection involves a liquid preparation containing one or more drug substances dissolved in a suitable solvent or mixture of mutually miscible solvents that is suitable for injection.

Solution concentrate injection involves a sterile preparation for parenteral use that, upon addition of suitable solvents, yields a solution conforming in all respects to the requirements for injections. Suspension injection involves a liquid preparation (suitable for injection) containing solid particles dispersed throughout a liquid phase, whereby the particles are insoluble, and whereby an oil phase is dispersed throughout an aqueous phase or vice-versa. Suspension liposomal injection is a liquid preparation (suitable for injection) having an oil phase dispersed throughout an aqueous phase in such a manner that liposomes (a lipid bilayer vesicle usually containing phospholipids used to encapsulate an active drug substance either within a lipid bilayer or in an aqueous space) are formed. Suspension sonicated injection is a liquid preparation (suitable for injection) containing solid particles dispersed throughout a liquid phase, whereby the particles are insoluble. In addition, the product may be sonicated as a gas is bubbled through the suspension resulting in the formation of microspheres by the solid particles.

The parenteral carrier system includes one or more pharmaceutically suitable excipients, such as solvents and cosolvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives.

The present invention also provides packaged pharmaceutical compositions comprising a pharmaceutical acceptable carrier and a zwitterionic metal chelator of the invention. In certain embodiments the packaged pharmaceutical composition will comprise the reaction precursors necessary generate the zwitterionic metal chelator of the invention upon combination with a metal or radiolabeled precursor.

The invention also permits the zwitterionic metal chelator to be provided in a non-radioactive "kit" form comprised of the non-radioactive zwitterionic chelator/targeting vector molecule, a preparation apparatus (for example, a hot plate), and quality control devices (for example, a test strip or equivalent). The user would add the radioactive metal to create the final injected drug immediately before use as an imaging agent and/or therapeutic agent. In this way, the kit can be manufactured and shipped in a non-radioactive form, and the radioactive metal is added at the site. The non-radioactive zwitterionic chelator/targeting vector molecule may be provided in solution or in lyophilized form. When the imaging agent and carrier of the kit are in lyophilized form, the kit may optionally contain a sterile and physiologically acceptable reconstitution medium such as water, saline, buffered saline, and the like.

The kit may provide a zwitterionic metal chelator of the invention in solution or in lyophilized form, and these components of the kit of the invention may optionally contain stabilizers such as NaCl, silicate, phosphate buffers, ascorbic acid, gentisic acid, and the like. Additional stabilization of kit components may be provided in this embodiment, for example, by providing the reducing agent in an oxidation-resistant form.

Determination and optimization of such stabilizers and stabilization methods are well within the level of skill in the art. When the targeting molecule/chelating agent of this embodiment are in lyophilized form, the kit may optionally contain a sterile and physiologically acceptable reconstitution medium such as water, saline, buffered saline, and the like. The amounts of unlabeled targeting molecule/chelating agent, auxiliary molecule, and reducing agent in this embodiment are optimized in accordance with the methods for making the cardiovascular imaging agent set forth above. Radionuclides may be combined with the unlabeled targeting molecule/chelating agent and the reducing agent for a time and at a temperature sufficient to chelate the radionuclide to the targeting molecule/chelating agent, and the imaging agent thus formed is injected into the patient.

Imaging agents of the invention may be used in accordance with the methods of the invention by one of skill in the art. Images can be generated by virtue of differences in the spatial distribution of the imaging agents which accumulate at a site. The spatial distribution may be measured using any means suitable for the particular label, for example, a gamma camera, a PET apparatus, a SPECT apparatus, and the like. The extent of accumulation of the imaging agent may be quantified using known methods for quantifying radioactive emissions. A particularly useful imaging approach employs more than one imaging agent to perform simultaneous studies.

Generally, the diagnostic compositions are administered in doses effective to achieve the desired signal strength to enable detection. Such doses can vary, depending upon the organs or tissues to be imaged, and the imaging equipment being used. For example, Zeheer et al., *Nature Biotechnology,* 19, 1148-1154 (2001) uses 0.1 μmol/kg as a dose for IRDye78 conjugates in vivo. The diagnostic compositions can be administered to a patient systemically or locally to the organ or tissue to be imaged, and then the patient is subjected to the imaging procedure.

Preferably, a detectably effective amount of the imaging agent of the invention is administered to a subject. In accordance with the invention, "a detectably effective amount" of the imaging agent of the invention is defined as an amount sufficient to yield an acceptable image using equipment which is available for clinical use. A detectably effective amount of the imaging agent of the invention may be administered in more than one injection. The detectably effective amount of the imaging agent of the invention can vary according to factors such as the degree of susceptibility of the individual, the age, sex, and weight of the individual, idiosyncratic responses of the individual, the dosimetry. Detectably effective amounts of the imaging agent of the invention can also vary according to instrument and film-related factors. Optimization of such factors is well within the level of skill in the art.

The amount of imaging agent used for diagnostic purposes and the duration of the imaging study will depend upon the radionuclide used to label the agent, the body mass of the patient, the nature and severity of the condition being treated, the nature of therapeutic treatments which the patient has undergone, and on the idiosyncratic responses of the patient. Ultimately, the attending physician will decide the amount of imaging agent to administer to each individual patient and the duration of the imaging study.

EXAMPLES

Example 1: Preparation of Zwitterionic Metal Chelators

1-Benzyl 4-(tert-butyl) 2-hydroxysuccinate 2

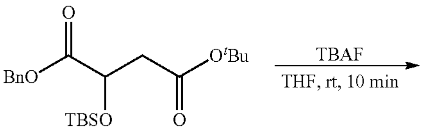

1

-continued

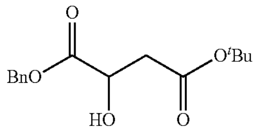

2

Benzyl tert-Butyl (S)-2-(tert-Butyldimethylsilyloxy)succinate 1 (1.78 g, 4.52 mmol, 1.00 eq.) was added to a solution of TBAF in THF (1 m solution, 6.78 mL, 6.78 mmol, 1.50 eq.) and 1 mL THF was added. The solution was stirred at rt for 15 min. $CH_2Cl_2$ (25.0 mL) was added and the solution was washed with brine (20 mL), the organic phase was dried over $Na_2SO_4$, filtered and the solvent was removed in vacuo. The crude product was purified via column chromatography on silica (MN BT25 cartridge, loaded as solution, gradient: PE/EtOAc 5:1 to 0:1). The title compound 2 was obtained as a yellow oil (1.09 g, 86%).

1-Benzyl-4-(tert-butyl)-2-triflyloxysuccinate 3

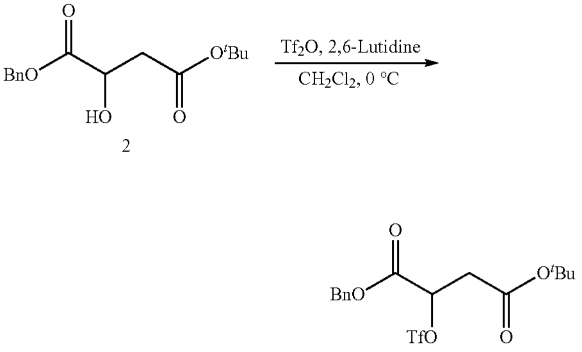

2

3

2,6-Lutidine (517 μL, 4.46 mmol, 1.50 eq.) was added to a solution of 1-benzyl 4-(tert-butyl) 2-hydroxysuccinate 2 (833 mg, 2.97 mmol, 1.00 eq.) in $CH_2Cl_2$ (11.9 mL) at 0 °C under nitrogen atmosphere. A solution of $Tf_2O$ (700 μL, 4.16 mmol, 1.40 eq.) in $CH_2Cl_2$ (1.05 mL) was added via a syringe pump (4 mL/h) and the solution was stirred at 0 °C for 50 min. Pentane (60.0 mL) was added and the solution was washed with a 3:1 mixture of brine and 1 m aq. HCl. The organic phase was dried over $Na_2SO_4$, filtered and the solvent was removed in vacuo. The crude product was purified via column chromatography on silica (loaded as solution in PE/$CH_2Cl_2$ 1:1 (1 mL), MN Cartridge BT15, PE/$CH_2Cl_2$ 1:1). 1-Benzyl-4-(tert-butyl)-2-triflyloxysuccinate 3 (1.08 g, 89%) was obtained as an orange oil.

Monosubstituted Cyclen 5

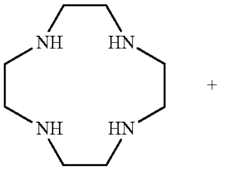

4

-continued

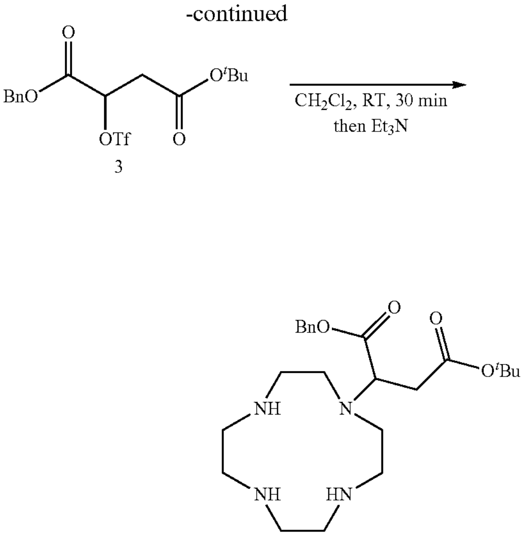

3

5

A solution of 1-benzyl-4-(tert-butyl)-2-triflyloxysuccinate 3 (778 mg, 1.89 mmol, 1.00 eq.) in $CH_2Cl_2$ (8.30 mL) was added dropwise to a solution of cyclen 4 (650 mg, 3.77 mmol, 2.00 eq.) in $CH_2Cl_2$ (44.1 mL) over 30 min. The resulting mixture was stirred for 22 h at rt. $Et_3N$ (3.11 mL) was added and the solution was stirred for 10 min. All volatiles were removed in vacuo. The resulting crude product was dissolved in EtOAc (120 mL) and washed with $H_2O$ (3×120 mL) and brine (120 mL). The solvent was removed in vacuo to give the title compound 5 as a colourless oil (700 mg, 85%).

DOT3AZA1COOH tert-butylester 7

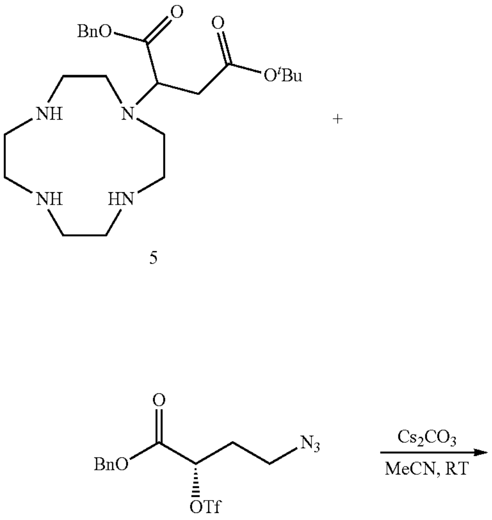

5

6

-continued

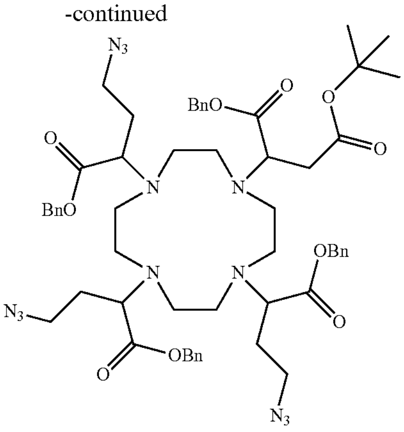

7

Cyclen (150 mg, 345 mol, 1.00 eq.) was dissolved in MeCN (23.5 mL) and $Cs_2CO_3$ (426 mg, 1.21 mmol, 3.50 eq.) was added under nitrogen. Azidotriflate (419 mg, 1.14 mmol, 3.30 eq.) dissolved in MeCN (11.5 mL) was added dropwise. The resulting mixture was stirred for 22 h at rt under nitrogen. The suspension was filtered and the solvent was removed in vacuo. The crude product was purified via column chromatography on silica (loaded as solution in $CH_2Cl_2$ (1.5 mL), MN Cartridge BT15, gradient: $CH_2Cl_2$/MeOH 100:0 zu 99:1 to 98:2). The title compound was obtained as a colourless oil (79 mg, 21%).

Zwitterionic chelator 9

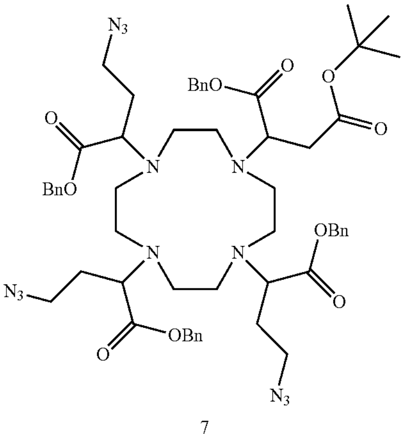

7

+

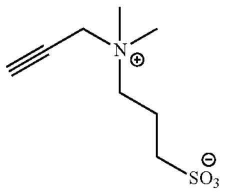

8

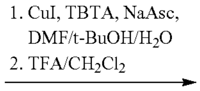

-continued

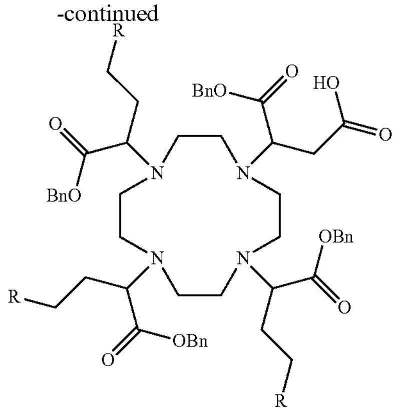

9

R =

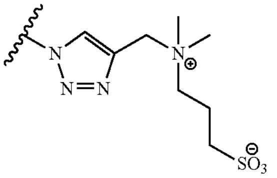

In a typical experiment, the alkyne 8 (4 eq), CuI (0.550 eq) and NaAsc (1.20 eq) are dissolved under $N_2$-atmosphere in degassed DMF/t-BuOH/$H_2O$ and stirred at rt for 30 min. The azide 7 (1.00 eq) is dissolved in degassed DMF/t-BuOH/$H_2O$ under $N_2$-atmosphere. The two solutions are combined and subsequently stirred at 50 °C for 24 h. A solution of $Na_2S$ in water is then added to the mixture. The suspension is stirred at rt for 10 min, filtered and the solvent was removed in vacuo. The crude product is dissolved in $CH_2Cl_2$/TFA (1:1) and stirred for 4 h. The solvent is removed in vacuo and the crude product is purified by crystzallisation to give the title compound 9.

Example 2: Imaging of Organisms

For in vivo characterization, 40 pmol/g (average 10 nmol) of a zwitterionic metal chelator complex can be injected IV into 25 g athymic nude mice harboring xenograft human tumors. Simultaneous color video and positron emission tomography (PET), single-photon emission computerized tomography (SPECT), or magnetic resonance tomography (MRT) can be acquired pre-injection, every 1 sec for the first 20 sec then every 1 min for 2 h. Camera acquisition can be held constant (typically 100 msec) and chosen to ensure that all intensity measurements are within a linear range. Blood can be sampled at 0, 1, 2, 5, 10, 15, 30, 60, and 120 min via tail vein. Intensity-time curves for all major organs and tissues can be quantified. The peak intensity and time can be determined for each tumor/tissue/organ, along with the intensity in each at 1 h post-injection.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Those skilled in the art will recognize, or be able to ascertain using no more than routine experimentation, many equivalents to the specific embodiments of the invention described herein.

Such equivalents are intended to be encompassed by the following claims.

| Year | DOI | Title | Authors | Citation |
|---|---|---|---|---|
| 2014 | 10.1002/ asia.201402250 | Synthesis of 1,4,7,10-tetra-azacyclododecan-1,4,7,10-tetra-azidoethylacetic acid (DOTAZA) and related "clickable" DOTA derivatives. | Kriemen et al. | *Chem. Asian J.* 2014, 9 (8), 2197-2204. |
| 2017 | | Poster-P342 Targeted Zwitterionic Radioligands for Improved Molecular Imaging | Henry et al. | *J. Label Compd Radiopharm*, 2017: 60 (Suppl. 1): S111-S640 |
| 2019 | 10.1021/ acs.jmedchem. 9b01606 | Nonradioactive Cell Assay for the Evaluation of Modular Prostate-Specific Membrane Antigen Targeting Ligands via Inductively Coupled Plasma Mass Spectrometry | Holzapfel et al. | *J. Med. Chem.*, 2019, 62, 10912-10918 |
| 2022 | 10.1002/ ejic.202200432 | Solution Structure and Relaxivity of Ln-DOTXAZA Derivatives. | Holzapfel et al. | *Eur. J. Inorg. Chem.* 2022, e202200432 |
| 2015 | 10.1002/ ejic.201500789 | Synthesis and Structural Analysis of 1,4,7,10-tetra-azacyclododecan-1,4,7,10-tetra-azidoethylacetic acid (DOTAZA) Complexes | Kriemen et al. | Eur. J. Inorg. *Chem.* 2015, 5368-5378 |
| 2023 | 10.1002/ cmdc.2003000112 | Synthesis of Modular Desferriozamine Analogues and Evaluation of Derivatives for Zirconium Complexation | Outzen et al. | *ChemMedChem* 2023, e202300112 |

The contents of all patent, patent applications, and publications cited herein are incorporated herein by reference in their entireties.

The invention claimed is:

1. A zwitterionic metal chelator complex comprising a metal chelator having at least three zwitterionic groups; a metal or metal isotope selected from the group consisting of a radionuclide, a label, a paramagnetic metal and a heavy metal; and further comprising one or more targeting vectors; wherein the one or more targeting vectors are CRGD, KUE, PSMA-617, FAPI, octreotide, bombesin, or a homo- or hetero-dimer formed from their combination, wherein the metal chelator is a derivative of DOTA having the formula:

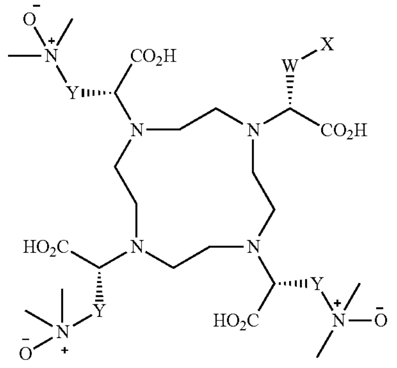

wherein each instance of W and Y independently is a linking group, and X is a reactive group.

2. The zwitterionic metal chelator complex according to claim 1, wherein the metal or metal isotope is Pb, Zr, Cu, Ga, In, Y, Gd, Lu, Ac or Tb.

3. An imaging agent comprising a zwitterionic metal chelator complex according to claim 1.

4. A method of imaging cells, tissues, or organs, the method comprising:

(a) contacting cells with an imaging agent according to claim 3; and (b) imaging the cells, tissues, or organs using positron emission tomography (PET), single-photon emission computerized tomography (SPECT), or magnetic resonance imaging (MRI).

5. A therapeutic agent comprising a zwitterionic metal chelator complex according to claim 1 and a pharmaceutically acceptable carrier or excipient.

6. A method of treating a cancerous condition in a subject in need thereof, the method comprising:

contacting cancer cells in the subject with an effective amount of a therapeutic agent according to claim 5, wherein the metal atom complexed to the zwitterionic metal chelator is:

a radioactive metal isotope known to emit ionizing radiation that results in the death of cells;

or a non-radioactive metal that is capable of releasing cytotoxic radiation upon irradiation with alpha emission, beta emission, neutron capture, or a combination thereof.

7. A method of treating a cancer by administering an effective amount of a therapeutic agent according to claim 5, wherein the method comprises a step to diagnose the cancer and a step of administering the therapeutic agent to a subject determined to be in need thereof;

wherein the step to diagnose the cancer comprises:

contacting cells, tissues or organs of a subject with an imaging agent, imaging the cells, tissues, or organs of the subject using positron emission tomography (PET), single-photon emission computerized tomography (SPECT), or magnetic resonance imaging (MRI), and diagnosing the cancer in the cells tissues, or organs of the subject based on imaging data collected;

and wherein the metal atom complexed to the zwitterionic metal chelator is:

a radioactive metal isotope known to emit ionizing radiation that results in the death of cells;

or a non-radioactive metal that is capable of releasing cytotoxic radiation upon irradiation with alpha emission, beta emission, neutron capture, or a combination thereof.

* * * * *